United States Patent
De Belle et al.

(10) Patent No.: US 9,422,350 B2
(45) Date of Patent: Aug. 23, 2016

(54) TARGET OF EGR1 (TOE1) POLYPEPTIDES FOR INHIBITION OF HIV

(76) Inventors: Ian De Belle, Kanata (CA); Sabina Sperandio, Kanata (CA)

(*) Notice: Subject to any disclaimer, the term of this patent is extended or adjusted under 35 U.S.C. 154(b) by 98 days.

(21) Appl. No.: 13/582,373

(22) PCT Filed: Mar. 4, 2011

(86) PCT No.: PCT/CA2011/000234
§ 371 (c)(1),
(2), (4) Date: Nov. 26, 2012

(87) PCT Pub. No.: WO2011/106882
PCT Pub. Date: Sep. 9, 2011

(65) Prior Publication Data
US 2013/0065819 A1  Mar. 14, 2013

(30) Foreign Application Priority Data
Mar. 4, 2010  (CA) .................................. 2695337

(51) Int. Cl.
| | |
|---|---|
| A61K 39/395 | (2006.01) |
| A61K 38/00 | (2006.01) |
| A61K 38/16 | (2006.01) |
| A01N 37/18 | (2006.01) |
| A61P 31/18 | (2006.01) |
| C12N 11/00 | (2006.01) |
| C12N 11/16 | (2006.01) |
| C12N 1/20 | (2006.01) |
| C12N 5/00 | (2006.01) |
| C12N 5/02 | (2006.01) |
| C07H 21/02 | (2006.01) |
| C07H 21/04 | (2006.01) |
| C07K 14/47 | (2006.01) |
| C07K 14/435 | (2006.01) |
| C07K 17/02 | (2006.01) |
| C07K 19/00 | (2006.01) |
| C07K 16/42 | (2006.01) |

(52) U.S. Cl.
CPC ............. C07K 14/47 (2013.01); C07K 14/435 (2013.01); C07K 14/4702 (2013.01); C07K 16/4225 (2013.01); C07K 17/02 (2013.01); C07K 19/00 (2013.01); C12N 5/00 (2013.01); A61K 38/00 (2013.01)

(58) Field of Classification Search
None
See application file for complete search history.

(56) References Cited

U.S. PATENT DOCUMENTS

| | | | | |
|---|---|---|---|---|
| 6,410,233 | B2* | 6/2002 | Mercola et al. | 435/6.11 |
| 6,982,145 | B1 | 1/2006 | Mercola et al. | |
| 2005/0282239 | A1* | 12/2005 | Allbritton et al. | 435/15 |
| 2006/0263774 | A1* | 11/2006 | Clark et al. | 435/6 |
| 2006/0275794 | A1* | 12/2006 | Carrino | C12Q 1/6876 435/6.18 |
| 2008/0095819 | A1* | 4/2008 | Gourdie et al. | 424/423 |

OTHER PUBLICATIONS

NCBI Database, Accession No. NP_057853, "Tat [Human immunodeficiency virus 1]", 2 pages (2008).*
EMBL Database, Accession No. CR457320, "Homo sapiens full open reading frame cDNA clone RZPDo834F0313D for gene TOE1, target of EGR1", 2 pages (2008).*
De Belle L et al . "In Vivo Cloning and Characterization of a New Growth Suppressor Protein TOEI as a Direct Target Gene of EGRI" J. Biol. Chem. Apr. 18, 2003, 278 (16) • 14306-12.
Database EMBL [Online] Jun. 3, 2004, "Homo sapiens full open reading frame cDNA clone RZPDo834F0313D for gene TOE1, target of EGR1, member 1 (nuclear); complete cds, incl. stopcodon." retrieved from EMBL accession No. CR457320.1.
Sperandio et al. "TOE1 interacts with p53 to modulate its transactivation potential" FEBS Lett. Jun. 7, 2009, 583 (2009): 2165-70.
Darbinian et al. "HIV-I Tat Inhibits NGF-Induced Egr-1 Transcriptional Activity and Consequent p35 Expression in Neural Cells" J.Cell Physiol. Jul. 2008, 261( 1): 128-34.
Extended European Search Report, Oct. 28, 2013, Application No. 11750121.3, European Patent Office, Munich, Germany.
Database UniProt [Online], 2008, Database accession No. B4DEM6.
Database UniProt [Online], 2008, Database accession No. B3KSC7.
Wagner E et al., "An Unconventional Human Ccr4-Caf1 Deadenylase Complex in Nuclear Cajal Bodies", Molecular and Cell Biology, vol. 27, 2007, pp. 1686-1695.
International Preliminary Report on Patentability PCT/CA2011/000234 dated Sep. 4, 2012.

* cited by examiner

*Primary Examiner* — Hames H Alstrom Acevedo
*Assistant Examiner* — Thea D'Ambrosio

(57) ABSTRACT

Described are methods and compositions for preventing and/or treating HIV infection, as well as in vitro and in vivo methods of inhibiting HIV replication, inhibiting HIV viral transcription, inhibiting the viral Tat protein, and inhibiting HIV LTR expression. The methods involve administering a Target of Egr1 (TOE1) polypeptide, fragment or deletion mutant thereof, either to a subject in need of treatment or to a cell infected with an HIV virus. Compositions may comprise the described polypeptide, or an encoding polynucleotide thereof.

16 Claims, 13 Drawing Sheets

Alignment in CLUSTAL W (1.83) format

Amino acids 1-60 (of TOE1)
```
TOE1
(SEQ ID NO:1)    MAADSDDGAVSTPAASDGGVSKSTTSGEELVVQVPVVDVQSNNFKEMWPSLLLAIKTANF
SEQ ID NO:2      ------------------------------------------------------------
SEQ ID NO:3      ------------------------------------------------------------
SEQ ID NO:4      ------------------------------------------------------------
SEQ ID NO:5      ------------------------------------------------------------
SEQ ID NO:6      ------------------------------------------------------------
SEQ ID NO:7      ------------------------------------------------------------
SEQ ID NO:8      ------------------------------------------------------------
SEQ ID NO:9      ------------------------------------------------------------
SEQ ID NO:10     ------------------------------------------------------------
SEQ ID NO:11     ------------------------------------------------------------
SEQ ID NO:12     ------------------------------------------------------------
SEQ ID NO:13     ------------------------------------------------------------
SEQ ID NO:14     ------------------------------------------------------------
SEQ ID NO:15     ------------------------------------------------------------
SEQ ID NO:16     ------------------------------------------------------------
SEQ ID NO:17     ------------------------------------------------------------
```

Amino acids 61-120 (of TOE1)
```
TOE1
(SEQ ID NO:1)    VAVDTELSGLGDRKSLLNQCIEERYKAVCHAARTRSILSLGLACFKRQPDKGEHSYLAQV
SEQ ID NO:2      ------------------------------------------------------------
SEQ ID NO:3      ------------------------------------------------------------
SEQ ID NO:4      ------------------------------------------------------------
SEQ ID NO:5      ------------------------------------------------------------
SEQ ID NO:6      ------------------------------------------------------------
SEQ ID NO:7      ------------------------------------------------------------
SEQ ID NO:8      ------------------------------------------------------------
SEQ ID NO:9      ------------------------------------------------------------
SEQ ID NO:10     ------------------------------------------------------------
SEQ ID NO:11     ------------------------------------------------------------
SEQ ID NO:12     ------------------------------------------------------------
SEQ ID NO:13     ------------------------------------------------------------
SEQ ID NO:14     ------------------------------------------------------------
SEQ ID NO:15     ------------------------------------------------------------
SEQ ID NO:16     ------------------------------------------------------------
SEQ ID NO:17     ------------------------------------------------------------
```

Figure 1

```
Amino acids 121-180 (of TOE1)
TOE1
(SEQ ID NO:1)    FNLTLLCMEEYVIEPKSVQFLIQHGFNFNQQYAQGIPYHKGNDKGDESQSQSVRTLFLEL
SEQ ID NO:2      ------------------------------------------------------------
SEQ ID NO:3      ------------------------------------------------------------
SEQ ID NO:4      ------------------------------------------------------------
SEQ ID NO:5      ------------------------------------------------------------
SEQ ID NO:6      ------------------------------------------------------------
SEQ ID NO:7      ------------------------------------------------------------
SEQ ID NO:8      ------------------------------------------------------------
SEQ ID NO:9      ------------------------------------------------------------
SEQ ID NO:10     ------------------------------------------------------------
SEQ ID NO:11     ------------------------------------------------------------
SEQ ID NO:12     ------------------------------------------------------------
SEQ ID NO:13     ------------------------------------------------------------
SEQ ID NO:14     ------------------------------------------------------------
SEQ ID NO:15     ------------------------------------------------------------
SEQ ID NO:16     ------------------------------------------------------------
SEQ ID NO:17     ------------------------------------------------------------

Amino acids 181-240 (of TOE1)
TOE1
(SEQ ID NO:1)    IRARRPLVLHNGLIDLVFLYQNFYAHLPESLGTFTADLCEMFPAGIYDTKYAAEFHARFV
SEQ ID NO:2      ---------------LVFLYQNFYAHLPESLGTFTADLCEMFPAGIYDTKYAAEFHARFV
SEQ ID NO:3      ---------------LVFLYQNFYAHLPESLGTFTADLCEMFPAGIYDTKYAAEFHARFV
SEQ ID NO:4      ---------------LVFLYQNFYAHLPESLGTFTADLCEMFPAGIYDTKYAAEFHARFV
SEQ ID NO:5      ---------------LVFLYQNFYAHLPESLGTFTADLCEMFPAGIYDTKYAAEFHARFV
SEQ ID NO:6      ---------------LVFLYQNFYAHLPESLGTFTADLCEMFPAGIYDTKYAAEFHARFV
SEQ ID NO:7      ---------------LVFLYQNFYAHLPESLGTFTADLCEMFPAGIYDTKYAAEFHARFV
SEQ ID NO:8      ------------------------------------------------------------
SEQ ID NO:9      ------------------------------------------------------------
SEQ ID NO:10     ------------------------------------------------------------
SEQ ID NO:11     ------------------------------------------------------------
SEQ ID NO:12     ------------------------------------------------------------
SEQ ID NO:13     ------------------------------------------------------------
SEQ ID NO:14     ------------------------------------------------------------
SEQ ID NO:15     ------------------------------------------------------------
SEQ ID NO:16     ------------------------------------------------------------
SEQ ID NO:17     ------------------------------------------------------------
```

Figure 1 (Cont.)

```
Amino acids 241-300 (of TOE1)
TOE1
(SEQ ID NO:1)   ASYLEYAFRKCERENGKQRAAGSPHLTLEFCNYPSSMRDHIDYRCCLPPATHRPHPTSIC
SEQ ID NO:2     ASYLEYAFRKCERENGKQRAAGSPHLTLEFCNYPSSMRDHIDYRCCLPPATHRPHPTSIC
SEQ ID NO:3     ASYLEYAFRKCERENGKQRAAGSPHLTLEFCNYPSSMRDHIDYRCCLPPATHRPHPTSIC
SEQ ID NO:4     ASYLEYAFRKCERENGKQRAAGSPHLTLEFCNYPSSMRDHIDYRCCLPPATHRPHPTSIC
SEQ ID NO:5     ASYLEYAFRKCERENGKQRAAGSPHLTLEFCNYPSSMRDHIDYRCCLPPATHRPHPTSIC
SEQ ID NO:6     ASYLEYAFRKCERENGKQRAAGSPHLTLEFCNYPSSMRDHIDYRCCLPPATHRPHPTSIC
SEQ ID NO:7     ASYLEYAFRKCERENGKQRAAGSPHLTLEFCNYPSSMRDHIDYRCCLPPATHRPHPTSIC
SEQ ID NO:8     ---------------------------------------YRCCLPPATHRPHPTSIC
SEQ ID NO:9     ------------------------------------------YRCCLPPATHRPHPTSIC
SEQ ID NO:10    ---------------------------------------YRCCLPPATHRPHPTSIC
SEQ ID NO:11    ---------------------------------------YRCCLPPATHRPHPTSIC
SEQ ID NO:12    ---------------------------------------YRCCLPPATHRPHPTSIC
SEQ ID NO:13    ---------------------------------------YRCCLPPATHRPHPTSIC
SEQ ID NO:14    -----------------------------------------------------------C
SEQ ID NO:15    ------------------------------------------------------------
SEQ ID NO:16    -----------------------------------------------------------C
SEQ ID NO:17    ------------------------------------------------------------

Amino acids 301-360 (of TOE1)
TOE1
(SEQ ID NO:1)   DNFSAYGWCPLGPQCPQSHDIDLIIDTDEAAAEDKRRRRRRREKRKRALLNLPGTQTSGE
SEQ ID NO:2     DNFSAYGWCPLGPQCPQSHDIDLIIDTDEAAAEDKRRRRRRREKRKRALLNLPGTQTSGE
SEQ ID NO:3     DNFSAYGWCPLGPQCPQSHDIDLIIDTDEAAAEDKRRRRRRREKRKRALLNLPGTQTSGE
SEQ ID NO:4     DNFSAYGWCPLGPQCPQSHDIDLIIDTDEAAAEDKRRRRRRREKRKRALLNLPGTQTSGE
SEQ ID NO:5     DNFSAYGWCPLGPQCPQSHDIDLIIDTDEAAAEDKRRRRRRREKRKRALLNLPGTQTSGE
SEQ ID NO:6     DNFSAYGWCPLGPQCPQSHDIDLIIDTDEAAAEDKRRRRRRREKRKRALLNLPGTQTSGE
SEQ ID NO:7     DNFSAYGWCPLGPQCPQSHDIDLIIDTDEAAAEDKRRRRRRREKRKRALLNLPGTQTSGE
SEQ ID NO:8     DNFSAYGWCPLGPQCPQSHDIDLIIDTDEAAAEDKRRRRRRREKRKRALLNLPGTQTSGE
SEQ ID NO:9     DNFSAYGWCPLGPQCPQSHDIDLIIDTDEAAAEDKRRRRRRREKRKRALLNLPGTQTSGE
SEQ ID NO:10    DNFSAYGWCPLGPQCPQSHDIDLIIDTDEAAAEDKRRRRRRREKRKRALLNLPGTQTSGE
SEQ ID NO:11    DNFSAYGWCPLGPQCPQSHDIDLIIDTDEAAAEDKRRRRRRREKRKRALLNLPGTQTSGE
SEQ ID NO:12    DNFSAYGWCPLGPQCPQSHDIDLIIDTDEAAAEDKRRRRRRREKRKRALLNLPGTQTSGE
SEQ ID NO:13    DNFSAYGWCPLGPQCPQSHDIDLIIDTDEAAAEDKRRRRRRREKRKRALLNLPGTQTSGE
SEQ ID NO:14    DNFSAYGWCPLGPQCPQSHDIDLIIDTDEAAAEDKRRRRRRREKRKR-------------
SEQ ID NO:15    ----------------------------------KRRRRRRREKRKR-------------
SEQ ID NO:16    DNFSAYGWCPLGPQCPQSHDIDLIIDTDEAAAEDKRRRRRRREKRKRALLNLPGTQTSGE
SEQ ID NO:17    ----------------------------------KRRRRRRREKRKRALLNLPGTQTSGE
```

Figure 1 (Cont.)

```
Amino acids 361-420 (of TOE1)
TOE1
(SEQ ID NO:1)    AKDGPPKKQVCGDSIKPEETEQEVAADETRNLPHSKQGNKNDLEMGIKAARPEIADRATS
SEQ ID NO:2      AKDGPPKKQVCGDSIKPEETEQEVAADETRNLPHSKQGNKNDLEMGIKAARPEIADRATS
SEQ ID NO:3      AKDGPPKKQVCGDSIKPEETEQEVAADETRNLPHSKQGNKNDLEMGIKAARPEIAD----
SEQ ID NO:4      AKDGPPKKQVCGDSIKPEETEQEVAADETRNLPHSKQGNKND------------------
SEQ ID NO:5      AKDGPPKKQVCGDSIKPEETEQEVAAD---------------------------------
SEQ ID NO:6      AKDGPPKKQVCGD-----------------------------------------------
SEQ ID NO:7      AKD---------------------------------------------------------
SEQ ID NO:8      AKDGPPKKQVCGDSIKPEETEQEVAADETRNLPHSKQGNKNDLEMGIKAARPEIADRATS
SEQ ID NO:9      AKDGPPKKQVCGDSIKPEETEQEVAADETRNLPHSKQGNKNDLEMGIKAARPEIAD----
SEQ ID NO:10     AKDGPPKKQVCGDSIKPEETEQEVAADETRNLPHSKQGNKND------------------
SEQ ID NO:11     AKDGPPKKQVCGDSIKPEETEQEVAAD---------------------------------
SEQ ID NO:12     AKDGPPKKQVCGD-----------------------------------------------
SEQ ID NO:13     AKD---------------------------------------------------------
SEQ ID NO:14     ------------------------------------------------------------
SEQ ID NO:15     ------------------------------------------------------------
SEQ ID NO:16     AKD---------------------------------------------------------
SEQ ID NO:17     AKD---------------------------------------------------------

Amino acids 421-480 (of TOE1)
TOE1
(SEQ ID NO:1)    EVPGSQASPNPVPGDGLHRAGFDAFMTGYVMAYVEVSQGPQPCSSGPWLPECHNKVYLSG
SEQ ID NO:2      EVPGSQASPNPVPGDGLHRAGFDAFMTGYVMAYVEVSQGPQPCSSGPWLPECHNKVYLSG
SEQ ID NO:3      ------------------------------------------------------------
SEQ ID NO:4      ------------------------------------------------------------
SEQ ID NO:5      ------------------------------------------------------------
SEQ ID NO:6      ------------------------------------------------------------
SEQ ID NO:7      ------------------------------------------------------------
SEQ ID NO:8      EVPGSQASPNPVPGDGLHRAGFDAFMTGYVMAYVEVSQGPQPCSSGPWLPECHNKVYLSG
SEQ ID NO:9      ------------------------------------------------------------
SEQ ID NO:10     ------------------------------------------------------------
SEQ ID NO:11     ------------------------------------------------------------
SEQ ID NO:12     ------------------------------------------------------------
SEQ ID NO:13     ------------------------------------------------------------
SEQ ID NO:14     ------------------------------------------------------------
SEQ ID NO:15     ------------------------------------------------------------
SEQ ID NO:16     ------------------------------------------------------------
SEQ ID NO:17     ------------------------------------------------------------
```

Figure 1 (Cont.)

```
Amino acids 481-510 (of TOE1)
TOE1
(SEQ ID NO:1)    KAVPLTVAKSQFSRSSKAHNQKMKLTWGSS
SEQ ID NO:2      KAVPLTVAKSQFSRSSKAHNQKMKLTWGSS
SEQ ID NO:3      ------------------------------
SEQ ID NO:4      ------------------------------
SEQ ID NO:5      ------------------------------
SEQ ID NO:6      ------------------------------
SEQ ID NO:7      ------------------------------
SEQ ID NO:8      KAVPLTVAKSQFSRSSKAHNQKMKLTWGSS
SEQ ID NO:9      ------------------------------
SEQ ID NO:10     ------------------------------
SEQ ID NO:11     ------------------------------
SEQ ID NO:12     ------------------------------
SEQ ID NO:13     ------------------------------
SEQ ID NO:14     ------------------------------
SEQ ID NO:15     ------------------------------
SEQ ID NO:16     ------------------------------
SEQ ID NO:17     ------------------------------
```

Figure 1 (Cont.)

```
       49          57
   .....RKKRRQRRR....            Tat
    335             347
    .... KRRRRRRREKRKR..... TOE1
```

TARGET OF EGR1 (TOE1) POLYPEPTIDES FOR INHIBITION OF HIV

The present application is a U.S. national stage application of International Application No. PCT/CA2011/000234, filed Mar. 4, 2011, which in turn claims priority to Canadian Application No. 2,695,337, filed on Mar. 4, 2010, the contents of each of which are hereby incorporated by reference in their entirety.

FIELD OF INVENTION

The present invention relates to compositions and methods to treat or prevent viral infections. In particular, the invention relates to compositions and methods to treat or prevent HIV infections, as well as to modulate HIV replication.

BACKGROUND OF THE INVENTION

According to figures released by the World Health Organization in December 2008 there are approximately 33 million people worldwide that are living with HIV infection, with 2.7 million newly reported infections and 2 million deaths yearly. Furthermore, the Public Health Agency of Canada reports a steady number of newly diagnosed cases over the past 12 years (HIV and AIDS in Canada: Surveillance Report to Dec. 31, 2008, Public Health Agency of Canada, 2009), with an estimated 58,000 Canadians living with HIV/AIDS. The scope of this global pandemic underscores the need for continued research efforts to find new avenues for prevention and treatment strategies.

While there is no current vaccine available to prevent HIV infection, for infected individuals there are a variety of anti-retroviral medications available that fall into four broad categories: Reverse transcriptase (RT) inhibitors, protease inhibitors, integrase inhibitors, viral entry inhibitors, and combinations thereof known as HAART (highly active anti-retroviral therapy). While these therapies have undeniably improved the prognosis for HIV patients, there remain a number of drawbacks. These include a lack of complete viral suppression, as well as numerous, and sometimes serious, side effects (1). For these reasons intense research is focused on finding new avenues to combat the disease by developing drug-targeting strategies against key mediators of viral pathogenesis. For example, continued efforts are aimed at novel vaccine development strategies and recent attention has focused on the HIV Tat transcription factor as a drug target. This is due to its crucial role in a variety of viral functions including early RNA splicing, replication and transcription (2).

CAF and the $CD8^+$ Anti-HIV Response

Upon infection with the HIV virus the host immune response is activated in an attempt to combat the infection and prevent the progression to AIDS. $CD8^+$ T cells perform a crucial part of the host anti-HIV response in different ways. First, $CD8^+$ cells from HIV infected individuals can recognize infected cells and respond by killing the cells lytically (CTL response). Typically, this response occurs during the initial phase of infection where a transient decrease in viremia can be seen. Also during the acute phase of infection, prior to antibody production, a further action of $CD8^+$ T cells involves an innate, non-cytotoxic action, which results in a decrease of viral replication. This latter response is known as the $CD8^+$ cell non-cytotoxic anti-HIV response (CNAR), and functions in a non-MHC restricted fashion (3, 4). While both of these activities are significant, the CNAR activity is of particular interest as it correlates with clinical status (5, 6). Specifically, long term HIV non-progressors, represented by infected but asymptomatic individuals who remain healthy without ever receiving anti-viral medication, display a heightened CNAR activity as compared to patients who display disease progression (7, 8).

CNAR is active against a wide variety of HIV strains and is able to suppress HIV replication in both $CD4^+$ T cells as well as macrophages (9). Since its discovery in 1986, there has been keen interest by many research groups in understanding the molecular mechanism by which CNAR functions, however this remains incompletely understood. Several important studies have contributed to a partial characterization of CNAR.

It has been known for some time that the anti-HIV activity of CNAR results from the secretion of a proteinacious factor(s) from activated $CD8^+$ T cells, and has been termed CAF for $CD8^+$ anti-HIV factor (10). Interestingly, it has been shown that the secretion of an active HIV inhibitory CAF factor(s) is not limited to $CD8^+$ T cells from HIV seropositive patients, but can also be detected in culture media from EBV specific T cell line (11). This result suggests that there may be a common or related CAF that could function to inhibit viral replication as a result of immune system activation.

Although several groups have identified proteins that display anti-HIV activity, none of these fulfill all the criteria that CAF is known to exhibit. Some examples of anti-HIV factors include alpha defensin, RANTES and other beta chemokines, the cell adhesion molecule VCAM, and bovine antithrombin III (12-15).

While the precise identity of CAF remains unknown, research by many groups has combined to reveal certain key features. Together with secretion from activated $CD8^+$ T cells, studies have suggested that a proteolytic activity appears to be necessary for CAF activation since protease inhibitors can block CAF activity (16). To date, the responsible protease involved has not been identified. Mechanistically, it is known that CAF or a CAF-like activity can suppress viral replication by inhibiting HIV transcription driven by the viral LTR, but does not appear to function through inhibiting viral integration or reverse transcription (17-19). Further evidence suggests that the inhibition of viral transcription occurs via activation of the STAT1 signaling pathway (20). Given the observation that CAF activity functions through inhibition of viral LTR driven transcription, a mutational analysis of several transcription factor binding sites in the LTR has been performed (21). The results of this study indicate that CAF does not appear to rely on independent binding of NFAT, AP1, NF-κB or SP1 sites. With respect to viral transactivators, it is known that the HIV Tat transcription factor plays an essential role in viral replication through its interaction with the Tat transactivation response region (TAR). The TAR element is present both within the LTR as well as at the 5' end of all viral transcripts where Tat interacts to activate transcription and promote efficient mRNA translation (22). The importance of the Tat/TAR system is highlighted by studies showing that impairing this interaction can dramatically inhibit HIV replication (23). The Tat/TAR system, perhaps together with other factors, is therefore a possible target for the effects of CAF.

Despite years of ongoing research in this area, there continues to be a need for new and improved medicines for treating and/or preventing HIV and AIDS. The present inventors have accordingly sought to identify new diagnostic and chemotherapeutic methods in this area by investigating the Tat/TAR system and potential CAF targets.

SUMMARY OF THE INVENTION

The present invention accordingly relates to compositions and methods for prevention and/or treatment of HIV infections, as well as compositions and methods to modulate HIV replication.

According to the present invention there is provided a polypeptide, protein or functional fragment thereof comprising an amino acid sequence that is between about 80% and about 100% identical to any one of the sequences of SEQ ID NO:1; SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16 or SEQ ID NO:17, or which comprises an amino acid sequence that is between about 80% and about 100% identical to the sequence of a deletion mutant of TOE1 (target for EGR1 (early growth response gene)) including K335/D373 (SEQ ID NO:21); K335/D387 (SEQ ID NO:22); K335/D402 (SEQ ID NO:23); K335/D416 (SEQ ID NO:24); K335/D435 (SEQ ID NO:25); K335/D443 (SEQ ID NO:26); K335/S510 (SEQ ID NO:27); E329/D363 (SEQ ID NO:28); E329/D373 (SEQ ID NO:29); E329/D387 (SEQ ID NO:30); E329/D402 (SEQ ID NO:31); E329/D416 (SEQ ID NO:32); E329/D435 (SEQ ID NO:33); E329/D443 (SEQ ID NO:34); E329/S510 (SEQ ID NO:35); L323/D363 (SEQ ID NO:36); L323/D373 (SEQ ID NO:37); L323/D387 (SEQ ID NO:38); L323/D402 (SEQ ID NO:39); L323/D416 (SEQ ID NO:40); L323/D435 (SEQ ID NO:41); L323/D443 (SEQ ID NO:42); L323/S510 (SEQ ID NO:43); I321/D363 (SEQ ID NO:44); I321/D373 (SEQ ID NO:45); I321/D387 (SEQ ID NO:46); I321/D402 (SEQ ID NO:47); I321/D416 (SEQ ID NO:48); I321/D435 (SEQ ID NO:49); I321/D443 (SEQ ID NO:50); 1321/S510 (SEQ ID NO:51); N302/D363 (SEQ ID NO:52); N302/D373 (SEQ ID NO:53); N302/D387 (SEQ ID NO:54); N302/D402 (SEQ ID NO:55); N302/D416 (SEQ ID NO:56); N302/D435 (SEQ ID NO:57); N302/D443 (SEQ ID NO:58); N302/S510 (SEQ ID NO:59); Y283/D435 (SEQ ID NO:60); Y283/D443 (SEQ ID NO:61); H280/D363 (SEQ ID NO:62); H280/D373 (SEQ ID NO:63); H280/D387 (SEQ ID NO:64); H280/D402 (SEQ ID NO:65); H280/D416 (SEQ ID NO:66); H280/D435 (SEQ ID NO:67); H280/D443 (SEQ ID NO:68); H280/S510 (SEQ ID NO:69); T229/D363 (SEQ ID NO:70); T229/D373 (SEQ ID NO:71); T229/D387 (SEQ ID NO:72); T229/D402 (SEQ ID NO:73); T229/D416 (SEQ ID NO:74); T229/D435 (SEQ ID NO:75); T229/D443 (SEQ ID NO:76); T229/S510 (SEQ ID NO:77); L218/D363 (SEQ ID NO:78); L218/D373 (SEQ ID NO:79); L218/D387 (SEQ ID NO:80); L218/D402 (SEQ ID NO:81); L218/D416 (SEQ ID NO:82); L218/D435 (SEQ ID NO:83); L218/D443 (SEQ ID NO:84); L218/S510 (SEQ ID NO:85); L196/D435 (SEQ ID NO:86); L196/D443 (SEQ ID NO:87); K111/D363 (SEQ ID NO:88); K111/D373 (SEQ ID NO:89); K111/D387 (SEQ ID NO:90); K111/D402 (SEQ ID NO:91); K111/D416 (SEQ ID NO:92); K111/D435 (SEQ ID NO:93); K111/D443 (SEQ ID NO:94); K111/S510 (SEQ ID NO:95); T65/D363 (SEQ ID NO:96); T65/D373 (SEQ ID NO:97); T65/D387 (SEQ ID NO:98); T65/D402 (SEQ ID NO:99); T65/D416 (SEQ ID NO:100); T65/D435 (SEQ ID NO:101); T65/D443 (SEQ ID NO:102); T65/S510 (SEQ ID NO:103); G18/D363 (SEQ ID NO:104); G18/D373 (SEQ ID NO:105); G18/D387 (SEQ ID NO:106); G18/D402 (SEQ ID NO:107); G18/D416 (SEQ ID NO:108); G18/D435 (SEQ ID NO:109); G18/D443 (SEQ ID NO:110); G18/S510 (SEQ ID NO:111); G8/D363 (SEQ ID NO:112); G8/D373 (SEQ ID NO:113); G8/D387 (SEQ ID NO:114); G8/D402 (SEQ ID NO:115); G8/D416 (SEQ ID NO:116); G8/D435 (SEQ ID NO:117); G8/D443 (SEQ ID NO:118); G8/S510 (SEQ ID NO:119); S5/D363 (SEQ ID NO:120); S5/D373 (SEQ ID NO:121); S5/D387 (SEQ ID NO:122); S5/D402 (SEQ ID NO:123); S5/D416 (SEQ ID NO:124); S5/D435 (SEQ ID NO:125); S5/D443 (SEQ ID NO:126); and S5/S510 (SEQ ID NO:127), wherein the indicated amino acids respectively specify the amino- and carboxy-terminal residues of the deletion mutants based on the sequence of SEQ ID NO:1, including fragments and variants thereof. In a further embodiment, the amino acid sequence is identical to the sequence of SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16 or SEQ ID NO:17, or to the to the sequence of the following TOE1 mutants: K335/D373 (SEQ ID NO:21); K335/D387 (SEQ ID NO:22); K335/D402 (SEQ ID NO:23); K335/D416 (SEQ ID NO:24); K335/D435 (SEQ ID NO:25); K335/D443 (SEQ ID NO:26); K335/S510 (SEQ ID NO:27); E329/D363 (SEQ ID NO:28); E329/D373 (SEQ ID NO:29); E329/D387 (SEQ ID NO:30); E329/D402 (SEQ ID NO:31); E329/D416 (SEQ ID NO:32); E329/D435 (SEQ ID NO:33); E329/D443 (SEQ ID NO:34); E329/S510 (SEQ ID NO:35); L323/D363 (SEQ ID NO:36); L323/D373 (SEQ ID NO:37); L323/D387 (SEQ ID NO:38); L323/D402 (SEQ ID NO:39); L323/D416 (SEQ ID NO:40); L323/D435 (SEQ ID NO:41); L323/D443 (SEQ ID NO:42); L323/S510 (SEQ ID NO:43); I321/D363 (SEQ ID NO:44); I321/D373 (SEQ ID NO:45); I321/D387 (SEQ ID NO:46); I321/D402 (SEQ ID NO:47); I321/D416 (SEQ ID NO:48); I321/D435 (SEQ ID NO:49); I321/D443 (SEQ ID NO:50); I321/S510 (SEQ ID NO:51); N302/D363 (SEQ ID NO:52); N302/D373 (SEQ ID NO:53); N302/D387 (SEQ ID NO:54); N302/D402 (SEQ ID NO:55); N302/D416 (SEQ ID NO:56); N302/D435 (SEQ ID NO:57); N302/D443 (SEQ ID NO:58); N302/S510 (SEQ ID NO:59); Y283/D435 (SEQ ID NO:60); Y283/D443 (SEQ ID NO:61); H280/D363 (SEQ ID NO:62); H280/D373 (SEQ ID NO:63); H280/D387 (SEQ ID NO:64); H280/D402 (SEQ ID NO:65); H280/D416 (SEQ ID NO:66); H280/D435 (SEQ ID NO:67); H280/D443 (SEQ ID NO:68); H280/S510 (SEQ ID NO:69); T229/D363 (SEQ ID NO:70); T229/D373 (SEQ ID NO:71); T229/D387 (SEQ ID NO:72); T229/D402 (SEQ ID NO:73); T229/D416 (SEQ ID NO:74); T229/D435 (SEQ ID NO:75); T229/D443 (SEQ ID NO:76); T229/S510 (SEQ ID NO:77); L218/D363 (SEQ ID NO:78); L218/D373 (SEQ ID NO:79); L218/D387 (SEQ ID NO:80); L218/D402 (SEQ ID NO:81); L218/D416 (SEQ ID NO:82); L218/D435 (SEQ ID NO:83); L218/D443 (SEQ ID NO:84); L218/S510 (SEQ ID NO:85); L196/D435 (SEQ ID NO:86); L196/D443 (SEQ ID NO:87); K111/D363 (SEQ ID NO:88); K111/D373 (SEQ ID NO:89); K111/D387 (SEQ ID NO:90); K111/D402 (SEQ ID NO:91); K111/D416 (SEQ ID NO:92); K111/D435 (SEQ ID NO:93); K111/D443 (SEQ ID NO:94); K111/S510 (SEQ ID NO:95); T65/D363 (SEQ ID NO:96); T65/D373 (SEQ ID NO:97); T65/D387 (SEQ ID NO:98); T65/D402 (SEQ ID NO:99); T65/D416 (SEQ ID NO:100); T65/D435 (SEQ ID NO:101); T65/D443 (SEQ ID NO:102); T65/S510 (SEQ ID NO:103); G18/D363 (SEQ ID NO:104); G18/D373 (SEQ ID NO:105); G18/D387 (SEQ ID NO:106); G18/D402 (SEQ ID NO:107); G18/D416 (SEQ ID NO:108); G18/D435 (SEQ ID NO:109); G18/D443 (SEQ ID NO:110); G18/S510 (SEQ ID NO:111); G8/D363 (SEQ ID NO:112); G8/D373 (SEQ ID NO:113); G8/D387 (SEQ ID NO:114); G8/D402 (SEQ ID NO:115); G8/D416 (SEQ ID NO:116); G8/D435 (SEQ ID NO:117); G8/D443 (SEQ ID NO:118); G8/S510 (SEQ ID NO:119); S5/D363 (SEQ ID NO:120); S5/D373 (SEQ ID NO:121); S5/D387 (SEQ ID NO:122); S5/D402 (SEQ ID NO:123); S5/D416 (SEQ ID NO:124); S5/D435 (SEQ ID NO:125); S5/D443

(SEQ ID NO:126); and S5/S510 (SEQ ID NO:127), wherein the indicated amino acids are as described above.

Polypeptides as described herein will preferably involve purified or isolated polypeptide preparations. In certain embodiments, purification of the polypeptide may utilize recombinant expression methods well known in the art, and may involve the incorporation of an affinity tag into the expression construct to allow for affinity purification of the target polypeptide.

In addition, polypeptides as referred to herein may also be produced by synthetic preparative methods, for example but not limited to solid-phase synthetic processes.

Fragments of the above polypeptides are included herein, but are not limited to amino acid sequences wherein one or more amino acids are deleted. For example, but not to be considered limiting, a fragment may exist when one or more amino acids from the amino terminal, carboxy terminal or both are removed. Further, one or more amino acids internal to the polypeptide may be deleted.

Variants of the above polypeptides are also contemplated, and may comprise one or more amino acid substitutions, additions, insertions, or a combination thereof in the sequences shown herein. Preferably, the amino acid sequence exhibits greater than about 90% homology, more preferably greater than about 91%, 92%, 93%, 94%, 95%, 96%, 97%, 98%, 99% or about 100% homology to the sequence(s) described herein. The degree of homology may also be represented by a range defined by any two of the values listed above or any value therein between.

Amino acid substitutions, in a non-limiting embodiment, may include conservative amino acid substitutions. Conservative substitutions may mean substitutions with similarly charged amino acid residues or residues with similar polar properties. As an example, lysine (K) may be replaced with arginine (R), aspartic acid (D) may be replaced with glutamic acid (E). Other conservative amino acid replacements will be apparent to those skilled in the art.

Polypeptide variants as described herein may also refer to peptides having at least one modification. For instance, but not to be limiting, the modification may be carried out in a synthetic process such as cyclization, N terminus modification, C terminus modification, peptide bond modification including, but not limited to, $CH_2$—NH, $CH_2$—S, $CH_2$—S—O, O=C—NH $CH_2$-0, $CH_2$—$CH_2$, S=C—NH, CH=CH or CF=CH, backbone modification and residue modification. In other embodiments, polypeptide variants may encompass polypeptides prepared by recombinant means, and which are post-translationally modified. Methods for preparing such variants are well known in the art.

It is further contemplated that the amino acid sequence comprises greater than about 70%, more preferably about 80%, 85%, 90%, 91%, 92%, 93%, 94%, 95%, 96%, 97%, 98%, 99% or about 100% identity with the amino acid sequence(s) described herein. Further, the degree of identity may be represented by a range defined by any two of the values listed or any value therein between. Methods for determining % identity or % homology are known in the art and any suitable method may be employed for this purpose.

It is also envisioned that the above-described polypeptides, fragments and variants can be linked to a heterologous carrier molecule. In certain non-limiting embodiments, the heterologous carrier molecule may comprise a protein transduction domain. For example, yet without wishing to be limiting in any manner, the protein transduction domain may comprise the amino acid sequence of Tat (SEQ ID NO:18), or may comprise lipids or other chemical groups to induce cell permeability.

There is further provided an isolated polynucleotide which encodes the above-described polypeptide, protein or functional fragment thereof. Embodiments of such polynucleotides can be derived from the wild-type nucleotide sequence of TOE1, or may be obtained through reverse translation of the polypeptide sequences described herein.

The nucleotide sequences provided by the present invention may be part of a larger nucleotide sequence or nucleotide construct optionally comprising one or more regulatory sequences, for example promoters, terminators and the like. By the terms "regulatory sequence", "regulatory region", "regulatory element" it is meant a portion of nucleic acid typically, but not always, upstream of the protein or polypeptide coding region of a nucleotide sequence, which may be comprised of either DNA or RNA, or both DNA and RNA. When a regulatory region is active, and in operative association with a nucleotide sequence of interest, this may result in expression of the nucleotide sequence of interest. A regulatory element may be capable of mediating organ specificity, or controlling developmental or temporal nucleotide sequence activation. A "regulatory region" includes promoter elements, core promoter elements exhibiting a basal promoter activity, elements that are inducible in response to a stimulus, elements that mediate promoter activity such as negative regulatory elements or transcriptional enhancers. "Regulatory region", as used herein, also includes elements that are active following transcription, for example, regulatory elements that modulate nucleotide sequence expression such as translational and transcriptional enhancers, translational and transcriptional repressors, upstream activating sequences, and mRNA instability determinants. Several of these latter elements may be located proximal to the coding region.

In further embodiments there are provided vectors comprising the above-described polynucleotides. The vector may be a plasmid, a cosmid, a phage, a virus, or a fragment of a virus. The vector can be an expression vector.

There is further provided a cell comprising a polynucleotide or vector as described above, as well as compositions comprising the polypeptide, polynucleotide or vector and a suitable carrier.

The above composition may, in an embodiment, be a pharmaceutical composition for treatment or prevention of HIV infection, or for modulating HIV replication, inhibiting HIV viral transcription, inhibiting the viral Tat protein, or inhibiting HIV LTR expression.

The above polypeptides and polynucleotides can be used in a method for treatment or prevention of human immunodeficiency virus (HIV) infection, for example by administering a polypeptide or composition as described herein to a subject in need of such treatment.

The above polypeptides and polynucleotides can also be used in a method to modulate the replication of HIV, inhibit viral transcription, inhibit the viral Tat protein, or inhibit HIV LTR expression. In certain embodiments the modulating of HIV replication comprises inhibiting of HIV replication. In addition, the modulating of HIV replication, inhibiting of HIV viral transcription, inhibiting of the viral Tat protein, or inhibiting of HIV LTR expression can be carried out either in vitro or in vivo.

In certain embodiments the human immunodeficiency virus is HIV-1 or HIV-2, or both.

A subject in the method(s) described herein may be a mammalian subject, for example, but not limited to mouse, cow, sheep, goat, pig, dog, cat, rat, rabbit, primate, or human. In an embodiment, which is not meant to be limiting, the subject is a human.

Also provided herein is a protein transduction domain comprising an amino acid sequence that is between about 80% and about 100% identical to the sequence of SEQ ID NO:15, or a fragment or variant thereof. In addition, there is provided an isolated nucleic acid encoding such a protein transduction domain, a vector comprising the nucleic acid encoding the protein transduction domain, a host cell transformed with the nucleic acid or vector encoding the protein transduction domain, or a composition comprising a therapeutically active molecule linked to the protein transduction domain. The therapeutically active molecule may be any molecule that has biological activity, such as but not limited to polypeptides, nucleic acids, organic compounds, and others as will be apparent to those skilled in the art.

In further embodiments, there is also provided an antibody which binds to the polypeptide described above, and in preferred embodiments, a polypeptide having the amino acid sequence of SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16 or SEQ ID NO:17, or a fragment or variant thereof. The antibody may be, without intending to be limiting, either a monoclonal antibody or a polyclonal antibody. Such antibodies can be prepared using common techniques as will be apparent to those skilled in the art.

Those skilled in the art will recognize, or be able to ascertain using no more than routine experimentation, numerous equivalents to the specific products and procedures described herein. Such equivalents are considered to be within the scope of this invention and are covered by the following claims.

BRIEF DESCRIPTION OF THE DRAWINGS

These and other features of the invention will become more apparent from the following description in which reference is made to the following figures:

FIG. 1: Multiple sequence alignment of the sequences of human TOE1 (SEQ ID NO: 1) with the amino acid sequences of deletion mutant L196 (SEQ ID NO:2), deletion mutant L196/D416 (SEQ ID NO:3), deletion mutant L196/D402 (SEQ ID NO:4), deletion mutant L196/D387 (SEQ ID NO:5), deletion mutant L196/D373 (SEQ ID NO:6), deletion mutant L196/D363 (SEQ ID NO:7), deletion mutant Y283 (SEQ ID NO:8), deletion mutant Y283/D416 (SEQ ID NO:9), deletion mutant Y283/D402 (SEQ ID NO:10), deletion mutant Y283/D387 (SEQ ID NO:11), deletion mutant Y283/D373 (SEQ ID NO:12), deletion mutant Y283/D363 (SEQ ID NO:13), deletion mutant C300/R347 (SEQ ID NO:14), deletion mutant K335/R347 (SEQ ID NO:15), deletion mutant C300/D363 (SEQ ID NO:16) and deletion mutant K335/D363 (SEQ ID NO:17).

Figure 9:
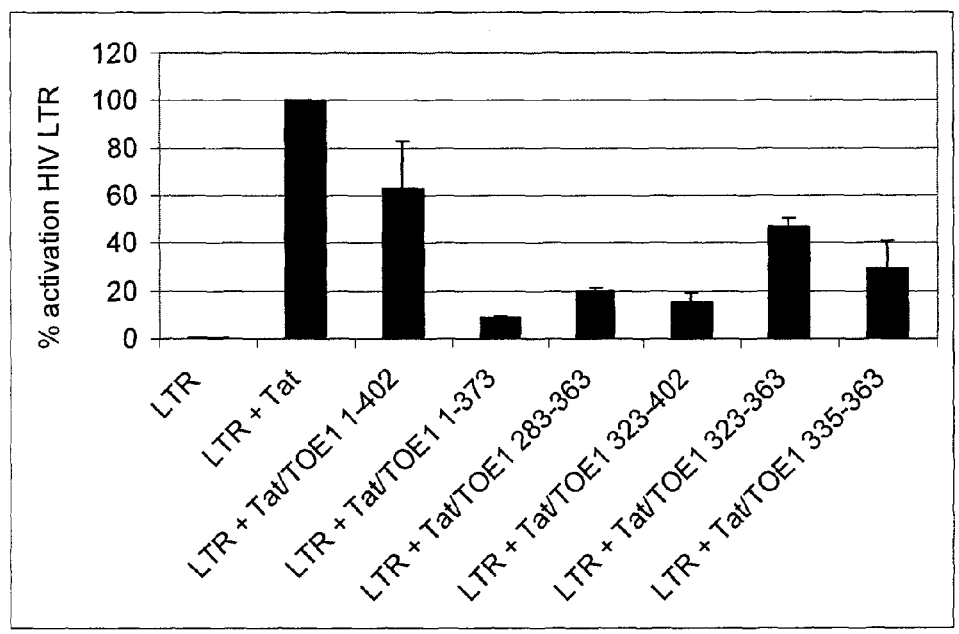

FIG. 9: Defining the minimal TOE1 region able to inhibit Tat-induced HIV LTR activation. The indicated TOE1 deletion mutants were transfected as described herein and demonstrate an inhibition of Tat-induced activation of the HIV LTR. Results are expressed as percentage activation of the HIV LTR referenced to Tat. All transfections and measurements were performed in triplicate, and results are representative of multiple independent experiments.

Figure 10:
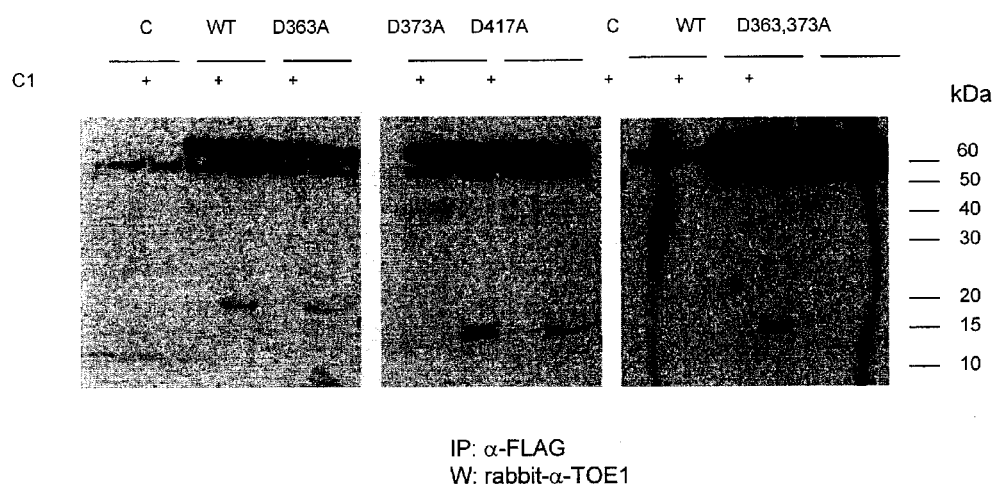

FIG. 10: Identification of caspase-1 cleavage sites at TOE1 amino acids 363 and 373. Mutant constructs D363A and D373A of N-terminal FLAG tagged TOE1 were generated by QuikChange™ (Stratagene) and then transfected into 293T cells. Cell lysates were immunoprecipitated using the α-FLAG antibody and caspase-1 incubation was carried out as described for FIG. 4. Results indicate that caspase-1 cleaves TOE1 at residues 363 and 373 as evidenced by the lack of a 17 kDa fragment in the TOE1 mutants containing an alanine at residues 363 and 373.

Figure 11:
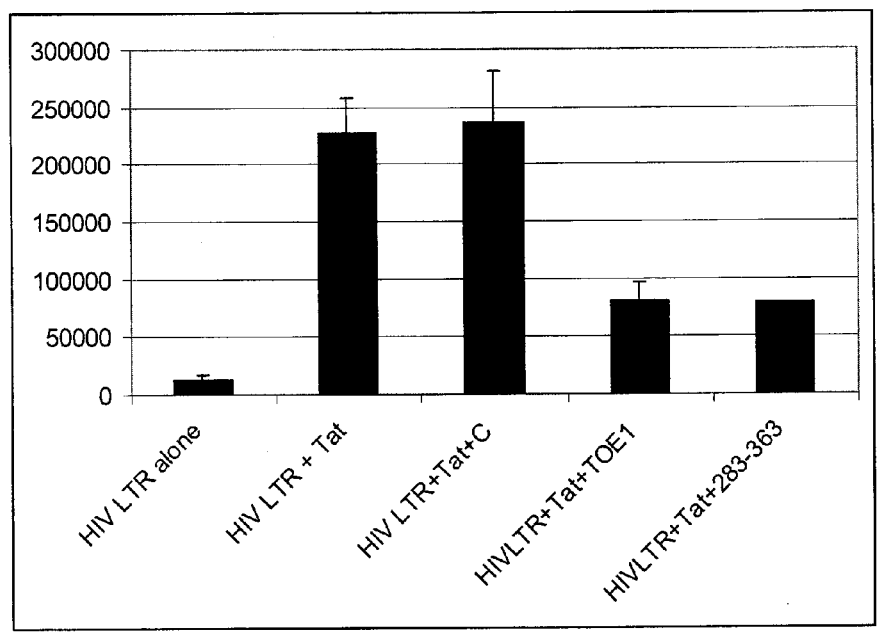

FIG. 11. TOE1 can be secreted and inhibits HIV LTR in neighboring cells. HeLa cells were transfected with either HIV LTR alone, or together with Tat as indicated. Separately, 293T cells were transfected with either control empty vector (C), full length TOE1 (TOE1), or a deletion mutant comprising amino acids 283-363 (SEQ ID NO:13) containing the basic region located at 335-348 (283-363). 24 hours following transfection, the transfected 293T cells were placed in co-culture with the transfected HeLa cells to provide the samples. 24 hours after co-culture, samples were assayed for Tat-driven HIV LTR activity. Results indicate that a TOE1 fragment comprising the basic region was capable of being secreted from transfected cells and entering and inhibiting Tat activation of the HIV LTR in neighboring cells.

DETAILED DESCRIPTION

The present invention provides a polypeptide comprising an amino acid sequence that is at least 80% identical to the sequence of TOE1 (SEQ ID NO: 1) or deletion mutants thereof including L196 (SEQ ID NO:2), L196/D416 (SEQ ID NO:3), L196/D402 (SEQ ID NO:4), L196/D387 (SEQ ID NO:5), L196/D373 (SEQ ID NO:6), L196/D363 (SEQ ID NO:7), Y283 (SEQ ID NO:8), Y283/D416 (SEQ ID NO:9), Y283/D402 (SEQ ID NO:10), Y283/D387 (SEQ ID NO:11), Y283/D373 (SEQ ID NO:12), Y283/D363 (SEQ ID NO:13), C300/R347 (SEQ ID NO:14), K335/R347 (SEQ ID NO:15), C300/D363 (SEQ ID NO:16) and K335/D363 (SEQ ID NO:17), or a fragment or variant of any one thereof. An alignment of the above-specified sequences can be seen in FIG. 1. The alignment is provided in CLUSTAL W (1.83) format.

The invention also provides a polypeptide comprising an amino acid sequence that is at least 80% identical to one of the following additional deletion mutants of TOE1: K335/D363 (SEQ ID NO:17); K335/D373 (SEQ ID NO:21); K335/D387 (SEQ ID NO:22); K335/D402 (SEQ ID NO:23); K335/D416 (SEQ ID NO:24); K335/D435 (SEQ ID NO:25); K335/D443 (SEQ ID NO:26); K335/S510 (SEQ ID NO:27); E329/D363 (SEQ ID NO:28); E329/D373 (SEQ ID NO:29); E329/D387 (SEQ ID NO:30); E329/D402 (SEQ ID NO:31); E329/D416 (SEQ ID NO:32); E329/D435 (SEQ ID NO:33); E329/D443 (SEQ ID NO:34); E329/S510 (SEQ ID NO:35); L323/D363 (SEQ ID NO:36); L323/D373 (SEQ ID NO:37); L323/D387 (SEQ ID NO:38); L323/D402 (SEQ ID NO:39); L323/D416 (SEQ ID NO:40); L323/D435 (SEQ ID NO:41); L323/D443 (SEQ ID NO:42); L323/S510 (SEQ ID NO:43); I321/D363 (SEQ ID NO:44); I321/D373 (SEQ ID NO:45); I321/D387 (SEQ ID NO:46); I321/D402 (SEQ ID NO:47); I321/D416 (SEQ ID NO:48); I321/D435 (SEQ ID NO:49); I321/D443 (SEQ ID NO:50); I321/S510 (SEQ ID NO:51); N302/D363 (SEQ ID NO:52); N302/D373 (SEQ ID NO:53); N302/D387 (SEQ ID NO:54); N302/D402 (SEQ ID NO:55); N302/D416 (SEQ ID NO:56); N302/D435 (SEQ ID NO:57); N302/D443 (SEQ ID NO:58); N302/S510 (SEQ ID NO:59); Y283/D435 (SEQ ID NO:60); Y283/D443 (SEQ ID NO:61); H280/D363 (SEQ ID NO:62); H280/D373 (SEQ ID NO:63); H280/D387 (SEQ ID NO:64); H280/D402 (SEQ ID NO:65); H280/D416 (SEQ ID NO:66); H280/D435 (SEQ ID NO:67); H280/D443 (SEQ ID NO:68); H280/S510 (SEQ ID NO:69); T229/D363 (SEQ ID NO:70); T229/D373 (SEQ ID NO:71); T229/D387 (SEQ ID NO:72); T229/D402 (SEQ ID NO:73); T229/D416 (SEQ ID NO:74); T229/D435 (SEQ ID NO:75); T229/D443 (SEQ ID NO:76); T229/S510 (SEQ ID NO:77); L218/D363 (SEQ ID NO:78); L218/D373 (SEQ ID NO:79); L218/D387 (SEQ ID NO:80); L218/D402 (SEQ ID NO:81); L218/D416 (SEQ ID NO:82); L218/D435 (SEQ ID NO:83); L218/D443 (SEQ ID NO:84); L218/S510 (SEQ ID NO:85); L196/D435 (SEQ ID NO:86); L196/D443 (SEQ ID NO:87); K111/D363 (SEQ ID NO:88); K111/D373 (SEQ ID NO:89); K111/D387 (SEQ ID NO:90); K111/D402 (SEQ ID NO:91); K111/D416 (SEQ ID NO:92); K111/D435 (SEQ ID NO:93); K111/D443 (SEQ ID NO:94); K111/S510 (SEQ ID NO:95); T65/D363 (SEQ ID NO:96); T65/D373 (SEQ ID NO:97); T65/D387 (SEQ ID NO:98); T65/D402 (SEQ ID NO:99); T65/D416 (SEQ ID NO:100); T65/D435 (SEQ ID NO:101); T65/D443 (SEQ ID NO:102); T65/S510 (SEQ ID NO:103); G18/D363 (SEQ ID NO:104); G18/D373 (SEQ ID NO:105); G18/D387 (SEQ ID NO:106); G18/D402 (SEQ ID NO:107); G18/D416 (SEQ ID NO:108); G18/D435 (SEQ ID NO:109); G18/D443 (SEQ ID NO:110); G18/S510 (SEQ ID NO:111); G8/D363 (SEQ ID NO:112); G8/D373 (SEQ ID NO:113); G8/D387 (SEQ ID NO:114); G8/D402 (SEQ ID NO:115); G8/D416 (SEQ ID NO:116); G8/D435 (SEQ ID NO:117); G8/D443 (SEQ ID NO:118); G8/S510 (SEQ ID NO:119); S5/D363 (SEQ ID NO:120); S5/D373 (SEQ ID NO:121); S5/D387 (SEQ ID NO:122); S5/D402 (SEQ ID NO:123); S5/D416 (SEQ ID NO:124); S5/D435 (SEQ ID NO:125); S5/D443 (SEQ ID NO:126); and S5/S510 (SEQ ID NO:127), or a fragment or variant of any one thereof. The indicated amino acids respectively specify the amino- and carboxy-terminal residues of the deletion mutants as derived from the TOE1 sequence (SEQ ID NO:1).

In a preferred embodiment, the polypeptide is between about 15 and about 510 amino acids, for example, but not limited to 15, 17, 19, 20, 25, 30, 35, 40, 45, 50, 55, 60, 65, 70, 75, 80, 90, 100, 125, 150, 175, 200, 225, 250, 275, 300, 325, 350, 375, 400, 425, 450, 475, 500 or 510 amino acids. However, the polypeptide length may also be defined by a range of any two of the values listed above. In addition, in an alternate embodiment, which is not meant to be limiting in any manner, the present invention contemplates polypeptides as defined above which comprises more than 510 amino acids.

A polypeptide may be of any length unless otherwise specified. A fragment is any polypeptide or nucleic acid that is shorter than its corresponding naturally occurring polypeptide or nucleic acid, respectively. A derivative is any polypeptide or nucleic acid that is altered with respect to a reference polypeptide or nucleic acid, respectively, and includes, for example fragments or mutants.

The present invention also contemplates polypeptides having an amino acid sequence that comprises 80%, 81%, 82%, 83%, 84%, 85%, 86%, 87%, 88%, 89%, 90%, 91%, 92%, 93%, 94%, 95%, 96%, 97%, 98%, 99% or 100% identity to the amino sequences described above. Further, the polypeptides may be defined as comprising a range of sequence identity defined by any two of the values listed above.

The present invention also provides a nucleic acid encoding polypeptides as defined above. For example, but not wishing to be limiting in any manner, the present invention contemplates a nucleic acid that encodes an amino acid sequence that is at least 80% identical to the sequence of SEQ ID NO:1; SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16 or SEQ ID NO:17, or the K335/D373 (SEQ ID NO:21); K335/D387 (SEQ ID NO:22); K335/D402 (SEQ ID NO:23); K335/D416 (SEQ ID NO:24); K335/D435 (SEQ ID NO:25); K335/D443 (SEQ ID NO:26); K335/S510 (SEQ ID NO:27); E329/D363 (SEQ ID NO:28); E329/D373 (SEQ ID NO:29); E329/D387 (SEQ ID NO:30); E329/D402 (SEQ ID NO:31); E329/D416 (SEQ ID NO:32); E329/D435 (SEQ ID NO:33); E329/D443 (SEQ ID NO:34); E329/S510 (SEQ ID NO:35); L323/D363 (SEQ ID NO:36); L323/D373 (SEQ ID NO:37); L323/D387 (SEQ ID NO:38); L323/D402 (SEQ ID NO:39); L323/D416 (SEQ ID NO:40); L323/D435 (SEQ ID NO:41); L323/D443 (SEQ ID NO:42); L323/S510 (SEQ ID NO:43); I321/D363 (SEQ ID NO:44); I321/D373 (SEQ ID NO:45); I321/D387 (SEQ ID NO:46); I321/D402 (SEQ ID NO:47); I321/D416 (SEQ ID NO:48); I321/D435 (SEQ ID NO:49); I321/D443 (SEQ ID NO:50); I321/S510 (SEQ ID NO:51); N302/D363 (SEQ ID NO:52); N302/D373 (SEQ ID NO:53); N302/D387 (SEQ ID NO:54); N302/D402 (SEQ ID NO:55); N302/D416 (SEQ ID NO:56); N302/D435 (SEQ ID NO:57); N302/D443 (SEQ ID NO:58); N302/S510 (SEQ ID NO:59); Y283/D435 (SEQ ID NO:60); Y283/D443 (SEQ ID NO:61); H280/D363 (SEQ ID NO:62); H280/D373 (SEQ ID NO:63); H280/D387 (SEQ ID NO:64); H280/D402 (SEQ ID NO:65); H280/D416 (SEQ ID NO:66); H280/D435 (SEQ ID NO:67); H280/D443 (SEQ ID NO:68); H280/S510 (SEQ ID NO:69); T229/D363 (SEQ ID NO:70); T229/D373 (SEQ ID NO:71); T229/D387 (SEQ ID NO:72); T229/D402 (SEQ ID NO:73); T229/D416 (SEQ ID NO:74); T229/D435 (SEQ ID NO:75); T229/D443 (SEQ ID NO:76); T229/S510 (SEQ ID NO:77); L218/D363 (SEQ ID NO:78); L218/D373 (SEQ ID NO:79); L218/D387 (SEQ ID NO:80); L218/D402 (SEQ ID NO:81); L218/D416 (SEQ ID NO:82); L218/D435 (SEQ ID NO:83); L218/D443 (SEQ ID NO:84); L218/S510 (SEQ ID NO:85); L196/D435 (SEQ ID NO:86); L196/D443 (SEQ ID NO:87); K111/D363 (SEQ ID NO:88); K111/D373 (SEQ ID NO:89); K111/D387 (SEQ ID NO:90); K111/D402 (SEQ ID NO:91); K111/D416 (SEQ ID NO:92); K111/D435 (SEQ ID NO:93); K111/D443 (SEQ ID NO:94); K111/S510 (SEQ ID NO:95); T65/D363 (SEQ ID NO:96); T65/D373 (SEQ ID NO:97); T65/D387 (SEQ ID NO:98); T65/D402 (SEQ ID NO:99); T65/D416 (SEQ ID NO:100); T65/D435 (SEQ ID NO:101); T65/D443 (SEQ ID NO:102); T65/S510 (SEQ ID NO:103); G18/D363 (SEQ ID NO:104); G18/D373 (SEQ ID NO:105); G18/D387 (SEQ ID NO:106); G18/D402 (SEQ ID NO:107); G18/D416 (SEQ ID NO:108); G18/D435 (SEQ ID NO:109); G18/D443 (SEQ ID NO:110); G18/S510 (SEQ ID NO:111); G8/D363 (SEQ ID NO:112); G8/D373 (SEQ ID NO:113); G8/D387 (SEQ ID NO:114); G8/D402 (SEQ ID NO:115); G8/D416 (SEQ ID NO:116); G8/D435 (SEQ ID NO:117); G8/D443 (SEQ ID NO:118); G8/S510 (SEQ ID NO:119); S5/D363 (SEQ ID NO:120); S5/D373 (SEQ ID NO:121); S5/D387 (SEQ ID NO:122); S5/D402 (SEQ ID NO:123); S5/D416 (SEQ ID NO:124); S5/D435 (SEQ ID NO:125); S5/D443 (SEQ ID NO:126); and S5/S510 (SEQ ID NO:127) deletion mutants of TOE1 described above, or a fragment or variant of any one thereof.

By "percent identical" or "percent identity", it is meant one or more than one nucleic acid or amino acid sequence that is substantially identical to a coding sequence or amino acid sequence of the specified polypeptide. By "substantially identical" is meant any nucleotide or amino acid sequence with similarity to the sequence of a nucleic acid or amino acid of the invention, or a fragment or a derivative thereof. The term "substantially identical" can also be used to describe similarity of polypeptide sequences. For example, nucleotide sequences or to polypeptide sequences that are at least 70%, 75%, 80%, 85%, 90%, 92%, 95%, 96%, 98% or 99% identical to the polypeptide coding sequence, or the encoded polypeptide, respectively, or fragments or derivatives thereof, and still retain ability to affect HIV replication are contemplated.

To determine whether a nucleic acid exhibits identity with the sequences presented herein, oligonucleotide alignment algorithms may be used, for example, but not limited to a BLAST (GenBank URL: www.ncbi.nlm.nih.gov/cgi-bin/BLAST/, using default parameters: Program: blastn; Database: nr; Expect 10; filter: default; Alignment: pairwise; Query genetic Codes: Standard(1)), BLAST2 (EMBL URL: http://www.embl-heidelberg.de/Services/index.html using default parameters: Matrix BLOSUM62; Filter: default, echofilter: on, Expect: 10, cutoff: default; Strand: both; Descriptions: 50, Alignments: 50), or FASTA search, using default parameters. Polypeptide alignment algorithms are also available, for example, without limitation, BLAST 2 Sequences (www.ncbi.nlm.nih.gov/blast/bl2seq/bl2.html, using default parameters Program: blastp; Matrix: BLOSUM62; Open gap (11) and extension gap (1) penalties; gap x_dropoff: 50; Expect 10; Word size: 3; filter: default).

An alternative indication that two nucleic acid sequences are substantially identical is that the two sequences hybridize to each other under moderately stringent, or preferably stringent, conditions. Hybridization to filter-bound sequences under moderately stringent conditions may, for example, be performed in 0.5 M NaHPO$_4$, 7% sodium dodecyl sulfate (SDS), 1 mM EDTA at 65° C., and washing in 0.2×SSC/0.1% SDS at 42° C. for at least 1 hour (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO$_4$, 7% SDS, 1 mM EDTA at 65° C., and washing in 0.1×SSC/0.1% SDS at 68° C. for at least 1 hour (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y.). Generally, but not wishing to be limiting, stringent conditions are selected to be about 5° C. lower than the thermal melting point for the specific sequence at a defined ionic strength and pH.

By protein transduction domain it is meant a sequence of nucleic acids that encode a polypeptide, or a sequence of amino acids comprising the polypeptide, wherein the polypeptide facilitates localization to a particular site, for example a cell or the like, or it may facilitate transport across a membrane or lipid bilayer. The polypeptides and nucleic acids of the present invention may be fused to a protein transduction domain to facilitate transit across lipid bilayers or membranes.

Many polypeptides and nucleic acids do not efficiently cross the lipid bilayer of the plasma membrane, and therefore enter into cells at a low rate. However, there are certain naturally occurring polypeptides that can transit across membranes independent of any specific transporter. Antennapedia (Drosophila), Tat (HIV) and VP22 (Herpes) are examples of such polypeptides. Fragments of these and other polypeptides have been shown to retain the capacity to transit across lipid membranes in a receptor-independent fashion. These fragments, termed protein transduction domains, are generally 10 to 27 amino acids in length, possess multiple positive charges, and in several cases have been predicted to be amphipathic. Polypeptides and nucleic acids that are normally inefficient or incapable of crossing a lipid bilayer can be made to transit the bilayer by being fused to a protein transduction domain.

U.S. Publication 2002/0142299 (which is incorporated herein by reference) describes a fusion of Tat with human beta-glucuronidase. This fusion protein readily transits into various cell types both in vitro and in vivo. Furthermore, Tat fusion proteins have been observed to cross the blood-brain-barrier. Frankel et al. (U.S. Pat. No. 5,804,604, U.S. Pat. No. 5,747,641, U.S. Pat. No. 5,674,980, U.S. Pat. No. 5,670,617 and U.S. Pat. No. 5,652,122; which are incorporated herein by reference) have also demonstrated transport of a protein (beta-galactosidase or horseradish peroxidase) into a cell by fusing the protein with amino acids 49-57 of Tat.

PCT Publication WO01/15511 (which is incorporated herein by reference) discloses a method for developing protein transduction domains using a phage display library. The method comprises incubating a target cell with a peptide display library and isolating internalized peptides from the cytoplasm and nuclei of the cells and identifying the peptides. The method further comprises linking the identified peptides to a protein and incubating the peptide-protein complex with a target cell to determine whether uptake is facilitated. Using this method a protein transduction domain for any cell or tissue type may be developed. US Publication 2004/0209797 (which is incorporated herein by reference) shows that reverse isomers of several of the peptides identified by the above can also function as protein transduction domains.

PCT Publication WO99/07728 (which is incorporated herein by reference) describes linearization of protegrin and tachyplesin, naturally occurring as a hairpin type structure held by disulphide bridges. Irreversible reduction of disulphide bridges generated peptides that could readily transit cell membranes, alone or fused to other biological molecules. US Publication 2003/0186890 (which is incorporated herein by reference) describes derivatives of protegrin and tachyplesin that were termed SynB1, SynB2, SynB3, etc. These SynB peptides were further optimized for mean hydrophobicity per residue, helical hydrophobic moment (amphipathicity), or beta hydrophobic moment. Various optimized amphipathic SynB analog peptides were shown to facilitate transfer of doxorubicin across cell membranes. Further, doxorubicin linked to a SynB analog was observed to penetrate the blood-brain-barrier at 20 times the rate of doxorubicin alone.

The protein transduction domains described in the preceding paragraphs are only a few examples of the protein transduction domains available for facilitating membrane transit of small molecules, polypeptides or nucleic acids. Other examples are transportan, W/R, AlkCWK18, DipaLytic, MGP, or RWR. Further examples include lipids and other chemical groups to induce cell permeability. Still many other examples will be recognized by persons skilled in the art.

A protein transduction domain and a polypeptide of the present invention may be placed together in sufficient proximity and maintained together for a sufficient time to allow the protein transduction domain to influence pharmaceutical product performance of the polypeptide. Contemplated associations of protein transduction domain and polypeptide include, for example and without limitation: non-covalent associations such as electrostatic interactions, hydrogen bonding, ionic bonds or complexes, Van der Waals bonds; covalent linkages such as conventional methods of cross-linking; linkages that are activated, in vitro and/or in vivo by electromagnetic radiation; any covalent bond such as a peptide bond; any biochemical interaction known to protein biochemists, such as biotin/streptavidin, nickel/Histidine, glutathione/glutathione-S-transferase, or antigen/antibody; physical associations within matrix structures or encapsulating systems; etc.

A polypeptide of the invention can be synthesized in vitro or delivered to a cell in vivo by any conventional method. As a representative example of an in vitro method, the polypeptide may be chemically synthesized in vitro, or may be enzymatically synthesized in vitro in a suitable biological expression system, such as without limitation, wheat germ extract or rabbit reticulocyte lysate. As a representative example of an in vivo method, a DNA, RNA, or DNA/RNA hybrid molecule comprising a nucleotide sequence encoding a polypeptide of the invention is introduced into an animal, and the nucleotide sequence is expressed within a cell of an animal.

The nucleotide sequence may be operably linked to regulatory elements in order to achieve preferential expression at desired times or in desired cell or tissue types. Furthermore, as will be known to one of skill in the art, other nucleotide sequences including, without limitation, 5' untranslated regions, 3' untranslated regions, cap structures, poly A tail, translational initiators, sequences encoding signaling or targeting peptides, translational enhancers, transcriptional enhancers, translational terminators, transcriptional terminators, transcriptional promoters, may be operably linked with the nucleotide sequence encoding a polypeptide (see as a representative examples "Genes VII", Lewin, B. Oxford University Press (2000) or "Molecular Cloning: A Laboratory Manual", Sambrook et al., Cold Spring Harbor to Laboratory, 3rd edition (2001)). A nucleotide sequence encoding a polypeptide or a fusion polypeptide comprising a polypeptide agent and a protein transduction domain may be incorporated into a suitable vector. Vectors may be commercially obtained from companies such as Stratagene or InVitrogen. Vectors can also be individually constructed or modified using standard molecular biology techniques, as outlined, for example, in Sambrook et al. (Cold Spring Harbor Laboratory, 3rd edition (2001)). A vector may contain any number of nucleotide sequences encoding desired elements that may be operably linked to a nucleotide sequence encoding a polypeptide or fusion polypeptide comprising a protein transduction domain. Such nucleotide sequences encoding desired elements, include, but are not limited to, transcriptional promoters, transcriptional enhancers, transcriptional terminators, translational initiators, translational, terminators, ribosome binding sites, 5' untranslated regions, 3' untranslated regions, cap structures, poly A tail, origin of replication, detectable markers, affinity tags, signals or target peptides. Persons skilled in the art will recognize that the selection and/or construction of a suitable factor may depend upon several factors, including, without limitation, the size of the nucleic acid to be incorporated into the vector, the type of transcriptional and translational control elements desired, the level of expression desired, copy number desired, whether chromosomal integration is desired, the type of selection process that is desired, or the host cell or the host range that is intended to be transformed.

The DNA, RNA, or DNA/RNA hybrid molecule may be introduced intracellularly, extracellularly into a cavity, interstitial space, into the circulation of an organism, orally, or by any other standard route of introduction for therapeutic molecules and/or pharmaceutical compositions. Standard physical methods of introducing nucleic acids include, but are not limited to, injection of a solution comprising RNA, DNA, or RNA/DNA hybrids, bombardment by particles covered by the nucleic acid, bathing a cell or organism in a solution of the nucleic acid, or electroporation of cell membranes in the presence of the nucleic acid.

A nucleic acid may be introduced into suitable eukaryotic cells ex vivo and the cells harboring the nucleic acid can then be inserted into a desired location in an animal. A nucleic acid can also be used to transform prokaryotic cells, and the transformed prokaryotic cells can be introduced into an animal, for example, through an oral route. Those skilled in the art will recognize that a nucleic acid may be constructed in such a fashion that the transformed prokaryotic cells can express and secrete a polypeptide of the invention. Preferably, the prokaryotic cell is part of the animal's endogenous intestinal microflora. With regards to human examples of endogenous microflora are, without wishing to be limiting, *Lactobacillus acidophillus, Streptococcus thermophilus*, and *Bifidobacterium bifidum*. A nucleic acid may also be inserted into a viral vector and packaged into viral particles for efficient delivery and expression.

Dosage Forms

A polypeptide of the present invention, or nucleic acids encoding these polypeptides, may be formulated into any convenient dosage form. The dosage form may comprise, but is not limited to an oral dosage form wherein the agent is dissolved, suspended or the like in a suitable excipient such as but not limited to water. In addition, the agent may be formulated into a dosage form that could be applied topically or could be administered by inhaler, or by injection either subcutaneously, into organs, or into circulation. An injectable dosage form may include other carriers that may function to enhance the activity of the agent. Any suitable carrier known in the art may be used. Also, the polypeptide may be formulated for use in the production of a medicament. Many methods for the productions of dosage forms, medicaments, or pharmaceutical compositions are well known in the art and can be readily applied to the present invention by persons skilled in the art.

It is also envisioned that carrier molecules or groups may be incorporated into the polypeptide of the present invention, or nucleic acids encoding these polypeptides, or a formulation, composition or medicament ad described herein, to enhance permeability through the brain-blood-barrier. Such carrier molecules or groups will be apparent and can be varied according to the knowledge of those skilled in the relevant art.

Combination therapy with polypeptides of the present invention or other agents useful for preventing and/or treating HIV infection or replication is also contemplated. With regards to combination therapy, suitable dosage forms again include capsules, tablets, and the like, preferably for oral administration, although any dosage form, for any route of administration is contemplated. Combination therapy can be administered as separate entities, e.g. two tablets or other forms, each containing one agent, or may be administered as a single dosage form containing both drugs, or concomitant use.

In case of oral administration of two or more different agents, the single dose can be, but is not limited to a capsule, tablet, or oral solution, and it may also contain inactive component(s) necessary to form the single delivery system.

Combination therapy medications of the present invention may be administered by any desired route without limitation, for example administration can be transdermal (patch), buccal, sublingual, topical, nasal, parenteral (subcutaneous, intramuscular, intravenous, intradermal), rectal, or vaginal. Various combinations of controlled release/rapid release are also contemplated.

The methods and compositions of the present invention are useful for preventing and/or treating HIV infection or replication. These will be further illustrated in the following experiments.

Experiments:

The TOE1 gene has been previously cloned, as a genetic target of the Egr1 transcription factor using a chromatin immunoprecipitation technology (24), and was also shown to be upregulated in $CD8^+$ T cells (25). Specifically, TOE1 was among three identified transcripts that were found upregulated in the $CD8^+$ population derived from an HIV-infected long term non-progressor, in comparison with his uninfected twin sibling. To better understand the biological role of TOE1 the present inventors have studied its importance in CNAR and found that TOE1, and derivatives thereof as described herein, inhibits HIV replication.

TOE1 Contributes to a CAF-Like Activity

Figures 2, 3:
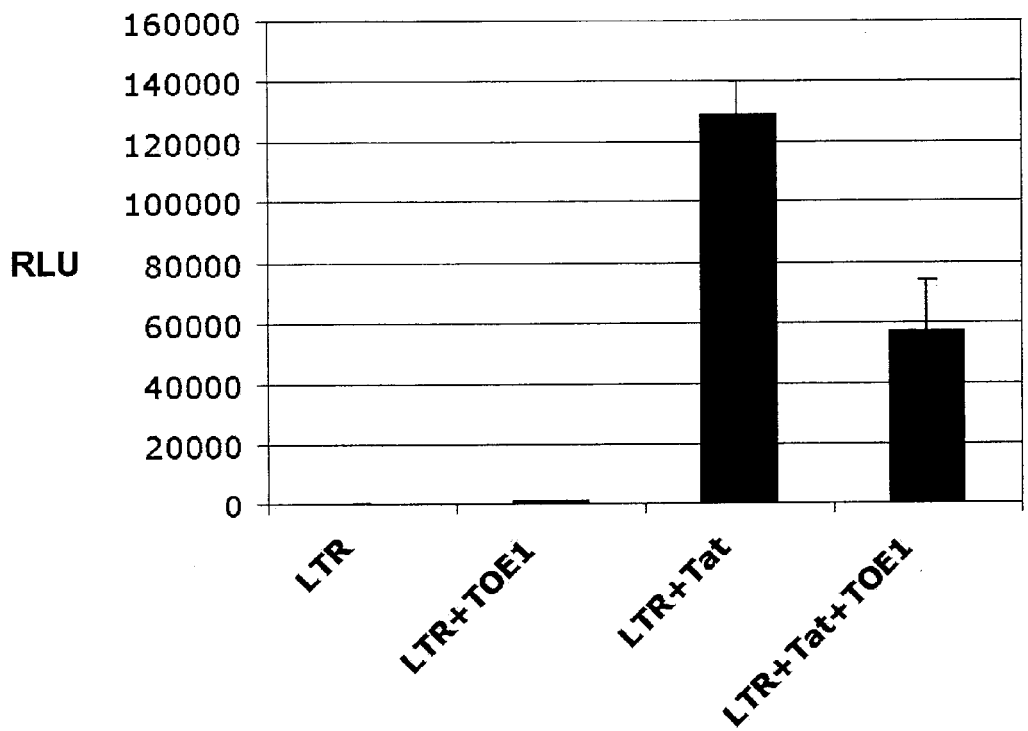
FIG. 2: Sequence comparison of basic amino acid sequence regions in Tat (SEQ ID NO:19) and TOE1 (SEQ ID NO:20).
FIG. 3: TOE1 inhibits Tat driven HIV LTR expression. HeLa cells were seeded into 24 wells plates at 30,000 cells/well and then transfected the following day with the indicated constructs at 200 ng total DNA+0.5 µl of FuGENE™ (Roche)/well. 24 hours after transfection the cells were lysed and the luciferase expression was determined by reading Relative Bioluminescent Units (RLU). This graph is representative of multiple experiments performed in triplicates.

If TOE1 functions in a CAF-like manner, then it should affect viral LTR driven transcription. Interestingly, a structural comparison between TOE1 and Tat revealed a region of homology between these two proteins (FIG. 2). This region consists of a highly basic stretch of lysine and arginine residues, important for both nuclear localization and for uptake of secreted factor (26, 27). While many nuclear proteins contain basic nuclear localization domains, it is unusual to have an extended stretch of 12 consecutive basic residues as seen in TOE1. Significantly, this basic region in Tat is critical for interaction with TAR and for its transactivation function (28).

TOE1 Modulates Tat Transactivation of HIV LTR

To test for a potential interaction between TOE1 and Tat, we assessed the effect of TOE1 expression on Tat driven transactivation of the TAR element. We employed a luciferase expression system controlled by the HIV LTR including the TAR sequence. As shown in FIG. 3, we found that when TOE1 was coexpressed with Tat, it reduced its transactivation potential by 50-80% in different experiments. TOE1 did not have any effect on the LTR in the absence of Tat; rather its expression appeared to affect Tat activation of TAR.

TOE1 is a Substrate for Caspase-1

Figure 4:
FIG. 4: TOE1 is a substrate for caspase-1. (A) Endogenously expressed TOE1 was immunoprecipitated from a lysate of Jurkat cells using the rabbit polyclonal α-TOE1 antibody or pre-immune serum (control=C) and ProteinA/Sepharose™ beads. Immunoprecipitates complexed beads were then incubated with 5 units of recombinant caspase-1 (from Calbiochem) or control buffer, as indicated, for 4 hours at 37° C., and then separated on a 12% Acrylamide/SDS gel and transferred on a PVDF membrane. 50 kDa, 40 kDa and 30 kDa fragments are visible after probing the blot with the monoclonal α-TOE1 antibody. (B) Cell lysates from cells transfected with a TOE1 expression construct were subjected to immunoprecipitation with the rabbit α-TOE1 antibody and ProteinA/Sepharose™ beads. The immunoprecipitates were then incubated with either buffer alone, caspase-1 or caspase-1 in the presence of the caspase inhibitor YVAD-CHO, and processed as described for Panel A. Western blot performed with the rabbit α-TOE1 antibody reveals fragments of approximately 50 kDa, 30 kDa, 25 kDa and 16 kDa. The presence of YVAD-CHO completely prevents the processing of TOE1 by caspase-1. Note that the secondary α-rabbit antibody used for the blot in (B) also reveals the IgG used for the immunoprecipitation.

During characterization of TOE1 we observed multiple bands by Western blot analysis suggesting potential proteolytic processing. Since, as described earlier, CAF activity is reported to be dependent upon proteolytic activity, we decided to explore the possibility that TOE1 is a protease substrate. Using the ExPASy (Expert Protein Analysis System) protemics peptide cutter prediction software, we found that TOE1 is predicted to be a substrate for the pro-inflammatory protease ICE (caspase-1). The software predicts a single cleavage for the tetrapeptide FTAD at position 214-217 of TOE1. We considered this potential cleavage to warrant further study for several reasons. First, CAF is associated with viral infection, which is known to activate the inflammatory response, including caspase-1 activation. Secondly, very few biological substrates for caspase-1 are currently known, so the identification of a new substrate for this enzyme is of great interest for inflammation and cell death. To test this possibility, we isolated TOE1 by immunoprecipitation from TOE1 expressing THP1 cells using an affinity purified antibody against the C-terminal of TOE1, and then performed in vitro digestion with recombinant purified caspase-1 (Calbiochem). We found that TOE1 was indeed processed by caspase-1, and generated multiple cleaved forms. Significantly, processing was inhibited by a specific inhibitor of caspase-1, YVAD-CHO (FIG. 4). Under our experimental conditions we observed processing by casaspase-1 generating fragments of 50, 40, and 30 kDa as detected with a monoclonal anti-TOE1 antibody whose target epitope we have mapped to residues 218-282 (FIG. 4A). Using our C terminal directed polyclonal anti-TOE1 antibody, we observed fragments of 50, 28, 25, and 16 kDa (FIG. 4B).

Figure 5:
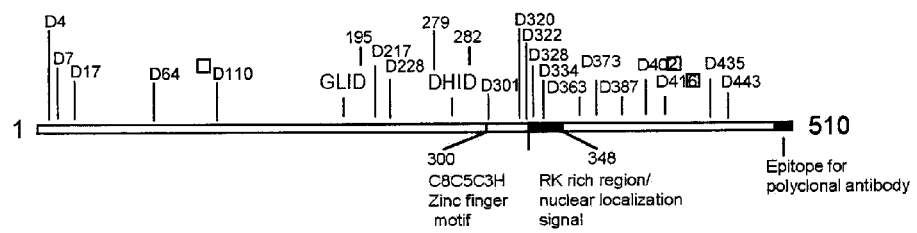
FIG. 5: Schematic representation of TOE1 protein. Aspartate residues that represent potential caspase-1 cleavage sites are indicated.
Figure 6:
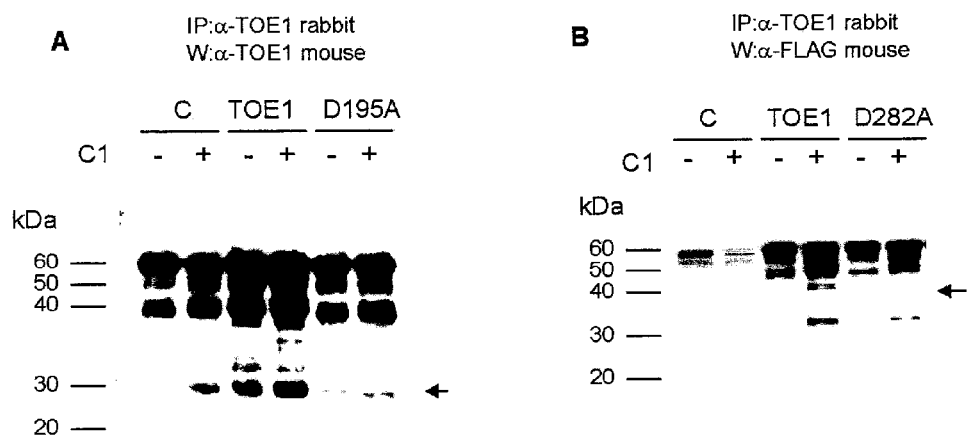
FIG. 6: Identification of the caspase-1 cleavage sites of TOE1 GLID and DHID. Mutant constructs D195A and D282A of N-terminal FLAG tagged TOE1 were generated by QuikChange™ (Stratagene) and then transfected into 293T cells. Cell lysates were immunoprecipitated using the rabbit α-TOE1 antibody and caspase-1 incubation was carried out as described for FIG. 4. (A) Western blot analysis using the monoclonal α-TOE1 antibody reveals that the caspase-1 cleavage at D195 within the site GLID generates the 30 kDa fragment as this fragment is greatly decreased in the mutant (arrow head). Note that a minor band still present in the mutant originates from endogenous TOE1. (B) Western blotting with an α-FLAG antibody detects a 40 kDa N-terminal fragment generated by caspase-1. Cleavage occurs at D282 within the site DHID as evidenced by the loss of this fragment in the mutant protein (arrow head).

As caspase cleavage sites are invariant aspartates at the C termini of tetrapeptide recognition motifs, we generated a series of TOE1 constructs bearing mutations in asparate residues changed to alanines. In constructing mutants we considered candidate caspase-1 cleavage sites predicted on the basis of the fragments size observed by in vitro caspase-1 cleavage (see FIG. 5). Five potential cleavage site mutants were generated and two of these mutations were found to prevent the appearance of a cleavage product of TOE1 upon incubation with caspase-1. These consisted of the D195 and D282 residues within the sites GLID and DIHD respectively (FIG. 6). Interestingly, when the caspase-1 cleavage site predicted using the ExPASy software was mutated (FTAD), in vitro cleavage was maintained.

Figure 7:
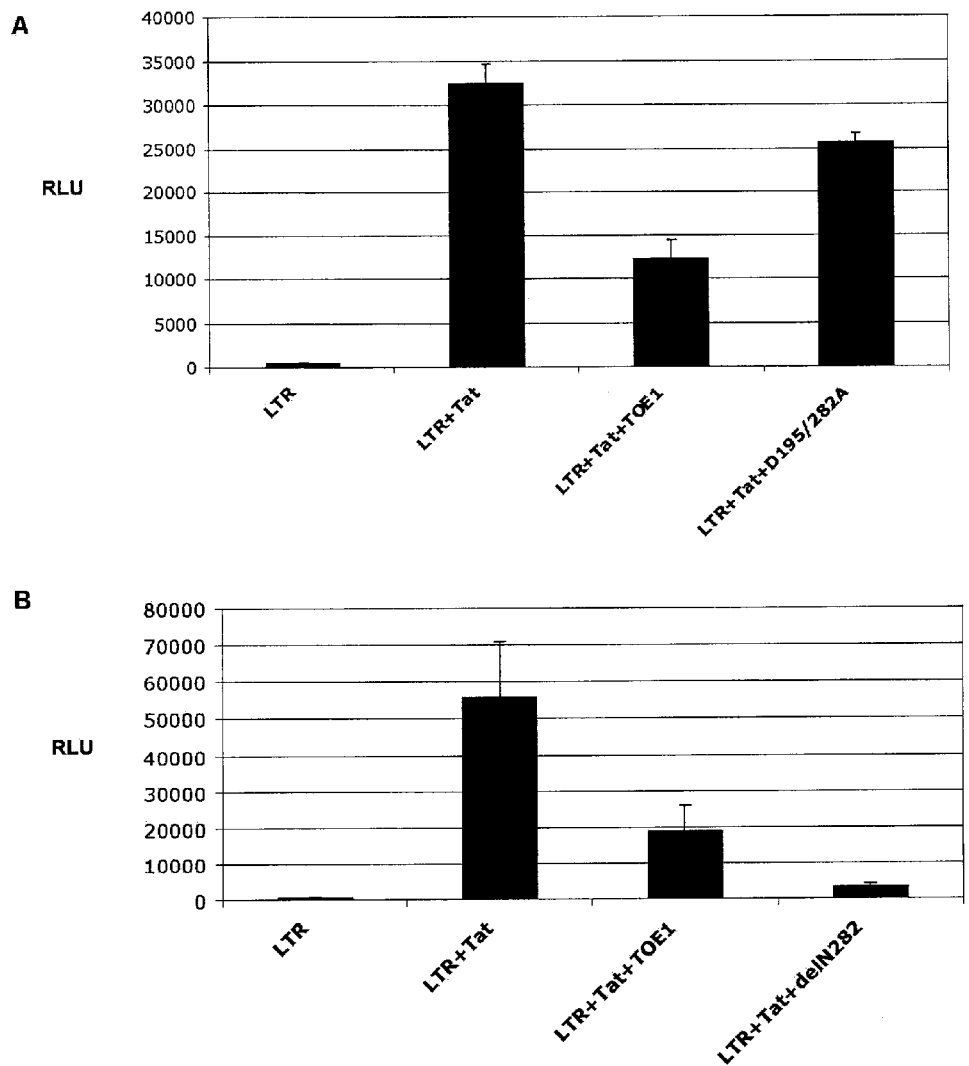
FIG. 7: TOE1 processing by caspase-1 enhances its inhibition of HIV LTR transactivation by Tat. (A) HeLa cells were transfected with the indicated constructs, and then luciferase assay was performed as described above. The double mutant D195/282A is less effective than wild type TOE1 in Tat inhibition. (B) A TOE 1 deletion mutant lacking the first 282 amino acids (delN282, SEQ ID NO:8) is a more efficient inhibitor of Tat activation. All transfection and measurements were performed in triplicate.

Cleavage of TOE1 by Caspase-1 Enhances its Inhibition of HIV LTR Transactivation We then tested whether preventing processing by caspase-1 could alter TOE1s effect on Tat transactivation of HIV LTR. As shown in FIG. 7A, the double mutant D195/282A was significantly less effective in its inhibitory activity of Tat activation of HIV LTR. Moreover, an N-terminal deletion construct of TOE1 up to the D282 caspase-1 cleavage site, delN282 (SEQ ID NO:8), displayed greater inhibition than wild-type TOE1 on Tat activity (FIG. 7B). These results are consistent with a model in which the active form of TOE1 is the caspase-1 processed form.

Figure 8:
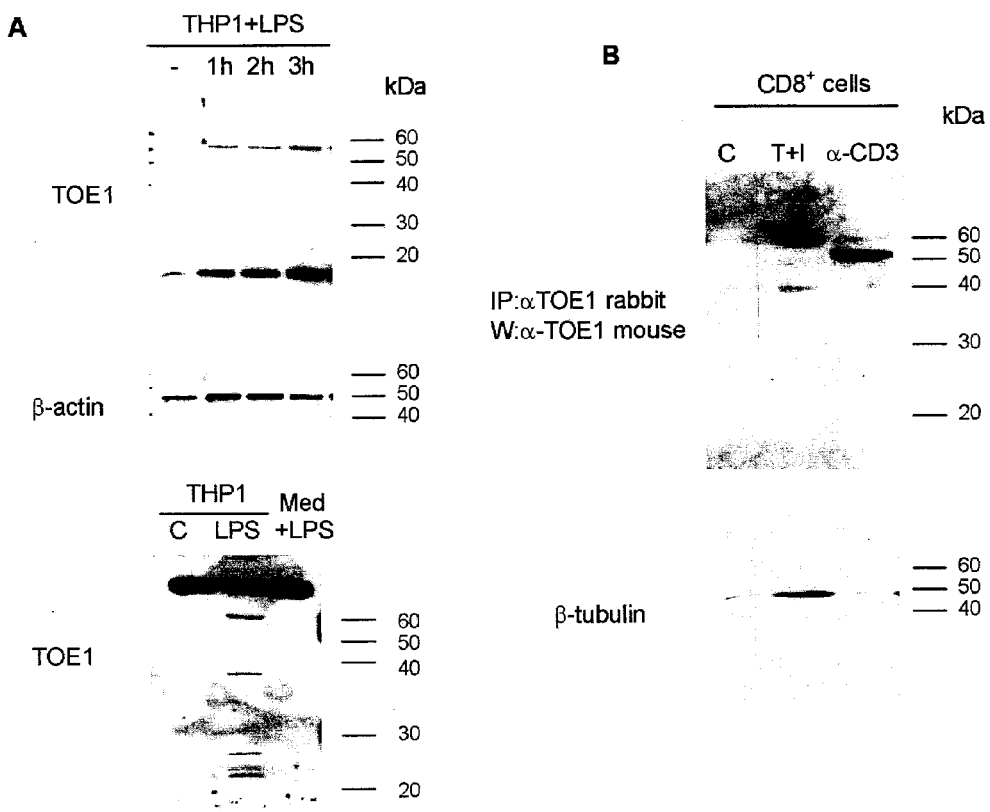
FIG. 8: TOE1 is actively secreted from THP1 subjected to an inflammatory stimulus and α-CD3 activated primary human CD8+ cells. (A) THP1 cells were incubated with LPS (SIGMA) at 2 µg/ml, in reduced serum medium containing 0.1% FBS at the indicated times. 50 µl of the medium were loaded on a 12% Acrylamide/SDS gel and transferred on a PVDF membrane. The blot was probed with the rabbit α-TOE1 antibody (upper blot) and subsequently with β-actin (middle blot). While TOE1 appears in the medium upon LPS stimulation, the actin signal does not change. In the bottom blot, 50 µl of the 10× concentrated conditioned medium was loaded on a 12% Acrylamide/SDS gel. Western blot with the rabbit α-TOE1 antibody reveals the presence TOE1 fragments consistent with the caspase-1 cleavage products. No similar bands are visible in the control LPS containing medium incubated without cells (Med.+LPS). The major upper band in this blot corresponds to a cross-reacting species originating from the medium. (B) Primary human CD8+ cells from a healthy donor were incubated with either medium only (C) or TPA(25 ng/ml)/Ionomycin (1 µg/ml) (T+I) or α-CD3 antibody for 48 hours. The conditioned medium was then immunoprecipitated with rabbit α-TOE1 antiserum and then loaded on a 12% Acrylamide/SDS gel. The blot was probed with mouse α-TOE1 antibody (upper blot). 50 µl of conditioned medium prior to immunoprecipitation were loaded on a separate gel and probed with a α-β-tubulin antibody to assess the presence of passive release of intracellular proteins. Treatment with α-CD3 induces the active secretion of a main 50 kDa species of TOE1, along with minor amounts of the full-length and the 40 kDa fragment consistent with known caspase-1 processing products. No release of β-tubulin is observed in these conditions. Treatment with TPA/Ionomycin induced release of intact TOE1 along with β-tubulin into the medium.

TOE1 is Secreted from THP1 Cells Following an Inflammatory Stimulus and α-CD3-Stimulated Human CD8+ Cells Without wishing to be limited by theory, it is thought that TOE1 might exhibit CAF-like activity. Since CAF acts through a secretion/uptake pathway, we tested whether we could witness any secretion of TOE1. To this end, we treated THP1 cells with LPS to provide a proinflammatory stimulus and to activate caspase-1 in these cells. We found that TOE1, despite its nucleolar localization, was actively secreted in the culture medium beginning at 1 hour following the inflammatory stimulus. Both full-length and smaller TOE1 species, consistent with the products of previously observed caspase-1 cleavage, were found secreted into the culture medium (FIG. 8A). We next tested human primary CD8+ cells where a CAF-like activity can be triggered upon stimulation, though in smaller amounts than observed from cells derived from long term non-progressors (30). We found that TOE1 was also actively secreted from α-CD3 treated primary CD8+ cells as determined by immunoprecipitation from conditioned medium, followed by Western blotting (FIG. 8B). The most abundant species of TOE1 found in the medium from these cells was a 50 kDa product along with minor band of 40 kDa, corresponding to the previously demonstrated caspase-1 cleavage product and a minor quantity of full-length protein. The results from these primary cells are consistent with our prior observations and indicate that the secretion of TOE1 and its fragments occurs in stimulated primary human cells.

Determining the Minimum Domain of TOE1 Required for Tat-Mediated HIV LTR Inhibition: Mutational Analysis of TOE1 (or Aspartate Scanning Analysis)

In view of the finding that TOE1 is a substrate for caspase-1, it is believed that processing by caspase-1 may be implicated in its inhibitory role in HIV LTR transcription. As a result, it will be useful to define the minimal active TOE1 fragment generated by caspase-1. By identifying this region of TOE1 a further understanding the structural features of TOE1 participating in Tat inhibition can be achieved. This information can also be used for the design of therapeutic compounds.

As described earlier, we found that a double mutant of TOE1 that is not cleaved by caspase-1 at aspartates 195 and 282 has a reduced inhibitory activity of Tat-dependent transcription. Furthermore, we found that a deletion mutant of TOE1, delN282 (SEQ ID NO:8), displays a more powerful inhibitory activity. As can be seen in FIG. 5, the C terminal portion of TOE1 from amino acids 282-510 retains the highly basic domain sharing similarity with the Tat basic region. We have also found multiple candidate caspase-1 cleavage sites map within the C terminus of TOE1, generating fragments of approximately 16, 25 and 28 kDa. Therefore, one or more of these cleavages can provide a more active inhibitory form of TOE1.

Each of the aspartate residues cleaved by caspase-1 can be identified as shown above for the mapping of the D195 and D282 cleavage sites. Specifically, mutagenesis of TOE1 was performed by changing the aspartates at all candidate sites into alanines using QuickChange mutagenesis, developed by Stratagene. To this end, we have successfully identified additional caspase-1 cleavage sites corresponding to TOE1 amino acids 363 and 373 that are responsible for generating an approximately 17 kDa proteolytic fragment (FIG. 10). Additionally, to define the minimal TOE1 domain capable of inhibiting Tat driven LTR expression, we created additional deletion mutants based upon the observed caspase-1 cleavage sites. As shown in FIG. 9, a number of TOE1 mutants were shown to inhibit Tat activation of the HIV LTR. Amongst these TOE1 mutants, we identified amino acids 1-402 (SEQ ID NO:128), 1-373 (SEQ ID NO:129), 283-363 (SEQ ID NO:13), 323-402 (SEQ ID NO:39), 323-363 (SEQ ID NO:36) and 335-363 (SEQ ID NO:17) as capable of significantly inhibiting Tat activation of the HIV LTR.

TOE1 Amino Acids 283-363 Comprise a Protein Transduction Domain

To determine if TOE1 could be secreted and subsequently taken up by other neighboring cells, we performed co-culture experiments of cells transfected with the HIV LTR reporter and Tat protein in one cell type and either full length TOE1 or the potential protein transduction domain of TOE1 comprising amino acids 283-363 (SEQ ID NO:13) in another cell type. As can be seen in FIG. 11, both full length TOE1 and the mutant comprising residues 283-363 (SEQ ID NO:13) were capable of effectively inhibiting Tat activation of the HIV LTR. These results indicate that both TOE1 and residues 283-363 were actively secreted, imported into target cells and inhibited Tat activation. Therefore, a minimal domain of TOE1, comprising the basic stretch of amino acids at position 335-347 (SEQ ID NO:15), was able to function as a protein transduction domain as well as an effective inhibitor of Tat transcriptional activation.

Testing the Minimal HIV Inhibitory Active TOE1 In Vivo

Active TOE1 fragments can be tested in vivo for their ability to block HIV replication in primary human cells. This can be carried out by making a GST fusion construct of the minimal active TOE1 fragment to be amplified and expressed in bacteria. This GST fusion protein can then be extracted and purified through Glutathione Sepharose chromatography. The GST tag can be cleaved by incubation of GST protein, bound to Glutathione Sepharose, with a biotinylated thrombin that is subsequentially removed by capture with Streptavidin Sepharose and centrifugation. The purified recombinant TOE1 active fragment can then be dialyzed against PBS, and sterile filtered for in vivo testing as described below.

Peripheral blood is obtained from normal healthy donors and peripheral blood mononuclear cells (PBMCs) prepared by centrifugation on a Ficoll-Hypaque density gradient. Next, $CD4^+$ T cells are isolated by using a negative selection kit according to the manufacturer's instructions (StemCell Technologies), activated with PHA-L (1 µg/ml) and maintained in complete culture medium supplemented with IL-2 (30 U/ml) at a density of $2 \times 10^6$ cells/ml. Experiments can be conducted with different fully infectious laboratory (i.e. NL4-3, NL4-3-Balenv, JR-CSF) and primary isolates of HIV-1 bearing distinct co-receptor utilization profiles (i.e. R5/macrophage-tropic, X4/T-tropic, and R5X4/dual-tropic). Such HIV-1 variants can be obtained through the NIH AIDS Research and Reference Reagent Program (Germantown, Md.). The luciferase-encoding $pNL4-3Luc^+ E^- R^+$ vector can be used to generate single-cycle luciferase reporter viruses pseudotyped with the broad host range vesicular stomatitis virus envelope glycoprotein G (VSV-G). Virus stocks can be prepared by transient transfection of 293T cells. Primary isolates of HIV-1 are expanded in human PBMCs. Each virus preparation is filtered through a 0.22 µm cellulose acetate syringe filter and purified through ultracentrifugation. This step eliminates free p24, the presence of which can lead to an overestimation of the actual number of infectious viral entities. Virus stocks are normalized for virion content using an in-house sensitive double-antibody sandwich enzyme-linked immunosorbent assay (ELISA) specific for the viral p24 protein. Activated CD4+ T cells are pulsed with HIV-1 viruses (10 ng of $p24/10^5$ cells) for two hours, washed, and then incubated with various concentrations of recombinant TOE1 active fragment prepared as described above. Virus production will be assessed at 2, 4 and 6 days post-infection by measuring the p24 levels in cell-free culture supernatants. All measurements will be performed in triplicate. Infection with luciferase-encoding viruses will be assessed at 3 days post-infection by measuring luciferase activity. The use of such single-cycle luciferase reporter viruses will allow us to measure the effect of TOE1 specifically on HIV-1 expression.

Experiments can be conducted with fully infectious viruses where the recombinant TOE1 is added before infection, and at various time points post-infection. This allows for the analysis of the effects of TOE1 on different steps on the viral life cycle i.e. viral entry/fusion, reverse transcription and integration, and viral expression.

The TOE1 inhibitory activity on the HIV LTR can also be studied in primary $CD4^+$ T cells. To this end, resting or activated $CD4^+$ T cells are transfected with HIV LTR driven luciferase encoding construct alone or along with the Tat expression vector pCEP4⁻Tat by Nucleofection using the human T cell nucleofector kit from Amaxa (now Lonza). Transfected cells are then incubated with recombinant TOE1 active fragment, and luciferase activity is measured, e.g. at 6, 24 and 48 hours post transfection. The effect of the TOE1 polypeptide can also be tested in other primary human cells including monocyte-derived macrophages (MDMs) and immature monocyte-derived dendritic cells (iMDDCs). In brief, CD14+ cells are isolated by using a CD14 positive selection kit (MACS CD14 micro beads from StemCell Technologies). To generate iMDDC, purified monocytes are cultured in RPMI 1640/10% fetal calf serum supplemented with granulocyte-macrophage colony stimulating factor (GM-CSF) (1,000 U/ml) and interleukin-4 (IL-4) (200 U/ml) for 7 days. To generate MDMs, monocytes purified by adherence to plastic are allowed to differentiate into macrophages in culture medium supplemented with recombinant human macrophage colony stimulating factor, at a final concentration of 100 ng/mL for 6 days. Infection assays are performed essentially as described above for $CD4^+$ T cells, using R5-tropic viruses such as NL4-3BalEnv and VSVG-pseudotyped viruses.

One or more currently preferred embodiments have been described by way of example. It will be apparent to persons skilled in the art that a number of variations and modifications can be made without departing from the scope of the invention as defined in the claims.

REFERENCES

1. Esser, S., Helbig, D., Hillen, U., Dissemond, J., and Grabbe, S. Side effects of HIV therapy. J. Dtsch. Dermatol. Ges. 2007; 5: 745-54.
2. Harrich, D., McMillan, N. M., Munoz, L., Apolloni, A., and Meredith, L. Will diverse Tat interactions lead to novel antiretroviral drug targets? Curr Drug Targets 2006; 7: 1595-606.
3. Mackewicz, C. E., Garovoy, M. R., and Levy, J. A. HLA compatibility requirements for $CD8^+$ T cell-mediated suppression of human immunodeficiency virus replication. Journal of Virology 1998; 72(12):10165-10170.
4. Walker, C. M., Moody, D. J., Stites, D. P., and Levy, J. A. $CD8^+$ lymphocytes can control HIV infection in vitro by suppressing virus replication. Science 1986; 234: 1563-6.
5. Mackewicz, C. M., Yang, L. C., Lifson, J. D., and Levy, J. A. Non-cytolytic CD8 T cell anti-HIV responses in primary infection. Lancet 1994; 344: 1671-3.
6. Gomez, A. M., Smaill, F. M., and Rosenthal, K. L. Inhibition of HIV replication by $CD8^+$ T cells correlates with CD4 counts and clinical stage of disease. Clin Exp Immunol 1994; 97: 68-75.
7. Barker, E., Mackewicz, C. E., Reyes-Teran, G., Sato, A., Stranford, S. A., Fujimura, S. H., Christopherson, C., and Levy, J. A. Virological and immunological features of long-term human immunodeficiency virus-infected individuals who have remained asymptomatic compared with those who have progressed to acquired immunodeficiency syndrome. Blood 1998; 92: 3105-14.
8. Landay, A. L., Mackewicz, C. M., and Levy, J. A. An activated $CD^{*+}$ T cell phenotype correlates with anti-HIV activity and asymptomatic clinical status. Clin Immunol Immunopathol 1993; 69: 106-16.
9. Barker, E., Bossart, K. N., and Levy, J. A. Primary $CD8^+$ cells from HIV-infected individuals can suppress productive infection of macrophages independent of chemokines. Proc Natl Acad Sci USA 1998; 95: 1725-9.

10. Levy, J. A. The search for the CD8⁺ cell anti-HIV factor (CAF). Trends Immunol 2003; 24: 628-32.
11. Le Borgne, S., Fevrier, M., Callebaut, C., Lee, S. P., and Riviere, Y. CD8⁺ cell antiviral factor activity is not restricted to human immunodeficiency virus (HIV)-specific T cells and can block HIV replication after initiation of reverse transcription. J. Virol. 2000; 74: 4456-64.
12. Diaz, L. S., Foster, H., Stone, M. R., Fujimura, S. H., Reiman, D. A., and Levy, J. VCAM-1 expression on CD8⁺ cells correlates with enhanced anti-HIV suppressing activity. J Immunol 2005; 174: 1574-9.
13. Cocchi, F., DeVico, A. L., Garzino-Demo, A., Arya, S. K., Gallo, R. C., and Lusso, P. Identification of RANTES, MIP-1a and MIP-1b as the major HIV suppressive factors produced by CD8⁺ T cells. Science 1995; 270: 1811-5.
14. Geiben-Lynn, R., Brown, N., Walker, B. D., and Luster, A. D. Purification of a modified form of bovine antithrombin III as an HIV-1 CD8⁺ T cell antiviral factor. J Biol Chem 2002; 277: 42352-7.
15. Zhang, L., Yu, W., He, T., Yu, J., Caffrey, R. E., Dalmasso, E. A., Fu, S., Pham, T., Mei, J., Ho, J. J., Zhang, W., Lopez, P., and Ho, D. D. Contribution of human alpha-defensin 1,2, and 3 to the anti-HIV activity of CD8 antiviral factor. Science 2002; 298: 995-1000.
16. Mackewicz, C. E., Craik, C. S., and Levy, J. A. The CD8⁺ cell noncytotoxic anti-HIV response can be blocked by protease inhibitors. Proc Natl Acad Sci USA 2003; 100: 3433-8.
17. Mackewicz, C. E., Patterson, B. K., Lee, S. A., and Levy, J. A. CD8⁺ cell noncytotoxic anti-human immunodeficiency virus response inhibits expression of viral RNA but not reverse transcription or provirus integration. J Gen Virol 2000; 81: 1261-4.
18. Mackewicz, C. E., Blackbourn, D. J., and Levy, J. A. CD8⁺ cells suppress human immunodeficiency virus replication by inhibiting viral transcription. Proc Natl Acad Sci USA 1995; 92: 2308-12.
19. Copeland, K. F. T., McKay, P. J., and Rosenthal, K. L. Suppression of activation of the human immunodeficiency virus long terminal repeat by CD8⁺ T cells is not lentivirus specific. AIDS Res. Hum. Retroviruses 1995; 11: 1321-6.
20. Chang, T. L.-Y., Mosoian, A., Pine, R., Klotman, M. E., and Moore, J. P. A soluble factor(s) secreted from CD8⁺ T lymphocytes inhibits human immunodeficiency virustype 1 replication through STAT1 activation. J Virol 2002; 76: 569-81.
21. Bonneau, K. R., Ng, S., Foster, H., Choi, K. B., Berkhout, B., Rabson, A., Mackewicz, C. E., and Levy, J. A. Derivation of infectious HIV-1 molecular clones with LTR mutations: Sensitivity to the CD8⁺ cell noncytotoxic anti-HIV response. Virology 2007; 373: 30-8.
22. Roebuck, K. A. and Saifuddin, M. Regulation of HIV transcription. Gene Expression 1999; 8: 67-84.
23. Park, J., Nadeau, P. E., and Mergia, A. Activity of TAR inducible inhibition of HIV replication by foamy virus vector expressing siRNAs under the control of HIV LTR. Virus Research 2009; 140: 112-20.
24. de Belle, I., Wu, J.-X., Sperandio, S., Mercola, D., Adamson, E. D. In vivo cloning and characterization of a new growth suppressor protein TOE1 as a direct target gene of Egr1. Journal of Biological Chemistry 2003; 278: 14306-12.
25. Diaz, L. S., Stone, M. R., C. E., M., and Levy, J. A. Differential gene expression in CD8⁺ cells exhibiting noncytotoxic anti-HIV activity. Virology 2003; 311: 400-9.
26. Yang, Y., Ma, J., Song, Z., and Wu, M. HIV-1 Tat-mediated protein transduction and subcellular localization using novel expression vectors. FEBS Lett 2002; 532: 36-44.
27. Chang, H. C., Samaniego, F., Nair, B. C., Buonaguro, L., and Ensoli, B. HIV-1 Tat protein exits from cells via a leaderless secretory pathway and binds to extracellular matrix-associated heparin sulfate proteoglycans through its basic region. AIDS 1997; 11: 1421-31.
28. Long, K. S. and Crothers, D. M. Interaction of human immunodeficiency virus type 1 Tat-derived peptides with TAR RNA. Biochemistry 1995; 34: 8885-95.
29. Wagner, E., Clement, S. L., and Lykke-Andersen, J. An unconventional human Ccr4-Caf1 deadenylase complex in nuclear cajal bodies. Mol. Cell Biol. 2007; 27: 1686-95.
30. Barker, E., Bossart, K. N., Fujimura, S. H., and Levy, J. A. CD28 costimulation increases CD8⁺ cell suppression of HIV replication. J Immunol 1997; 159: 5123-31.
31. D'Orso, I. and Frankel, A. D. Tat acetylation modulates assembly of a viral-host RNA-protein transcription complex. Proc Natl Acad Sci USA 2009; 106: 3101-6.
32. Harrod, R., Nacsa, J., Van Lint, C., Hansen, J., Karpova, T., McNally, J., and Franchini, G. Human immunodeficiency virus type1 Tat/co-activator acetyltransferase interactions inhibit p53Lys-320 acetylation and p53-responsive transcription. J Biol Chem 2003; 278: 12310-8.
33. Gabizon, R., Mor, M., Rosenbeg, M. M., Britan, L., Hayouka, Z., Kotler, M., Shalev, D. E., and Freidler, A. Using peptides to study the interaction between the p53 tetramerization domain and HIV-1 Tat. Biopolymers 2008; 90: 105-16.
34. Sperandio, S., Tardito, S., Surzycki, A., Latterich, M., and de Belle, I. TOE1 interacts with p53 to modulate its transactivation potential. FEBS Lett 2009; 583:2165-70.
35. Seewald, M. J., Metzger, A. U., Willbold, D., Rosch, P., and Sticht, H. Structural model of the HIV-1 Tat(46-58)-TAR complex. J Biomol Struct Dyn 1998; 16: 683-92.

What is claimed is:

1. A polypeptide conjugate comprising (1) an amino acid sequence consisting of an amino acid sequence that is between 80% and 100% identical to the sequence of SEQ ID NO:2; SEQ ID NO:3; SEQ ID NO:4; SEQ ID NO:5; SEQ ID NO:6; SEQ ID NO:7; SEQ ID NO:9; SEQ ID NO:10; SEQ ID NO:11; SEQ ID NO:12; SEQ ID NO:13; SEQ ID NO:14; SEQ ID NO:16 or SEQ ID NO:17, or that is 100% identical to the sequence of SEQ ID NO:8; or which consists of an amino acid sequence that is between 80% and 100% identical to the sequence of a deletion mutant of Target Of Early Growth Response Gene 1 (TOE1), selected from the group consisting of G18/D363 (SEQ ID NO:104); G18/D373 (SEQ ID NO:105); G18/D387 (SEQ ID NO:106); G18/D402 (SEQ ID NO:107); G18/D416 (SEQ ID NO:108); G8/D363 (SEQ ID NO:112); G8/D373 (SEQ ID NO:113); G8/D387 (SEQ ID NO:114); G8/D402 (SEQ ID NO:115); S5/D363 (SEQ ID NO:120); S5/D373 (SEQ ID NO:121); S5/D387 (SEQ ID NO:122); and S5/D402 (SEQ ID NO:123); or that is between 85% and 100% identical to the sequence of deletion mutant of TOE1 G18/D435 (SEQ ID NO:109); G18/D443 (SEQ ID NO:110); G8/D416 (SEQ ID NO:116); G8/D435 (SEQ ID NO:117); or S5/D416 (SEQ ID NO:124); or that is between 90% and 100% identical to the sequence of deletion mutant of TOE1 G8/D443 (SEQ ID NO:118); S5/D435 (SEQ ID NO:125); or S5/D443 (SEQ ID NO:126); or that is 100% identical to the sequence of deletion mutant of TOE1 G18/S510 (SEQ ID NO:111); G8/S510 (SEQ ID NO:119); or S5/S510 (SEQ ID NO:127), wherein the indicated amino acids respectively specify the amino- and carboxy-terminal residues of the deletion mutants based on the sequence of SEQ ID NO:1, and, (2) a linked heterologous carrier molecule.

2. A polypeptide conjugate comprising: (1) an amino acid sequence that is any one of SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:16 or SEQ ID NO:17, or the amino acid sequence of a deletion mutant of TOE1 selected from the group consisting of K335/D373 (SEQ ID NO:21); K335/D387 (SEQ ID NO:22); K335/D402 (SEQ ID NO:23); K335/D416 (SEQ ID NO:24); K335/D435 (SEQ ID NO:25); K335/D443 (SEQ ID NO:26); K335/S510 (SEQ ID NO:27); E329/D363 (SEQ ID NO:28); E329/D373 (SEQ ID NO:29); E329/D387 (SEQ ID NO:30); E329/D402 (SEQ ID NO:31); E329/D416 (SEQ ID NO:32); E329/D435 (SEQ ID NO:33); E329/D443 (SEQ ID NO:34); E329/S510 (SEQ ID NO:35); L323/D363 (SEQ ID NO:36); L323/D373 (SEQ ID NO:37); L323/D387 (SEQ ID NO:38); L323/D402 (SEQ ID NO:39); L323/D416 (SEQ ID NO:40); L323/D435 (SEQ ID NO:41); L323/D443 (SEQ ID NO:42); L323/S510 (SEQ ID NO:43); I321/D363 (SEQ ID NO:44); I321/D373 (SEQ ID NO:45); I321/D387 (SEQ ID NO:46); I321/D402 (SEQ ID NO:47); I321/D416 (SEQ ID NO:48); I321/D435 (SEQ ID NO:49); I321/D443 (SEQ ID NO:50); I321/S510 (SEQ ID NO:51); N302/D363 (SEQ ID NO:52); N302/D373 (SEQ ID NO:53); N302/D387 (SEQ ID NO:54); N302/D402 (SEQ ID NO:55); N302/D416 (SEQ ID NO:56); N302/D435 (SEQ ID NO:57); N302/D443 (SEQ ID NO:58); N302/S510 (SEQ ID NO:59); Y283/D435 (SEQ ID NO:60); Y283/D443 (SEQ ID NO:61); H280/D363 (SEQ ID NO:62); H280/D373 (SEQ ID NO:63); H280/D387 (SEQ ID NO:64); H280/D402 (SEQ ID NO:65); H280/D416 (SEQ ID NO:66); H280/D435 (SEQ ID NO:67); H280/D443 (SEQ ID NO:68); H280/S510 (SEQ ID NO:69); T229/D363 (SEQ ID NO:70); T229/D373 (SEQ ID NO:71); T229/D387 (SEQ ID NO:72); T229/D402 (SEQ ID NO:73); T229/D416 (SEQ ID NO:74); T229/D435 (SEQ ID NO:75); T229/D443 (SEQ ID NO:76); T229/S510 (SEQ ID NO:77); L218/D363 (SEQ ID NO:78); L218/D373 (SEQ ID NO:79); L218/D387 (SEQ ID NO:80); L218/D402 (SEQ ID NO:81); L218/D416 (SEQ ID NO:82); L218/D435 (SEQ ID NO:83); L218/D443 (SEQ ID NO:84); L218/S510 (SEQ ID NO:85); L196/D435 (SEQ ID NO:86); L196/D443 (SEQ ID NO:87); K111/D363 (SEQ ID NO:88); K111/D373 (SEQ ID NO:89); K111/D387 (SEQ ID NO:90); K111/D402 (SEQ ID NO:91); K111/D416 (SEQ ID NO:92); K111/D435 (SEQ ID NO:93); K111/D443 (SEQ ID NO:94); K111/S510 (SEQ ID NO:95); T65/D363 (SEQ ID NO:96); T65/D373 (SEQ ID NO:97); T65/D387 (SEQ ID NO:98); T65/D402 (SEQ ID NO:99); T65/D416 (SEQ ID NO:100); T65/D435 (SEQ ID NO:101); T65/D443 (SEQ ID NO:102); T65/S510 (SEQ ID NO:103); G18/D363 (SEQ ID NO:104); G18/D373 (SEQ ID NO:105); G18/D387 (SEQ ID NO:106); G18/D402 (SEQ ID NO:107); G18/D416 (SEQ ID NO:108); G18/D435 (SEQ ID NO:109); G18/D443 (SEQ ID NO:110); G18/S510 (SEQ ID NO:111); G8/D363 (SEQ ID NO:112); G8/D373 (SEQ ID NO:113); G8/D387 (SEQ ID NO:114); G8/D402 (SEQ ID NO:115); G8/D416 (SEQ ID NO:116); G8/D435 (SEQ ID NO:117); G8/D443 (SEQ ID NO:118); G8/S510 (SEQ ID NO:119); S5/D363 (SEQ ID NO:120); S5/D373 (SEQ ID NO:121); S5/D387 (SEQ ID NO:122); S5/D402 (SEQ ID NO:123); S5/D416 (SEQ ID NO:124); S5/D435 (SEQ ID NO:125); S5/D443 (SEQ ID NO:126); S5/S510 (SEQ ID NO:127); M1/D402 (SEQ ID NO: 128); and M1/D373 (SEQ ID NO:129), wherein the indicated amino acids respectively specify the amino- and carboxy-terminal residues of the deletion mutants based on the sequence of SEQ ID NO:1; and (2) a linked heterologous carrier molecule.

3. The polypeptide conjugate of claim 2, wherein the heterologous carrier molecule is a protein transduction domain.

4. The polypeptide conjugate of claim 3, wherein the protein transduction domain comprises the amino acid sequence of Tat (SEQ ID NO: 18).

5. A composition comprising the polypeptide conjugate of claim 2 and a suitable carrier.

6. A method of inhibiting HIV in a cell comprising administering the polypeptide conjugate of claim 2 to the cell infected by an HIV virus.

7. The method of claim 6, wherein the method is an in vitro or in vivo method.

8. The method of claim 6, wherein the HIV virus is HIV-1 or HIV-2.

9. A method for treatment of human immunodeficiency virus (HIV) infection in a mammal in need of such treatment comprising administering to said mammal a polypeptide conjugate of claim 2 in an amount effective to treat said infection.

10. The method of claim 9, wherein the human immunodeficiency virus is HIV-1 or HIV-2.

11. The method of claim 9, wherein the heterologous carrier molecule is a protein transduction domain.

12. An antibody which binds to the polypeptide conjugate of claim 2.

13. The antibody of claim 12, wherein said antibody is a monoclonal antibody or polyclonal antibody.

14. An isolated nucleic acid encoding the polypeptide conjugate of claim 2.

15. A host cell transformed with the nucleic acid of claim 14.

16. A vector comprising the nucleic acid of claim 14.

* * * * *

SEQUENCE LISTING

<160> NUMBER OF SEQ ID NOS: 129

<210> SEQ ID NO 1
<211> LENGTH: 510
<212> TYPE: PRT
<213> ORGANISM: Homo sapiens

<400> SEQUENCE: 1

Met Ala Ala Asp Ser Asp Asp Gly Ala Val Ser Thr Pro Ala Ala Ser
1               5                   10                  15

Asp Gly Gly Val Ser Lys Ser Thr Thr Ser Gly Glu Glu Leu Val Val
            20                  25                  30

-continued

```
Gln Val Pro Val Val Asp Val Gln Ser Asn Asn Phe Lys Glu Met Trp
             35                  40                  45
Pro Ser Leu Leu Leu Ala Ile Lys Thr Ala Asn Phe Val Ala Val Asp
 50                  55                  60
Thr Glu Leu Ser Gly Leu Gly Asp Arg Lys Ser Leu Leu Asn Gln Cys
 65                  70                  75                  80
Ile Glu Glu Arg Tyr Lys Ala Val Cys His Ala Arg Thr Arg Ser
                 85                  90                  95
Ile Leu Ser Leu Gly Leu Ala Cys Phe Lys Arg Gln Pro Asp Lys Gly
            100                 105                 110
Glu His Ser Tyr Leu Ala Gln Val Phe Asn Leu Thr Leu Leu Cys Met
            115                 120                 125
Glu Glu Tyr Val Ile Glu Pro Lys Ser Val Gln Phe Leu Ile Gln His
            130                 135                 140
Gly Phe Asn Phe Asn Gln Gln Tyr Ala Gln Gly Ile Pro Tyr His Lys
145                 150                 155                 160
Gly Asn Asp Lys Gly Asp Glu Ser Gln Ser Gln Ser Val Arg Thr Leu
                165                 170                 175
Phe Leu Glu Leu Ile Arg Ala Arg Arg Pro Leu Val Leu His Asn Gly
            180                 185                 190
Leu Ile Asp Leu Val Phe Leu Tyr Gln Asn Phe Tyr Ala His Leu Pro
            195                 200                 205
Glu Ser Leu Gly Thr Phe Thr Ala Asp Leu Cys Glu Met Phe Pro Ala
            210                 215                 220
Gly Ile Tyr Asp Thr Lys Tyr Ala Ala Glu Phe His Ala Arg Phe Val
225                 230                 235                 240
Ala Ser Tyr Leu Glu Tyr Ala Phe Arg Lys Cys Glu Arg Glu Asn Gly
                245                 250                 255
Lys Gln Arg Ala Ala Gly Ser Pro His Leu Thr Leu Glu Phe Cys Asn
            260                 265                 270
Tyr Pro Ser Ser Met Arg Asp His Ile Asp Tyr Arg Cys Cys Leu Pro
            275                 280                 285
Pro Ala Thr His Arg Pro His Pro Thr Ser Ile Cys Asp Asn Phe Ser
            290                 295                 300
Ala Tyr Gly Trp Cys Pro Leu Gly Pro Gln Cys Pro Gln Ser His Asp
305                 310                 315                 320
Ile Asp Leu Ile Ile Asp Thr Asp Glu Ala Ala Glu Asp Lys Arg
                325                 330                 335
Arg Arg Arg Arg Arg Glu Lys Arg Lys Arg Ala Leu Leu Asn Leu
            340                 345                 350
Pro Gly Thr Gln Thr Ser Gly Glu Ala Lys Asp Gly Pro Pro Lys Lys
            355                 360                 365
Gln Val Cys Gly Asp Ser Ile Lys Pro Glu Glu Thr Glu Gln Glu Val
            370                 375                 380
Ala Ala Asp Glu Thr Arg Asn Leu Pro His Ser Lys Gln Gly Asn Lys
385                 390                 395                 400
Asn Asp Leu Glu Met Gly Ile Lys Ala Ala Arg Pro Glu Ile Ala Asp
                405                 410                 415
Arg Ala Thr Ser Glu Val Pro Gly Ser Gln Ala Ser Pro Asn Pro Val
            420                 425                 430
Pro Gly Asp Gly Leu His Arg Ala Gly Phe Asp Ala Phe Met Thr Gly
            435                 440                 445
Tyr Val Met Ala Tyr Val Glu Val Ser Gln Gly Pro Gln Pro Cys Ser
```

```
                   450              455               460
Ser Gly Pro Trp Leu Pro Glu Cys His Asn Lys Val Tyr Leu Ser Gly
465                 470                 475                 480

Lys Ala Val Pro Leu Thr Val Ala Lys Ser Gln Phe Ser Arg Ser Ser
                485                 490                 495

Lys Ala His Asn Gln Lys Met Lys Leu Thr Trp Gly Ser Ser
                500                 505                 510

<210> SEQ ID NO 2
<211> LENGTH: 315
<212> TYPE: PRT
<213> ORGANISM: Artificial Sequence
<220> FEATURE:
<223> OTHER INFORMATION: L196 Deletion mutant of TOE1

<400> SEQUENCE: 2

Leu Val Phe Leu Tyr Gln Asn Phe Tyr Ala His Leu Pro Glu Ser Leu
1               5                   10                  15

Gly Thr Phe Thr Ala Asp Leu Cys Glu Met Phe Pro Ala Gly Ile Tyr
            20                  25                  30

Asp Thr Lys Tyr Ala Ala Glu Phe His Ala Arg Phe Val Ala Ser Tyr
        35                  40                  45

Leu Glu Tyr Ala Phe Arg Lys Cys Glu Arg Glu Asn Gly Lys Gln Arg
    50                  55                  60

Ala Ala Gly Ser Pro His Leu Thr Leu Glu Phe Cys Asn Tyr Pro Ser
65                  70                  75                  80

Ser Met Arg Asp His Ile Asp Tyr Arg Cys Cys Leu Pro Pro Ala Thr
                85                  90                  95

His Arg Pro His Pro Thr Ser Ile Cys Asp Asn Phe Ser Ala Tyr Gly
            100                 105                 110

Trp Cys Pro Leu Gly Pro Gln Cys Pro Gln Ser His Asp Ile Asp Leu
        115                 120                 125

Ile Ile Asp Thr Asp Glu Ala Ala Glu Asp Lys Arg Arg Arg Arg Arg
    130                 135                 140

Arg Arg Arg Glu Lys Arg Lys Arg Ala Leu Leu Asn Leu Pro Gly Thr
145                 150                 155                 160

Gln Thr Ser Gly Glu Ala Lys Asp Gly Pro Pro Lys Lys Gln Val Cys
                165                 170                 175

Gly Asp Ser Ile Lys Pro Glu Glu Thr Glu Gln Glu Val Ala Ala Asp
            180                 185                 190

Glu Thr Arg Asn Leu Pro His Ser Lys Gln Gly Asn Lys Asn Asp Leu
        195                 200                 205

Glu Met Gly Ile Lys Ala Ala Arg Pro Glu Ile Ala Asp Arg Ala Thr
    210                 215                 220

Ser Glu Val Pro Gly Ser Gln Ala Ser Pro Asn Pro Val Pro Gly Asp
225                 230                 235                 240

Gly Leu His Arg Ala Gly Phe Asp Ala Phe Met Thr Gly Tyr Val Met
                245                 250                 255

Ala Tyr Val Glu Val Ser Gln Gly Pro Gln Pro Cys Ser Ser Gly Pro
            260                 265                 270

Trp Leu Pro Glu Cys His Asn Lys Val Tyr Leu Ser Gly Lys Ala Val
        275                 280                 285

Pro Leu Thr Val Ala Lys Ser Gln Phe Ser Arg Ser Ser Lys Ala His
    290                 295                 300

Asn Gln Lys Met Lys Leu Thr Trp Gly Ser Ser
            305                 310
```

<210> SEQ ID NO 3
<211> LENGTH: 221
<212> TYPE: PRT
<213> ORGANISM: Artificial Sequence
<220> FEATURE:
<223> OTHER INFORMATION: L196/D416 Deletion mutant of TOE1

<400> SEQUENCE: 3

```
Leu Val Phe Leu Tyr Gln Asn Phe Tyr Ala His Leu Pro Glu Ser Leu
1               5                   10                  15

Gly Thr Phe Thr Ala Asp Leu Cys Glu Met Phe Pro Ala Gly Ile Tyr
            20                  25                  30

Asp Thr Lys Tyr Ala Ala Glu Phe His Ala Arg Phe Val Ala Ser Tyr
        35                  40                  45

Leu Glu Tyr Ala Phe Arg Lys Cys Glu Arg Glu Asn Gly Lys Gln Arg
    50                  55                  60

Ala Ala Gly Ser Pro His Leu Thr Leu Glu Phe Cys Asn Tyr Pro Ser
65                  70                  75                  80

Ser Met Arg Asp His Ile Asp Tyr Arg Cys Cys Leu Pro Pro Ala Thr
                85                  90                  95

His Arg Pro His Pro Thr Ser Ile Cys Asp Asn Phe Ser Ala Tyr Gly
            100                 105                 110

Trp Cys Pro Leu Gly Pro Gln Cys Pro Gln Ser His Asp Ile Asp Leu
        115                 120                 125

Ile Ile Asp Thr Asp Glu Ala Ala Glu Asp Lys Arg Arg Arg
    130                 135                 140

Arg Arg Arg Glu Lys Arg Lys Arg Ala Leu Leu Asn Leu Pro Gly Thr
145                 150                 155                 160

Gln Thr Ser Gly Glu Ala Lys Asp Gly Pro Pro Lys Lys Gln Val Cys
                165                 170                 175

Gly Asp Ser Ile Lys Pro Glu Glu Thr Glu Gln Glu Val Ala Ala Asp
            180                 185                 190

Glu Thr Arg Asn Leu Pro His Ser Lys Gln Gly Asn Lys Asn Asp Leu
        195                 200                 205

Glu Met Gly Ile Lys Ala Ala Arg Pro Glu Ile Ala Asp
    210                 215                 220
```

<210> SEQ ID NO 4
<211> LENGTH: 207
<212> TYPE: PRT
<213> ORGANISM: Artificial Sequence
<220> FEATURE:
<223> OTHER INFORMATION: L196/D402 Deletion mutant of TOE1

<400> SEQUENCE: 4

```
Leu Val Phe Leu Tyr Gln Asn Phe Tyr Ala His Leu Pro Glu Ser Leu
1               5                   10                  15

Gly Thr Phe Thr Ala Asp Leu Cys Glu Met Phe Pro Ala Gly Ile Tyr
            20                  25                  30

Asp Thr Lys Tyr Ala Ala Glu Phe His Ala Arg Phe Val Ala Ser Tyr
        35                  40                  45

Leu Glu Tyr Ala Phe Arg Lys Cys Glu Arg Glu Asn Gly Lys Gln Arg
    50                  55                  60

Ala Ala Gly Ser Pro His Leu Thr Leu Glu Phe Cys Asn Tyr Pro Ser
65                  70                  75                  80
```

```
Ser Met Arg Asp His Ile Asp Tyr Arg Cys Cys Leu Pro Pro Ala Thr
                85                  90                  95

His Arg Pro His Pro Thr Ser Ile Cys Asp Asn Phe Ser Ala Tyr Gly
            100                 105                 110

Trp Cys Pro Leu Gly Pro Gln Cys Pro Gln Ser His Asp Ile Asp Leu
            115                 120                 125

Ile Ile Asp Thr Asp Glu Ala Ala Glu Asp Lys Arg Arg Arg
            130                 135             140

Arg Arg Arg Glu Lys Arg Lys Arg Ala Leu Leu Asn Leu Pro Gly Thr
145                 150                 155                 160

Gln Thr Ser Gly Glu Ala Lys Asp Gly Pro Pro Lys Lys Gln Val Cys
            165                 170                 175

Gly Asp Ser Ile Lys Pro Glu Glu Thr Glu Gln Glu Val Ala Ala Asp
            180                 185                 190

Glu Thr Arg Asn Leu Pro His Ser Lys Gln Gly Asn Lys Asn Asp
            195                 200                 205
```

<210> SEQ ID NO 5
<211> LENGTH: 192
<212> TYPE: PRT
<213> ORGANISM: Artificial Sequence
<220> FEATURE:
<223> OTHER INFORMATION: L196/D387 Deletion mutant of TOE1

<400> SEQUENCE: 5

```
Leu Val Phe Leu Tyr Gln Asn Phe Tyr Ala His Leu Pro Glu Ser Leu
1               5                   10                  15

Gly Thr Phe Thr Ala Asp Leu Cys Glu Met Phe Pro Ala Gly Ile Tyr
            20                  25                  30

Asp Thr Lys Tyr Ala Ala Glu Phe His Ala Arg Phe Val Ala Ser Tyr
            35                  40                  45

Leu Glu Tyr Ala Phe Arg Lys Cys Glu Arg Glu Asn Gly Lys Gln Arg
    50                  55                  60

Ala Ala Gly Ser Pro His Leu Thr Leu Glu Phe Cys Asn Tyr Pro Ser
65                  70                  75                  80

Ser Met Arg Asp His Ile Asp Tyr Arg Cys Cys Leu Pro Pro Ala Thr
                85                  90                  95

His Arg Pro His Pro Thr Ser Ile Cys Asp Asn Phe Ser Ala Tyr Gly
            100                 105                 110

Trp Cys Pro Leu Gly Pro Gln Cys Pro Gln Ser His Asp Ile Asp Leu
            115                 120                 125

Ile Ile Asp Thr Asp Glu Ala Ala Glu Asp Lys Arg Arg Arg
            130                 135             140

Arg Arg Arg Glu Lys Arg Lys Arg Ala Leu Leu Asn Leu Pro Gly Thr
145                 150                 155                 160

Gln Thr Ser Gly Glu Ala Lys Asp Gly Pro Pro Lys Lys Gln Val Cys
            165                 170                 175

Gly Asp Ser Ile Lys Pro Glu Glu Thr Glu Gln Glu Val Ala Ala Asp
            180                 185                 190
```

<210> SEQ ID NO 6
<211> LENGTH: 178
<212> TYPE: PRT
<213> ORGANISM: Artificial Sequence
<220> FEATURE:
<223> OTHER INFORMATION: L196/D373 Deletion mutant of TOE1

<400> SEQUENCE: 6

Leu Val Phe Leu Tyr Gln Asn Phe Tyr Ala His Leu Pro Glu Ser Leu
1               5                   10                  15

Gly Thr Phe Thr Ala Asp Leu Cys Glu Met Phe Pro Ala Gly Ile Tyr
                20                  25                  30

Asp Thr Lys Tyr Ala Ala Glu Phe His Ala Arg Phe Val Ala Ser Tyr
            35                  40                  45

Leu Glu Tyr Ala Phe Arg Lys Cys Glu Arg Glu Asn Gly Lys Gln Arg
        50                  55                  60

Ala Ala Gly Ser Pro His Leu Thr Leu Glu Phe Cys Asn Tyr Pro Ser
65                  70                  75                  80

Ser Met Arg Asp His Ile Asp Tyr Arg Cys Cys Leu Pro Pro Ala Thr
                85                  90                  95

His Arg Pro His Pro Thr Ser Ile Cys Asp Asn Phe Ser Ala Tyr Gly
                100                 105                 110

Trp Cys Pro Leu Gly Pro Gln Cys Pro Gln Ser His Asp Ile Asp Leu
            115                 120                 125

Ile Ile Asp Thr Asp Glu Ala Ala Ala Glu Asp Lys Arg Arg Arg Arg
        130                 135                 140

Arg Arg Arg Glu Lys Arg Lys Arg Ala Leu Leu Asn Leu Pro Gly Thr
145                 150                 155                 160

Gln Thr Ser Gly Glu Ala Lys Asp Gly Pro Pro Lys Lys Gln Val Cys
                165                 170                 175

Gly Asp

<210> SEQ ID NO 7
<211> LENGTH: 168
<212> TYPE: PRT
<213> ORGANISM: Artificial Sequence
<220> FEATURE:
<223> OTHER INFORMATION: L196/D363 Deletion mutant of TOE1

<400> SEQUENCE: 7

Leu Val Phe Leu Tyr Gln Asn Phe Tyr Ala His Leu Pro Glu Ser Leu
1               5                   10                  15

Gly Thr Phe Thr Ala Asp Leu Cys Glu Met Phe Pro Ala Gly Ile Tyr
                20                  25                  30

Asp Thr Lys Tyr Ala Ala Glu Phe His Ala Arg Phe Val Ala Ser Tyr
            35                  40                  45

Leu Glu Tyr Ala Phe Arg Lys Cys Glu Arg Glu Asn Gly Lys Gln Arg
        50                  55                  60

Ala Ala Gly Ser Pro His Leu Thr Leu Glu Phe Cys Asn Tyr Pro Ser
65                  70                  75                  80

Ser Met Arg Asp His Ile Asp Tyr Arg Cys Cys Leu Pro Pro Ala Thr
                85                  90                  95

His Arg Pro His Pro Thr Ser Ile Cys Asp Asn Phe Ser Ala Tyr Gly
                100                 105                 110

Trp Cys Pro Leu Gly Pro Gln Cys Pro Gln Ser His Asp Ile Asp Leu
            115                 120                 125

Ile Ile Asp Thr Asp Glu Ala Ala Ala Glu Asp Lys Arg Arg Arg Arg
        130                 135                 140

Arg Arg Arg Glu Lys Arg Lys Arg Ala Leu Leu Asn Leu Pro Gly Thr
145                 150                 155                 160

Gln Thr Ser Gly Glu Ala Lys Asp
                165

<210> SEQ ID NO 8
<211> LENGTH: 228
<212> TYPE: PRT
<213> ORGANISM: Artificial Sequence
<220> FEATURE:
<223> OTHER INFORMATION: Y283 Deletion mutant of TOE1

<400> SEQUENCE: 8

```
Tyr Arg Cys Cys Leu Pro Pro Ala Thr His Arg Pro His Pro Thr Ser
1               5                   10                  15

Ile Cys Asp Asn Phe Ser Ala Tyr Gly Trp Cys Pro Leu Gly Pro Gln
            20                  25                  30

Cys Pro Gln Ser His Asp Ile Asp Leu Ile Ile Asp Thr Asp Glu Ala
        35                  40                  45

Ala Ala Glu Asp Lys Arg Arg Arg Arg Arg Glu Lys Arg Lys
    50                  55                  60

Arg Ala Leu Leu Asn Leu Pro Gly Thr Gln Thr Ser Gly Glu Ala Lys
65                  70                  75                  80

Asp Gly Pro Pro Lys Lys Gln Val Cys Gly Asp Ser Ile Lys Pro Glu
                85                  90                  95

Glu Thr Glu Gln Glu Val Ala Ala Asp Glu Thr Arg Asn Leu Pro His
            100                 105                 110

Ser Lys Gln Gly Asn Lys Asn Asp Leu Glu Met Gly Ile Lys Ala Ala
        115                 120                 125

Arg Pro Glu Ile Ala Asp Arg Ala Thr Ser Glu Val Pro Gly Ser Gln
    130                 135                 140

Ala Ser Pro Asn Pro Val Pro Gly Asp Gly Leu His Arg Ala Gly Phe
145                 150                 155                 160

Asp Ala Phe Met Thr Gly Tyr Val Met Ala Tyr Val Glu Val Ser Gln
                165                 170                 175

Gly Pro Gln Pro Cys Ser Ser Gly Pro Trp Leu Pro Glu Cys His Asn
            180                 185                 190

Lys Val Tyr Leu Ser Gly Lys Ala Val Pro Leu Thr Val Ala Lys Ser
        195                 200                 205

Gln Phe Ser Arg Ser Ser Lys Ala His Asn Gln Lys Met Lys Leu Thr
    210                 215                 220

Trp Gly Ser Ser
225
```

<210> SEQ ID NO 9
<211> LENGTH: 134
<212> TYPE: PRT
<213> ORGANISM: Artificial Sequence
<220> FEATURE:
<223> OTHER INFORMATION: Y283/D416 Deletion mutant of TOE1

<400> SEQUENCE: 9

```
Tyr Arg Cys Cys Leu Pro Pro Ala Thr His Arg Pro His Pro Thr Ser
1               5                   10                  15

Ile Cys Asp Asn Phe Ser Ala Tyr Gly Trp Cys Pro Leu Gly Pro Gln
            20                  25                  30

Cys Pro Gln Ser His Asp Ile Asp Leu Ile Ile Asp Thr Asp Glu Ala
        35                  40                  45

Ala Ala Glu Asp Lys Arg Arg Arg Arg Arg Glu Lys Arg Lys
    50                  55                  60

Arg Ala Leu Leu Asn Leu Pro Gly Thr Gln Thr Ser Gly Glu Ala Lys
65                  70                  75                  80
```

Asp Gly Pro Pro Lys Lys Gln Val Cys Gly Asp Ser Ile Lys Pro Glu
                85                  90                  95

Glu Thr Glu Gln Glu Val Ala Ala Asp Glu Thr Arg Asn Leu Pro His
            100                 105                 110

Ser Lys Gln Gly Asn Lys Asn Asp Leu Glu Met Gly Ile Lys Ala Ala
        115                 120                 125

Arg Pro Glu Ile Ala Asp
    130

<210> SEQ ID NO 10
<211> LENGTH: 120
<212> TYPE: PRT
<213> ORGANISM: Artificial Sequence
<220> FEATURE:
<223> OTHER INFORMATION: Y283/D402 Deletion mutant of TOE1

<400> SEQUENCE: 10

Tyr Arg Cys Cys Leu Pro Pro Ala Thr His Arg Pro His Pro Thr Ser
1               5                   10                  15

Ile Cys Asp Asn Phe Ser Ala Tyr Gly Trp Cys Pro Leu Gly Pro Gln
            20                  25                  30

Cys Pro Gln Ser His Asp Ile Asp Leu Ile Ile Asp Thr Asp Glu Ala
        35                  40                  45

Ala Ala Glu Asp Lys Arg Arg Arg Arg Arg Arg Glu Lys Arg Lys
    50                  55                  60

Arg Ala Leu Leu Asn Leu Pro Gly Thr Gln Thr Ser Gly Glu Ala Lys
65                  70                  75                  80

Asp Gly Pro Pro Lys Lys Gln Val Cys Gly Asp Ser Ile Lys Pro Glu
                85                  90                  95

Glu Thr Glu Gln Glu Val Ala Ala Asp Glu Thr Arg Asn Leu Pro His
            100                 105                 110

Ser Lys Gln Gly Asn Lys Asn Asp
        115                 120

<210> SEQ ID NO 11
<211> LENGTH: 105
<212> TYPE: PRT
<213> ORGANISM: Artificial Sequence
<220> FEATURE:
<223> OTHER INFORMATION: Y283/D387 Deletion mutant of TOE1

<400> SEQUENCE: 11

Tyr Arg Cys Cys Leu Pro Pro Ala Thr His Arg Pro His Pro Thr Ser
1               5                   10                  15

Ile Cys Asp Asn Phe Ser Ala Tyr Gly Trp Cys Pro Leu Gly Pro Gln
            20                  25                  30

Cys Pro Gln Ser His Asp Ile Asp Leu Ile Ile Asp Thr Asp Glu Ala
        35                  40                  45

Ala Ala Glu Asp Lys Arg Arg Arg Arg Arg Arg Glu Lys Arg Lys
    50                  55                  60

Arg Ala Leu Leu Asn Leu Pro Gly Thr Gln Thr Ser Gly Glu Ala Lys
65                  70                  75                  80

Asp Gly Pro Pro Lys Lys Gln Val Cys Gly Asp Ser Ile Lys Pro Glu
                85                  90                  95

Glu Thr Glu Gln Glu Val Ala Ala Asp
            100                 105

<210> SEQ ID NO 12
<211> LENGTH: 91
<212> TYPE: PRT
<213> ORGANISM: Artificial Sequence
<220> FEATURE:
<223> OTHER INFORMATION: Y283/D373 Deletion mutant of TOE1

<400> SEQUENCE: 12

```
Tyr Arg Cys Cys Leu Pro Pro Ala Thr His Arg Pro His Pro Thr Ser
1               5                   10                  15

Ile Cys Asp Asn Phe Ser Ala Tyr Gly Trp Cys Pro Leu Gly Pro Gln
            20                  25                  30

Cys Pro Gln Ser His Asp Ile Asp Leu Ile Ile Asp Thr Asp Glu Ala
        35                  40                  45

Ala Ala Glu Asp Lys Arg Arg Arg Arg Arg Glu Lys Arg Lys
    50                  55                  60

Arg Ala Leu Leu Asn Leu Pro Gly Thr Gln Thr Ser Gly Glu Ala Lys
65                  70                  75                  80

Asp Gly Pro Pro Lys Lys Gln Val Cys Gly Asp
                85                  90
```

<210> SEQ ID NO 13
<211> LENGTH: 81
<212> TYPE: PRT
<213> ORGANISM: Artificial Sequence
<220> FEATURE:
<223> OTHER INFORMATION: Y283/D363 Deletion mutant of TOE1

<400> SEQUENCE: 13

```
Tyr Arg Cys Cys Leu Pro Pro Ala Thr His Arg Pro His Pro Thr Ser
1               5                   10                  15

Ile Cys Asp Asn Phe Ser Ala Tyr Gly Trp Cys Pro Leu Gly Pro Gln
            20                  25                  30

Cys Pro Gln Ser His Asp Ile Asp Leu Ile Ile Asp Thr Asp Glu Ala
        35                  40                  45

Ala Ala Glu Asp Lys Arg Arg Arg Arg Arg Glu Lys Arg Lys
    50                  55                  60

Arg Ala Leu Leu Asn Leu Pro Gly Thr Gln Thr Ser Gly Glu Ala Lys
65                  70                  75                  80

Asp
```

<210> SEQ ID NO 14
<211> LENGTH: 48
<212> TYPE: PRT
<213> ORGANISM: Artificial Sequence
<220> FEATURE:
<223> OTHER INFORMATION: C300/R347 Deletion mutant of TOE1

<400> SEQUENCE: 14

```
Cys Asp Asn Phe Ser Ala Tyr Gly Trp Cys Pro Leu Gly Pro Gln Cys
1               5                   10                  15

Pro Gln Ser His Asp Ile Asp Leu Ile Ile Asp Thr Asp Glu Ala Ala
            20                  25                  30

Ala Glu Asp Lys Arg Arg Arg Arg Arg Arg Glu Lys Arg Lys Arg
        35                  40                  45
```

<210> SEQ ID NO 15
<211> LENGTH: 13
<212> TYPE: PRT
<213> ORGANISM: Artificial Sequence
<220> FEATURE:

<223> OTHER INFORMATION: K335/R347 Deletion mutant of TOE1

<400> SEQUENCE: 15

Lys Arg Arg Arg Arg Arg Arg Glu Lys Arg Lys Arg
1               5                   10

<210> SEQ ID NO 16
<211> LENGTH: 64
<212> TYPE: PRT
<213> ORGANISM: Artificial Sequence
<220> FEATURE:
<223> OTHER INFORMATION: C300/D363 Deletion mutant of TOE1

<400> SEQUENCE: 16

Cys Asp Asn Phe Ser Ala Tyr Gly Trp Cys Pro Leu Gly Pro Gln Cys
1               5                   10                  15

Pro Gln Ser His Asp Ile Asp Leu Ile Ile Asp Thr Asp Glu Ala Ala
            20                  25                  30

Ala Glu Asp Lys Arg Arg Arg Arg Arg Arg Glu Lys Arg Lys Arg
        35                  40                  45

Ala Leu Leu Asn Leu Pro Gly Thr Gln Thr Ser Gly Glu Ala Lys Asp
    50                  55                  60

<210> SEQ ID NO 17
<211> LENGTH: 29
<212> TYPE: PRT
<213> ORGANISM: Artificial Sequence
<220> FEATURE:
<223> OTHER INFORMATION: K335/D363 Deletion mutant of TOE1

<400> SEQUENCE: 17

Lys Arg Arg Arg Arg Arg Arg Glu Lys Arg Lys Arg Ala Leu Leu
1               5                   10                  15

Asn Leu Pro Gly Thr Gln Thr Ser Gly Glu Ala Lys Asp
            20                  25

<210> SEQ ID NO 18
<211> LENGTH: 86
<212> TYPE: PRT
<213> ORGANISM: Human immunodeficiency virus 1

<400> SEQUENCE: 18

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Ala His Gln Asn Ser Gln Thr
    50                  55                  60

His Gln Ala Ser Leu Ser Lys Gln Pro Thr Ser Gln Pro Arg Gly Asp
65                  70                  75                  80

Pro Thr Gly Pro Lys Glu
                85

<210> SEQ ID NO 19
<211> LENGTH: 9
<212> TYPE: PRT
<213> ORGANISM: Artificial Sequence
<220> FEATURE:
<223> OTHER INFORMATION: Basic amino acid sequence region in Tat protein -continued

```
<400> SEQUENCE: 19

Arg Lys Lys Arg Arg Gln Arg Arg
1               5

<210> SEQ ID NO 20
<211> LENGTH: 13
<212> TYPE: PRT
<213> ORGANISM: Artificial Sequence
<220> FEATURE:
<223> OTHER INFORMATION: Basic amino acid sequence region in TOE1 protein

<400> SEQUENCE: 20

Lys Arg Arg Arg Arg Arg Arg Arg Glu Lys Arg Lys Arg
1               5                   10

<210> SEQ ID NO 21
<211> LENGTH: 39
<212> TYPE: PRT
<213> ORGANISM: Artificial Sequence
<220> FEATURE:
<223> OTHER INFORMATION: K335/D373 Deletion mutant of TOE1

<400> SEQUENCE: 21

Lys Arg Arg Arg Arg Arg Arg Arg Glu Lys Arg Lys Arg Ala Leu Leu
1               5                   10                  15

Asn Leu Pro Gly Thr Gln Thr Ser Gly Glu Ala Lys Asp Gly Pro Pro
            20                  25                  30

Lys Lys Gln Val Cys Gly Asp
        35

<210> SEQ ID NO 22
<211> LENGTH: 53
<212> TYPE: PRT
<213> ORGANISM: Artificial Sequence
<220> FEATURE:
<223> OTHER INFORMATION: K335/D387 Deletion mutant of TOE1

<400> SEQUENCE: 22

Lys Arg Arg Arg Arg Arg Arg Arg Glu Lys Arg Lys Arg Ala Leu Leu
1               5                   10                  15

Asn Leu Pro Gly Thr Gln Thr Ser Gly Glu Ala Lys Asp Gly Pro Pro
            20                  25                  30

Lys Lys Gln Val Cys Gly Asp Ser Ile Lys Pro Glu Glu Thr Glu Gln
        35                  40                  45

Glu Val Ala Ala Asp
    50

<210> SEQ ID NO 23
<211> LENGTH: 68
<212> TYPE: PRT
<213> ORGANISM: Artificial Sequence
<220> FEATURE:
<223> OTHER INFORMATION: K335/D402 Deletion mutant of TOE1

<400> SEQUENCE: 23

Lys Arg Arg Arg Arg Arg Arg Arg Glu Lys Arg Lys Arg Ala Leu Leu
1               5                   10                  15

Asn Leu Pro Gly Thr Gln Thr Ser Gly Glu Ala Lys Asp Gly Pro Pro
            20                  25                  30

Lys Lys Gln Val Cys Gly Asp Ser Ile Lys Pro Glu Glu Thr Glu Gln
        35                  40                  45

Glu Val Ala Ala Asp Glu Thr Arg Asn Leu Pro His Ser Lys Gln Gly
```

Asn Lys Asn Asp
65

<210> SEQ ID NO 24
<211> LENGTH: 82
<212> TYPE: PRT
<213> ORGANISM: Artificial Sequence
<220> FEATURE:
<223> OTHER INFORMATION: K335/D416 Deletion mutant of TOE1

<400> SEQUENCE: 24

Lys Arg Arg Arg Arg Arg Arg Glu Lys Arg Lys Arg Ala Leu Leu
1               5                   10                  15

Asn Leu Pro Gly Thr Gln Thr Ser Gly Glu Ala Lys Asp Gly Pro Pro
                20                  25                  30

Lys Lys Gln Val Cys Gly Asp Ser Ile Lys Pro Glu Glu Thr Glu Gln
            35                  40                  45

Glu Val Ala Ala Asp Glu Thr Arg Asn Leu Pro His Ser Lys Gln Gly
        50                  55                  60

Asn Lys Asn Asp Leu Glu Met Gly Ile Lys Ala Ala Arg Pro Glu Ile
65                  70                  75                  80

Ala Asp

<210> SEQ ID NO 25
<211> LENGTH: 101
<212> TYPE: PRT
<213> ORGANISM: Artificial Sequence
<220> FEATURE:
<223> OTHER INFORMATION: K335/D435 Deletion mutant of TOE1

<400> SEQUENCE: 25

Lys Arg Arg Arg Arg Arg Arg Glu Lys Arg Lys Arg Ala Leu Leu
1               5                   10                  15

Asn Leu Pro Gly Thr Gln Thr Ser Gly Glu Ala Lys Asp Gly Pro Pro
                20                  25                  30

Lys Lys Gln Val Cys Gly Asp Ser Ile Lys Pro Glu Glu Thr Glu Gln
            35                  40                  45

Glu Val Ala Ala Asp Glu Thr Arg Asn Leu Pro His Ser Lys Gln Gly
        50                  55                  60

Asn Lys Asn Asp Leu Glu Met Gly Ile Lys Ala Ala Arg Pro Glu Ile
65                  70                  75                  80

Ala Asp Arg Ala Thr Ser Glu Val Pro Gly Ser Gln Ala Ser Pro Asn
                85                  90                  95

Pro Val Pro Gly Asp
            100

<210> SEQ ID NO 26
<211> LENGTH: 109
<212> TYPE: PRT
<213> ORGANISM: Artificial Sequence
<220> FEATURE:
<223> OTHER INFORMATION: K335/D443 Deletion mutant of TOE1

<400> SEQUENCE: 26

Lys Arg Arg Arg Arg Arg Arg Glu Lys Arg Lys Arg Ala Leu Leu
1               5                   10                  15

Asn Leu Pro Gly Thr Gln Thr Ser Gly Glu Ala Lys Asp Gly Pro Pro
                20                  25                  30

Lys Lys Gln Val Cys Gly Asp Ser Ile Lys Pro Glu Glu Thr Glu Gln
            35                  40                  45

Glu Val Ala Ala Asp Glu Thr Arg Asn Leu Pro His Ser Lys Gln Gly
50                  55                  60

Asn Lys Asn Asp Leu Glu Met Gly Ile Lys Ala Ala Arg Pro Glu Ile
65                  70                  75                  80

Ala Asp Arg Ala Thr Ser Glu Val Pro Gly Ser Gln Ala Ser Pro Asn
                85                  90                  95

Pro Val Pro Gly Asp Gly Leu His Arg Ala Gly Phe Asp
                100                 105

<210> SEQ ID NO 27
<211> LENGTH: 176
<212> TYPE: PRT
<213> ORGANISM: Artificial Sequence
<220> FEATURE:
<223> OTHER INFORMATION: K335/S510 Deletion mutant of TOE1

<400> SEQUENCE: 27

Lys Arg Arg Arg Arg Arg Arg Glu Lys Arg Lys Arg Ala Leu Leu
1               5                   10                  15

Asn Leu Pro Gly Thr Gln Thr Ser Gly Glu Ala Lys Asp Gly Pro Pro
                20                  25                  30

Lys Lys Gln Val Cys Gly Asp Ser Ile Lys Pro Glu Glu Thr Glu Gln
            35                  40                  45

Glu Val Ala Ala Asp Glu Thr Arg Asn Leu Pro His Ser Lys Gln Gly
50                  55                  60

Asn Lys Asn Asp Leu Glu Met Gly Ile Lys Ala Ala Arg Pro Glu Ile
65                  70                  75                  80

Ala Asp Arg Ala Thr Ser Glu Val Pro Gly Ser Gln Ala Ser Pro Asn
                85                  90                  95

Pro Val Pro Gly Asp Gly Leu His Arg Ala Gly Phe Asp Ala Phe Met
                100                 105                 110

Thr Gly Tyr Val Met Ala Tyr Val Glu Val Ser Gln Gly Pro Gln Pro
            115                 120                 125

Cys Ser Ser Gly Pro Trp Leu Pro Glu Cys His Asn Lys Val Tyr Leu
        130                 135                 140

Ser Gly Lys Ala Val Pro Leu Thr Val Ala Lys Ser Gln Phe Ser Arg
145                 150                 155                 160

Ser Ser Lys Ala His Asn Gln Lys Met Lys Leu Thr Trp Gly Ser Ser
                165                 170                 175

<210> SEQ ID NO 28
<211> LENGTH: 35
<212> TYPE: PRT
<213> ORGANISM: Artificial Sequence
<220> FEATURE:
<223> OTHER INFORMATION: E329/D363 Deletion mutant of TOE1

<400> SEQUENCE: 28

Glu Ala Ala Ala Glu Asp Lys Arg Arg Arg Arg Arg Arg Glu Lys
1               5                   10                  15

Arg Lys Arg Ala Leu Leu Asn Leu Pro Gly Thr Gln Thr Ser Gly Glu
                20                  25                  30

Ala Lys Asp
        35

<210> SEQ ID NO 29

-continued

```
<211> LENGTH: 45
<212> TYPE: PRT
<213> ORGANISM: Artificial Sequence
<220> FEATURE:
<223> OTHER INFORMATION: E329/D373 Deletion mutant of TOE1

<400> SEQUENCE: 29

Glu Ala Ala Ala Glu Asp Lys Arg Arg Arg Arg Arg Arg Glu Lys
1               5                   10                  15

Arg Lys Arg Ala Leu Leu Asn Leu Pro Gly Thr Gln Thr Ser Gly Glu
            20                  25                  30

Ala Lys Asp Gly Pro Pro Lys Lys Gln Val Cys Gly Asp
        35                  40                  45

<210> SEQ ID NO 30
<211> LENGTH: 59
<212> TYPE: PRT
<213> ORGANISM: Artificial Sequence
<220> FEATURE:
<223> OTHER INFORMATION: E329/D387 Deletion mutant of TOE1

<400> SEQUENCE: 30

Glu Ala Ala Ala Glu Asp Lys Arg Arg Arg Arg Arg Arg Glu Lys
1               5                   10                  15

Arg Lys Arg Ala Leu Leu Asn Leu Pro Gly Thr Gln Thr Ser Gly Glu
            20                  25                  30

Ala Lys Asp Gly Pro Pro Lys Lys Gln Val Cys Gly Asp Ser Ile Lys
        35                  40                  45

Pro Glu Glu Thr Glu Gln Glu Val Ala Ala Asp
    50                  55

<210> SEQ ID NO 31
<211> LENGTH: 74
<212> TYPE: PRT
<213> ORGANISM: Artificial Sequence
<220> FEATURE:
<223> OTHER INFORMATION: E329/D402 Deletion mutant of TOE1

<400> SEQUENCE: 31

Glu Ala Ala Ala Glu Asp Lys Arg Arg Arg Arg Arg Arg Glu Lys
1               5                   10                  15

Arg Lys Arg Ala Leu Leu Asn Leu Pro Gly Thr Gln Thr Ser Gly Glu
            20                  25                  30

Ala Lys Asp Gly Pro Pro Lys Lys Gln Val Cys Gly Asp Ser Ile Lys
        35                  40                  45

Pro Glu Glu Thr Glu Gln Glu Val Ala Ala Asp Glu Thr Arg Asn Leu
    50                  55                  60

Pro His Ser Lys Gln Gly Asn Lys Asn Asp
65                  70

<210> SEQ ID NO 32
<211> LENGTH: 88
<212> TYPE: PRT
<213> ORGANISM: Artificial Sequence
<220> FEATURE:
<223> OTHER INFORMATION: E329/D416 Deletion mutant of TOE1

<400> SEQUENCE: 32

Glu Ala Ala Ala Glu Asp Lys Arg Arg Arg Arg Arg Arg Glu Lys
1               5                   10                  15

Arg Lys Arg Ala Leu Leu Asn Leu Pro Gly Thr Gln Thr Ser Gly Glu
            20                  25                  30
```

Ala Lys Asp Gly Pro Pro Lys Lys Gln Val Cys Gly Asp Ser Ile Lys
            35                  40                  45

Pro Glu Glu Thr Glu Gln Glu Val Ala Ala Asp Glu Thr Arg Asn Leu
    50                  55                  60

Pro His Ser Lys Gln Gly Asn Lys Asn Asp Leu Glu Met Gly Ile Lys
65                  70                  75                  80

Ala Ala Arg Pro Glu Ile Ala Asp
                85

<210> SEQ ID NO 33
<211> LENGTH: 107
<212> TYPE: PRT
<213> ORGANISM: Artificial Sequence
<220> FEATURE:
<223> OTHER INFORMATION: E329/D435 Deletion mutant of TOE1

<400> SEQUENCE: 33

Glu Ala Ala Ala Glu Asp Lys Arg Arg Arg Arg Arg Arg Arg Glu Lys
1               5                   10                  15

Arg Lys Arg Ala Leu Leu Asn Leu Pro Gly Thr Gln Thr Ser Gly Glu
            20                  25                  30

Ala Lys Asp Gly Pro Pro Lys Lys Gln Val Cys Gly Asp Ser Ile Lys
            35                  40                  45

Pro Glu Glu Thr Glu Gln Glu Val Ala Ala Asp Glu Thr Arg Asn Leu
    50                  55                  60

Pro His Ser Lys Gln Gly Asn Lys Asn Asp Leu Glu Met Gly Ile Lys
65                  70                  75                  80

Ala Ala Arg Pro Glu Ile Ala Asp Arg Ala Thr Ser Glu Val Pro Gly
                85                  90                  95

Ser Gln Ala Ser Pro Asn Pro Val Pro Gly Asp
            100                 105

<210> SEQ ID NO 34
<211> LENGTH: 115
<212> TYPE: PRT
<213> ORGANISM: Artificial Sequence
<220> FEATURE:
<223> OTHER INFORMATION: E329/D443 Deletion mutant of TOE1

<400> SEQUENCE: 34

Glu Ala Ala Ala Glu Asp Lys Arg Arg Arg Arg Arg Arg Arg Glu Lys
1               5                   10                  15

Arg Lys Arg Ala Leu Leu Asn Leu Pro Gly Thr Gln Thr Ser Gly Glu
            20                  25                  30

Ala Lys Asp Gly Pro Pro Lys Lys Gln Val Cys Gly Asp Ser Ile Lys
            35                  40                  45

Pro Glu Glu Thr Glu Gln Glu Val Ala Ala Asp Glu Thr Arg Asn Leu
    50                  55                  60

Pro His Ser Lys Gln Gly Asn Lys Asn Asp Leu Glu Met Gly Ile Lys
65                  70                  75                  80

Ala Ala Arg Pro Glu Ile Ala Asp Arg Ala Thr Ser Glu Val Pro Gly
                85                  90                  95

Ser Gln Ala Ser Pro Asn Pro Val Pro Gly Asp Gly Leu His Arg Ala
            100                 105                 110

Gly Phe Asp
        115

<210> SEQ ID NO 35
<211> LENGTH: 182
<212> TYPE: PRT
<213> ORGANISM: Artificial Sequence
<220> FEATURE:
<223> OTHER INFORMATION: E329/S510 Deletion mutant of TOE1

<400> SEQUENCE: 35

```
Glu Ala Ala Ala Glu Asp Lys Arg Arg Arg Arg Arg Arg Glu Lys
1               5                   10                  15

Arg Lys Arg Ala Leu Leu Asn Leu Pro Gly Thr Gln Thr Ser Gly Glu
            20                  25                  30

Ala Lys Asp Gly Pro Pro Lys Lys Gln Val Cys Gly Asp Ser Ile Lys
        35                  40                  45

Pro Glu Glu Thr Glu Gln Glu Val Ala Ala Asp Glu Thr Arg Asn Leu
    50                  55                  60

Pro His Ser Lys Gln Gly Asn Lys Asn Asp Leu Glu Met Gly Ile Lys
65                  70                  75                  80

Ala Ala Arg Pro Glu Ile Ala Asp Arg Ala Thr Ser Glu Val Pro Gly
                85                  90                  95

Ser Gln Ala Ser Pro Asn Pro Val Pro Gly Asp Gly Leu His Arg Ala
            100                 105                 110

Gly Phe Asp Ala Phe Met Thr Gly Tyr Val Met Ala Tyr Val Glu Val
        115                 120                 125

Ser Gln Gly Pro Gln Pro Cys Ser Ser Gly Pro Trp Leu Pro Glu Cys
    130                 135                 140

His Asn Lys Val Tyr Leu Ser Gly Lys Ala Val Pro Leu Thr Val Ala
145                 150                 155                 160

Lys Ser Gln Phe Ser Arg Ser Ser Lys Ala His Asn Gln Lys Met Lys
                165                 170                 175

Leu Thr Trp Gly Ser Ser
            180
```

<210> SEQ ID NO 36
<211> LENGTH: 41
<212> TYPE: PRT
<213> ORGANISM: Artificial Sequence
<220> FEATURE:
<223> OTHER INFORMATION: L323/D363 Deletion mutant of TOE1

<400> SEQUENCE: 36

```
Leu Ile Ile Asp Thr Asp Glu Ala Ala Ala Glu Asp Lys Arg Arg Arg
1               5                   10                  15

Arg Arg Arg Arg Glu Lys Arg Lys Arg Ala Leu Leu Asn Leu Pro Gly
            20                  25                  30

Thr Gln Thr Ser Gly Glu Ala Lys Asp
        35                  40
```

<210> SEQ ID NO 37
<211> LENGTH: 51
<212> TYPE: PRT
<213> ORGANISM: Artificial Sequence
<220> FEATURE:
<223> OTHER INFORMATION: L323/D373 Deletion mutant of TOE1

<400> SEQUENCE: 37

```
Leu Ile Ile Asp Thr Asp Glu Ala Ala Ala Glu Asp Lys Arg Arg Arg
1               5                   10                  15

Arg Arg Arg Arg Glu Lys Arg Lys Arg Ala Leu Leu Asn Leu Pro Gly
            20                  25                  30
```

```
Thr Gln Thr Ser Gly Glu Ala Lys Asp Gly Pro Pro Lys Lys Gln Val
        35                  40                  45

Cys Gly Asp
    50

<210> SEQ ID NO 38
<211> LENGTH: 65
<212> TYPE: PRT
<213> ORGANISM: Artificial Sequence
<220> FEATURE:
<223> OTHER INFORMATION: L323/D387 Deletion mutant of TOE1

<400> SEQUENCE: 38

Leu Ile Ile Asp Thr Asp Glu Ala Ala Ala Glu Asp Lys Arg Arg Arg
1               5                   10                  15

Arg Arg Arg Arg Glu Lys Arg Lys Arg Ala Leu Leu Asn Leu Pro Gly
                20                  25                  30

Thr Gln Thr Ser Gly Glu Ala Lys Asp Gly Pro Pro Lys Lys Gln Val
        35                  40                  45

Cys Gly Asp Ser Ile Lys Pro Glu Glu Thr Glu Gln Glu Val Ala Ala
    50                  55                  60

Asp
65

<210> SEQ ID NO 39
<211> LENGTH: 80
<212> TYPE: PRT
<213> ORGANISM: Artificial Sequence
<220> FEATURE:
<223> OTHER INFORMATION: L323/D402 Deletion mutant of TOE1

<400> SEQUENCE: 39

Leu Ile Ile Asp Thr Asp Glu Ala Ala Ala Glu Asp Lys Arg Arg Arg
1               5                   10                  15

Arg Arg Arg Arg Glu Lys Arg Lys Arg Ala Leu Leu Asn Leu Pro Gly
                20                  25                  30

Thr Gln Thr Ser Gly Glu Ala Lys Asp Gly Pro Pro Lys Lys Gln Val
        35                  40                  45

Cys Gly Asp Ser Ile Lys Pro Glu Glu Thr Glu Gln Glu Val Ala Ala
    50                  55                  60

Asp Glu Thr Arg Asn Leu Pro His Ser Lys Gln Gly Asn Lys Asn Asp
65                  70                  75                  80

<210> SEQ ID NO 40
<211> LENGTH: 94
<212> TYPE: PRT
<213> ORGANISM: Artificial Sequence
<220> FEATURE:
<223> OTHER INFORMATION: L323/D416 Deletion mutant of TOE1

<400> SEQUENCE: 40

Leu Ile Ile Asp Thr Asp Glu Ala Ala Ala Glu Asp Lys Arg Arg Arg
1               5                   10                  15

Arg Arg Arg Arg Glu Lys Arg Lys Arg Ala Leu Leu Asn Leu Pro Gly
                20                  25                  30

Thr Gln Thr Ser Gly Glu Ala Lys Asp Gly Pro Pro Lys Lys Gln Val
        35                  40                  45

Cys Gly Asp Ser Ile Lys Pro Glu Glu Thr Glu Gln Glu Val Ala Ala
    50                  55                  60
```

```
Asp Glu Thr Arg Asn Leu Pro His Ser Lys Gln Gly Asn Lys Asn Asp
 65                  70                  75                  80

Leu Glu Met Gly Ile Lys Ala Ala Arg Pro Glu Ile Ala Asp
                 85                  90
```

<210> SEQ ID NO 41
<211> LENGTH: 113
<212> TYPE: PRT
<213> ORGANISM: Artificial Sequence
<220> FEATURE:
<223> OTHER INFORMATION: L323/D435 Deletion mutant of TOE1

<400> SEQUENCE: 41

```
Leu Ile Ile Asp Thr Asp Glu Ala Ala Ala Glu Asp Lys Arg Arg Arg
 1               5                  10                  15

Arg Arg Arg Arg Glu Lys Arg Lys Arg Ala Leu Leu Asn Leu Pro Gly
                 20                  25                  30

Thr Gln Thr Ser Gly Glu Ala Lys Asp Gly Pro Pro Lys Lys Gln Val
             35                  40                  45

Cys Gly Asp Ser Ile Lys Pro Glu Glu Thr Glu Gln Glu Val Ala Ala
 50                  55                  60

Asp Glu Thr Arg Asn Leu Pro His Ser Lys Gln Gly Asn Lys Asn Asp
 65                  70                  75                  80

Leu Glu Met Gly Ile Lys Ala Ala Arg Pro Glu Ile Ala Asp Arg Ala
                 85                  90                  95

Thr Ser Glu Val Pro Gly Ser Gln Ala Ser Pro Asn Pro Val Pro Gly
            100                 105                 110

Asp
```

<210> SEQ ID NO 42
<211> LENGTH: 121
<212> TYPE: PRT
<213> ORGANISM: Artificial Sequence
<220> FEATURE:
<223> OTHER INFORMATION: L323/D443 Deletion mutant of TOE1

<400> SEQUENCE: 42

```
Leu Ile Ile Asp Thr Asp Glu Ala Ala Ala Glu Asp Lys Arg Arg Arg
 1               5                  10                  15

Arg Arg Arg Arg Glu Lys Arg Lys Arg Ala Leu Leu Asn Leu Pro Gly
                 20                  25                  30

Thr Gln Thr Ser Gly Glu Ala Lys Asp Gly Pro Pro Lys Lys Gln Val
             35                  40                  45

Cys Gly Asp Ser Ile Lys Pro Glu Glu Thr Glu Gln Glu Val Ala Ala
 50                  55                  60

Asp Glu Thr Arg Asn Leu Pro His Ser Lys Gln Gly Asn Lys Asn Asp
 65                  70                  75                  80

Leu Glu Met Gly Ile Lys Ala Ala Arg Pro Glu Ile Ala Asp Arg Ala
                 85                  90                  95

Thr Ser Glu Val Pro Gly Ser Gln Ala Ser Pro Asn Pro Val Pro Gly
            100                 105                 110

Asp Gly Leu His Arg Ala Gly Phe Asp
            115                 120
```

<210> SEQ ID NO 43
<211> LENGTH: 188
<212> TYPE: PRT
<213> ORGANISM: Artificial Sequence
<220> FEATURE:

<223> OTHER INFORMATION: L323/S510 Deletion mutant of TOE1

<400> SEQUENCE: 43

Leu Ile Ile Asp Thr Asp Glu Ala Ala Ala Glu Asp Lys Arg Arg
1               5                   10                  15

Arg Arg Arg Arg Glu Lys Arg Lys Arg Ala Leu Leu Asn Leu Pro Gly
            20                  25                  30

Thr Gln Thr Ser Gly Glu Ala Lys Asp Gly Pro Pro Lys Lys Gln Val
        35                  40                  45

Cys Gly Asp Ser Ile Lys Pro Glu Glu Thr Glu Gln Glu Val Ala Ala
50                  55                  60

Asp Glu Thr Arg Asn Leu Pro His Ser Lys Gln Gly Asn Lys Asn Asp
65                  70                  75                  80

Leu Glu Met Gly Ile Lys Ala Ala Arg Pro Glu Ile Ala Asp Arg Ala
                85                  90                  95

Thr Ser Glu Val Pro Gly Ser Gln Ala Ser Pro Asn Pro Val Pro Gly
            100                 105                 110

Asp Gly Leu His Arg Ala Gly Phe Asp Ala Phe Met Thr Gly Tyr Val
        115                 120                 125

Met Ala Tyr Val Glu Val Ser Gln Gly Pro Gln Pro Cys Ser Ser Gly
    130                 135                 140

Pro Trp Leu Pro Glu Cys His Asn Lys Val Tyr Leu Ser Gly Lys Ala
145                 150                 155                 160

Val Pro Leu Thr Val Ala Lys Ser Gln Phe Ser Arg Ser Ser Lys Ala
                165                 170                 175

His Asn Gln Lys Met Lys Leu Thr Trp Gly Ser Ser
            180                 185

<210> SEQ ID NO 44
<211> LENGTH: 43
<212> TYPE: PRT
<213> ORGANISM: Artificial Sequence
<220> FEATURE:
<223> OTHER INFORMATION: I321/D363 Deletion mutant of TOE1

<400> SEQUENCE: 44

Ile Asp Leu Ile Ile Asp Thr Asp Glu Ala Ala Ala Glu Asp Lys Arg
1               5                   10                  15

Arg Arg Arg Arg Arg Glu Lys Arg Lys Arg Ala Leu Leu Asn Leu
            20                  25                  30

Pro Gly Thr Gln Thr Ser Gly Glu Ala Lys Asp
        35                  40

<210> SEQ ID NO 45
<211> LENGTH: 53
<212> TYPE: PRT
<213> ORGANISM: Artificial Sequence
<220> FEATURE:
<223> OTHER INFORMATION: I321/D373 Deletion mutant of TOE1

<400> SEQUENCE: 45

Ile Asp Leu Ile Ile Asp Thr Asp Glu Ala Ala Ala Glu Asp Lys Arg
1               5                   10                  15

Arg Arg Arg Arg Arg Glu Lys Arg Lys Arg Ala Leu Leu Asn Leu
            20                  25                  30

Pro Gly Thr Gln Thr Ser Gly Glu Ala Lys Asp Gly Pro Pro Lys Lys
        35                  40                  45

Gln Val Cys Gly Asp

<210> SEQ ID NO 46
<211> LENGTH: 67
<212> TYPE: PRT
<213> ORGANISM: Artificial Sequence
<220> FEATURE:
<223> OTHER INFORMATION: I321/D387 Deletion mutant of TOE1

<400> SEQUENCE: 46

Ile Asp Leu Ile Ile Asp Thr Asp Glu Ala Ala Ala Glu Asp Lys Arg
1               5                   10                  15

Arg Arg Arg Arg Arg Arg Glu Lys Arg Lys Arg Ala Leu Leu Asn Leu
            20                  25                  30

Pro Gly Thr Gln Thr Ser Gly Glu Ala Lys Asp Gly Pro Pro Lys Lys
        35                  40                  45

Gln Val Cys Gly Asp Ser Ile Lys Pro Glu Glu Thr Glu Gln Glu Val
    50                  55                  60

Ala Ala Asp
65

<210> SEQ ID NO 47
<211> LENGTH: 82
<212> TYPE: PRT
<213> ORGANISM: Artificial Sequence
<220> FEATURE:
<223> OTHER INFORMATION: I321/D402 Deletion mutant of TOE1

<400> SEQUENCE: 47

Ile Asp Leu Ile Ile Asp Thr Asp Glu Ala Ala Ala Glu Asp Lys Arg
1               5                   10                  15

Arg Arg Arg Arg Arg Arg Glu Lys Arg Lys Arg Ala Leu Leu Asn Leu
            20                  25                  30

Pro Gly Thr Gln Thr Ser Gly Glu Ala Lys Asp Gly Pro Pro Lys Lys
        35                  40                  45

Gln Val Cys Gly Asp Ser Ile Lys Pro Glu Glu Thr Glu Gln Glu Val
    50                  55                  60

Ala Ala Asp Glu Thr Arg Asn Leu Pro His Ser Lys Gln Gly Asn Lys
65                  70                  75                  80

Asn Asp

<210> SEQ ID NO 48
<211> LENGTH: 96
<212> TYPE: PRT
<213> ORGANISM: Artificial Sequence
<220> FEATURE:
<223> OTHER INFORMATION: I321/D416 Deletion mutant of TOE1

<400> SEQUENCE: 48

Ile Asp Leu Ile Ile Asp Thr Asp Glu Ala Ala Ala Glu Asp Lys Arg
1               5                   10                  15

Arg Arg Arg Arg Arg Arg Glu Lys Arg Lys Arg Ala Leu Leu Asn Leu
            20                  25                  30

Pro Gly Thr Gln Thr Ser Gly Glu Ala Lys Asp Gly Pro Pro Lys Lys
        35                  40                  45

Gln Val Cys Gly Asp Ser Ile Lys Pro Glu Glu Thr Glu Gln Glu Val
    50                  55                  60

Ala Ala Asp Glu Thr Arg Asn Leu Pro His Ser Lys Gln Gly Asn Lys
65                  70                  75                  80

```
Asn Asp Leu Glu Met Gly Ile Lys Ala Ala Arg Pro Glu Ile Ala Asp
            85                  90                  95

<210> SEQ ID NO 49
<211> LENGTH: 115
<212> TYPE: PRT
<213> ORGANISM: Artificial Sequence
<220> FEATURE:
<223> OTHER INFORMATION: I321/D435 Deletion mutant of TOE1

<400> SEQUENCE: 49

Ile Asp Leu Ile Ile Asp Thr Asp Glu Ala Ala Ala Glu Asp Lys Arg
1               5                   10                  15

Arg Arg Arg Arg Arg Glu Lys Arg Lys Arg Ala Leu Leu Asn Leu
            20                  25                  30

Pro Gly Thr Gln Thr Ser Gly Glu Ala Lys Asp Gly Pro Pro Lys Lys
            35                  40                  45

Gln Val Cys Gly Asp Ser Ile Lys Pro Glu Glu Thr Glu Gln Glu Val
        50                  55                  60

Ala Ala Asp Glu Thr Arg Asn Leu Pro His Ser Lys Gln Gly Asn Lys
65                  70                  75                  80

Asn Asp Leu Glu Met Gly Ile Lys Ala Ala Arg Pro Glu Ile Ala Asp
            85                  90                  95

Arg Ala Thr Ser Glu Val Pro Gly Ser Gln Ala Ser Pro Asn Pro Val
                100                 105                 110

Pro Gly Asp
        115

<210> SEQ ID NO 50
<211> LENGTH: 123
<212> TYPE: PRT
<213> ORGANISM: Artificial Sequence
<220> FEATURE:
<223> OTHER INFORMATION: I321/D443 Deletion mutant of TOE1

<400> SEQUENCE: 50

Ile Asp Leu Ile Ile Asp Thr Asp Glu Ala Ala Ala Glu Asp Lys Arg
1               5                   10                  15

Arg Arg Arg Arg Arg Glu Lys Arg Lys Arg Ala Leu Leu Asn Leu
            20                  25                  30

Pro Gly Thr Gln Thr Ser Gly Glu Ala Lys Asp Gly Pro Pro Lys Lys
            35                  40                  45

Gln Val Cys Gly Asp Ser Ile Lys Pro Glu Glu Thr Glu Gln Glu Val
        50                  55                  60

Ala Ala Asp Glu Thr Arg Asn Leu Pro His Ser Lys Gln Gly Asn Lys
65                  70                  75                  80

Asn Asp Leu Glu Met Gly Ile Lys Ala Ala Arg Pro Glu Ile Ala Asp
            85                  90                  95

Arg Ala Thr Ser Glu Val Pro Gly Ser Gln Ala Ser Pro Asn Pro Val
                100                 105                 110

Pro Gly Asp Gly Leu His Arg Ala Gly Phe Asp
        115                 120

<210> SEQ ID NO 51
<211> LENGTH: 190
<212> TYPE: PRT
<213> ORGANISM: Artificial Sequence
<220> FEATURE:
<223> OTHER INFORMATION: I321/S510 Deletion mutant of TOE1
```

<400> SEQUENCE: 51

```
Ile Asp Leu Ile Ile Asp Thr Asp Glu Ala Ala Ala Glu Asp Lys Arg
1               5                   10                  15

Arg Arg Arg Arg Arg Arg Glu Lys Arg Lys Arg Ala Leu Leu Asn Leu
                20                  25                  30

Pro Gly Thr Gln Thr Ser Gly Glu Ala Lys Asp Gly Pro Lys Lys
            35                  40                  45

Gln Val Cys Gly Asp Ser Ile Lys Pro Glu Glu Thr Glu Gln Glu Val
    50                  55                  60

Ala Ala Asp Glu Thr Arg Asn Leu Pro His Ser Lys Gln Gly Asn Lys
65                  70                  75                  80

Asn Asp Leu Glu Met Gly Ile Lys Ala Ala Arg Pro Glu Ile Ala Asp
                85                  90                  95

Arg Ala Thr Ser Glu Val Pro Gly Ser Gln Ala Ser Pro Asn Pro Val
                100                 105                 110

Pro Gly Asp Gly Leu His Arg Ala Gly Phe Asp Ala Phe Met Thr Gly
            115                 120                 125

Tyr Val Met Ala Tyr Val Glu Val Ser Gln Gly Pro Gln Pro Cys Ser
    130                 135                 140

Ser Gly Pro Trp Leu Pro Glu Cys His Asn Lys Val Tyr Leu Ser Gly
145                 150                 155                 160

Lys Ala Val Pro Leu Thr Val Ala Lys Ser Gln Phe Ser Arg Ser Ser
                165                 170                 175

Lys Ala His Asn Gln Lys Met Lys Leu Thr Trp Gly Ser Ser
                180                 185                 190
```

<210> SEQ ID NO 52
<211> LENGTH: 62
<212> TYPE: PRT
<213> ORGANISM: Artificial Sequence
<220> FEATURE:
<223> OTHER INFORMATION: N302/D363 Deletion mutant of TOE1

<400> SEQUENCE: 52

```
Asn Phe Ser Ala Tyr Gly Trp Cys Pro Leu Gly Pro Gln Cys Pro Gln
1               5                   10                  15

Ser His Asp Ile Asp Leu Ile Ile Asp Thr Asp Glu Ala Ala Ala Glu
                20                  25                  30

Asp Lys Arg Arg Arg Arg Arg Arg Glu Lys Arg Lys Arg Ala Leu
            35                  40                  45

Leu Asn Leu Pro Gly Thr Gln Thr Ser Gly Glu Ala Lys Asp
    50                  55                  60
```

<210> SEQ ID NO 53
<211> LENGTH: 72
<212> TYPE: PRT
<213> ORGANISM: Artificial Sequence
<220> FEATURE:
<223> OTHER INFORMATION: N302/D373 Deletion mutant of TOE1

<400> SEQUENCE: 53

```
Asn Phe Ser Ala Tyr Gly Trp Cys Pro Leu Gly Pro Gln Cys Pro Gln
1               5                   10                  15

Ser His Asp Ile Asp Leu Ile Ile Asp Thr Asp Glu Ala Ala Ala Glu
                20                  25                  30

Asp Lys Arg Arg Arg Arg Arg Arg Glu Lys Arg Lys Arg Ala Leu
            35                  40                  45
```

Leu Asn Leu Pro Gly Thr Gln Thr Ser Gly Glu Ala Lys Asp Gly Pro
        50                  55                  60

Pro Lys Lys Gln Val Cys Gly Asp
65                  70

<210> SEQ ID NO 54
<211> LENGTH: 86
<212> TYPE: PRT
<213> ORGANISM: Artificial Sequence
<220> FEATURE:
<223> OTHER INFORMATION: N302/D387 Deletion mutant of TOE1

<400> SEQUENCE: 54

Asn Phe Ser Ala Tyr Gly Trp Cys Pro Leu Gly Pro Gln Cys Pro Gln
1               5                   10                  15

Ser His Asp Ile Asp Leu Ile Ile Asp Thr Asp Glu Ala Ala Ala Glu
            20                  25                  30

Asp Lys Arg Arg Arg Arg Arg Arg Glu Lys Arg Lys Arg Ala Leu
            35                  40                  45

Leu Asn Leu Pro Gly Thr Gln Thr Ser Gly Glu Ala Lys Asp Gly Pro
        50                  55                  60

Pro Lys Lys Gln Val Cys Gly Asp Ser Ile Lys Pro Glu Glu Thr Glu
65                  70                  75                  80

Gln Glu Val Ala Ala Asp
                85

<210> SEQ ID NO 55
<211> LENGTH: 101
<212> TYPE: PRT
<213> ORGANISM: Artificial Sequence
<220> FEATURE:
<223> OTHER INFORMATION: N302/D402 Deletion mutant of TOE1

<400> SEQUENCE: 55

Asn Phe Ser Ala Tyr Gly Trp Cys Pro Leu Gly Pro Gln Cys Pro Gln
1               5                   10                  15

Ser His Asp Ile Asp Leu Ile Ile Asp Thr Asp Glu Ala Ala Ala Glu
            20                  25                  30

Asp Lys Arg Arg Arg Arg Arg Arg Glu Lys Arg Lys Arg Ala Leu
            35                  40                  45

Leu Asn Leu Pro Gly Thr Gln Thr Ser Gly Glu Ala Lys Asp Gly Pro
        50                  55                  60

Pro Lys Lys Gln Val Cys Gly Asp Ser Ile Lys Pro Glu Glu Thr Glu
65                  70                  75                  80

Gln Glu Val Ala Ala Asp Glu Thr Arg Asn Leu Pro His Ser Lys Gln
                85                  90                  95

Gly Asn Lys Asn Asp
            100

<210> SEQ ID NO 56
<211> LENGTH: 115
<212> TYPE: PRT
<213> ORGANISM: Artificial Sequence
<220> FEATURE:
<223> OTHER INFORMATION: N302/D416 Deletion mutant of TOE1

<400> SEQUENCE: 56

Asn Phe Ser Ala Tyr Gly Trp Cys Pro Leu Gly Pro Gln Cys Pro Gln
1               5                   10                  15

Ser His Asp Ile Asp Leu Ile Ile Asp Thr Asp Glu Ala Ala Ala Glu

```
                  20                  25                  30

Asp Lys Arg Arg Arg Arg Arg Arg Glu Lys Arg Lys Arg Ala Leu
             35                  40                  45

Leu Asn Leu Pro Gly Thr Gln Thr Ser Gly Glu Ala Lys Asp Gly Pro
 50                  55                  60

Pro Lys Lys Gln Val Cys Gly Asp Ser Ile Lys Pro Glu Glu Thr Glu
 65                  70                  75                  80

Gln Glu Val Ala Ala Asp Glu Thr Arg Asn Leu Pro His Ser Lys Gln
                 85                  90                  95

Gly Asn Lys Asn Asp Leu Glu Met Gly Ile Lys Ala Ala Arg Pro Glu
                100                 105                 110

Ile Ala Asp
            115

<210> SEQ ID NO 57
<211> LENGTH: 134
<212> TYPE: PRT
<213> ORGANISM: Artificial Sequence
<220> FEATURE:
<223> OTHER INFORMATION: N302/D435 Deletion mutant of TOE1

<400> SEQUENCE: 57

Asn Phe Ser Ala Tyr Gly Trp Cys Pro Leu Gly Pro Gln Cys Pro Gln
 1               5                  10                  15

Ser His Asp Ile Asp Leu Ile Ile Asp Thr Asp Glu Ala Ala Ala Glu
                 20                  25                  30

Asp Lys Arg Arg Arg Arg Arg Arg Glu Lys Arg Lys Arg Ala Leu
             35                  40                  45

Leu Asn Leu Pro Gly Thr Gln Thr Ser Gly Glu Ala Lys Asp Gly Pro
 50                  55                  60

Pro Lys Lys Gln Val Cys Gly Asp Ser Ile Lys Pro Glu Glu Thr Glu
 65                  70                  75                  80

Gln Glu Val Ala Ala Asp Glu Thr Arg Asn Leu Pro His Ser Lys Gln
                 85                  90                  95

Gly Asn Lys Asn Asp Leu Glu Met Gly Ile Lys Ala Ala Arg Pro Glu
                100                 105                 110

Ile Ala Asp Arg Ala Thr Ser Glu Val Pro Gly Ser Gln Ala Ser Pro
            115                 120                 125

Asn Pro Val Pro Gly Asp
        130

<210> SEQ ID NO 58
<211> LENGTH: 142
<212> TYPE: PRT
<213> ORGANISM: Artificial Sequence
<220> FEATURE:
<223> OTHER INFORMATION: N302/D443 Deletion mutant of TOE1

<400> SEQUENCE: 58

Asn Phe Ser Ala Tyr Gly Trp Cys Pro Leu Gly Pro Gln Cys Pro Gln
 1               5                  10                  15

Ser His Asp Ile Asp Leu Ile Ile Asp Thr Asp Glu Ala Ala Ala Glu
                 20                  25                  30

Asp Lys Arg Arg Arg Arg Arg Arg Glu Lys Arg Lys Arg Ala Leu
             35                  40                  45

Leu Asn Leu Pro Gly Thr Gln Thr Ser Gly Glu Ala Lys Asp Gly Pro
 50                  55                  60
```

```
Pro Lys Lys Gln Val Cys Gly Asp Ser Ile Lys Pro Glu Glu Thr Glu
 65                  70                  75                  80

Gln Glu Val Ala Ala Asp Glu Thr Arg Asn Leu Pro His Ser Lys Gln
                 85                  90                  95

Gly Asn Lys Asn Asp Leu Glu Met Gly Ile Lys Ala Ala Arg Pro Glu
            100                 105                 110

Ile Ala Asp Arg Ala Thr Ser Glu Val Pro Gly Ser Gln Ala Ser Pro
        115                 120                 125

Asn Pro Val Pro Gly Asp Gly Leu His Arg Ala Gly Phe Asp
    130                 135                 140

<210> SEQ ID NO 59
<211> LENGTH: 209
<212> TYPE: PRT
<213> ORGANISM: Artificial Sequence
<220> FEATURE:
<223> OTHER INFORMATION: N302/S510 Deletion mutant of TOE1

<400> SEQUENCE: 59

Asn Phe Ser Ala Tyr Gly Trp Cys Pro Leu Gly Pro Gln Cys Pro Gln
1               5                   10                  15

Ser His Asp Ile Asp Leu Ile Ile Asp Thr Asp Glu Ala Ala Ala Glu
            20                  25                  30

Asp Lys Arg Arg Arg Arg Arg Arg Glu Lys Arg Lys Arg Ala Leu
        35                  40                  45

Leu Asn Leu Pro Gly Thr Gln Thr Ser Gly Glu Ala Lys Asp Gly Pro
 50                  55                  60

Pro Lys Lys Gln Val Cys Gly Asp Ser Ile Lys Pro Glu Glu Thr Glu
 65                  70                  75                  80

Gln Glu Val Ala Ala Asp Glu Thr Arg Asn Leu Pro His Ser Lys Gln
                 85                  90                  95

Gly Asn Lys Asn Asp Leu Glu Met Gly Ile Lys Ala Ala Arg Pro Glu
            100                 105                 110

Ile Ala Asp Arg Ala Thr Ser Glu Val Pro Gly Ser Gln Ala Ser Pro
        115                 120                 125

Asn Pro Val Pro Gly Asp Gly Leu His Arg Ala Gly Phe Asp Ala Phe
    130                 135                 140

Met Thr Gly Tyr Val Met Ala Tyr Val Glu Val Ser Gln Gly Pro Gln
145                 150                 155                 160

Pro Cys Ser Ser Gly Pro Trp Leu Pro Glu Cys His Asn Lys Val Tyr
                165                 170                 175

Leu Ser Gly Lys Ala Val Pro Leu Thr Val Ala Lys Ser Gln Phe Ser
            180                 185                 190

Arg Ser Ser Lys Ala His Asn Gln Lys Met Lys Leu Thr Trp Gly Ser
        195                 200                 205

Ser

<210> SEQ ID NO 60
<211> LENGTH: 153
<212> TYPE: PRT
<213> ORGANISM: Artificial Sequence
<220> FEATURE:
<223> OTHER INFORMATION: Y283/D435 Deletion mutant of TOE1

<400> SEQUENCE: 60

Tyr Arg Cys Cys Leu Pro Pro Ala Thr His Arg Pro His Pro Thr Ser
1               5                   10                  15
```

```
Ile Cys Asp Asn Phe Ser Ala Tyr Gly Trp Cys Leu Gly Pro Gln
         20                  25                  30

Cys Pro Gln Ser His Asp Ile Asp Leu Ile Ile Asp Thr Asp Glu Ala
             35                  40                  45

Ala Ala Glu Asp Lys Arg Arg Arg Arg Arg Glu Lys Arg Lys
65              55                  60

Arg Ala Leu Leu Asn Leu Pro Gly Thr Gln Thr Ser Gly Glu Ala Lys
65                  70                  75                  80

Asp Gly Pro Pro Lys Lys Gln Val Cys Gly Asp Ser Ile Lys Pro Glu
                 85                  90                  95

Glu Thr Glu Gln Glu Val Ala Ala Asp Glu Thr Arg Asn Leu Pro His
                100                 105                 110

Ser Lys Gln Gly Asn Lys Asn Asp Leu Glu Met Gly Ile Lys Ala Ala
            115                 120                 125

Arg Pro Glu Ile Ala Asp Arg Ala Thr Ser Glu Val Pro Gly Ser Gln
130                 135                 140

Ala Ser Pro Asn Pro Val Pro Gly Asp
145                 150
```

<210> SEQ ID NO 61
<211> LENGTH: 161
<212> TYPE: PRT
<213> ORGANISM: Artificial Sequence
<220> FEATURE:
<223> OTHER INFORMATION: Y283/D443 Deletion mutant of TOE1

<400> SEQUENCE: 61

```
Tyr Arg Cys Cys Leu Pro Pro Ala Thr His Arg Pro His Pro Thr Ser
1               5                   10                  15

Ile Cys Asp Asn Phe Ser Ala Tyr Gly Trp Cys Leu Gly Pro Gln
         20                  25                  30

Cys Pro Gln Ser His Asp Ile Asp Leu Ile Ile Asp Thr Asp Glu Ala
             35                  40                  45

Ala Ala Glu Asp Lys Arg Arg Arg Arg Arg Glu Lys Arg Lys
                55                  60

Arg Ala Leu Leu Asn Leu Pro Gly Thr Gln Thr Ser Gly Glu Ala Lys
65                  70                  75                  80

Asp Gly Pro Pro Lys Lys Gln Val Cys Gly Asp Ser Ile Lys Pro Glu
                85                  90                  95

Glu Thr Glu Gln Glu Val Ala Ala Asp Glu Thr Arg Asn Leu Pro His
                100                 105                 110

Ser Lys Gln Gly Asn Lys Asn Asp Leu Glu Met Gly Ile Lys Ala Ala
            115                 120                 125

Arg Pro Glu Ile Ala Asp Arg Ala Thr Ser Glu Val Pro Gly Ser Gln
130                 135                 140

Ala Ser Pro Asn Pro Val Pro Gly Asp Gly Leu His Arg Ala Gly Phe
145                 150                 155                 160

Asp
```

<210> SEQ ID NO 62
<211> LENGTH: 84
<212> TYPE: PRT
<213> ORGANISM: Artificial Sequence
<220> FEATURE:
<223> OTHER INFORMATION: H280/D363 Deletion mutant of TOE1

<400> SEQUENCE: 62

His Ile Asp Tyr Arg Cys Cys Leu Pro Pro Ala Thr His Arg Pro His
1               5                   10                  15

Pro Thr Ser Ile Cys Asp Asn Phe Ser Ala Tyr Gly Trp Cys Pro Leu
            20                  25                  30

Gly Pro Gln Cys Pro Gln Ser His Asp Ile Asp Leu Ile Ile Asp Thr
        35                  40                  45

Asp Glu Ala Ala Ala Glu Asp Lys Arg Arg Arg Arg Arg Arg Arg Glu
    50                  55                  60

Lys Arg Lys Arg Ala Leu Leu Asn Leu Pro Gly Thr Gln Thr Ser Gly
65                  70                  75                  80

Glu Ala Lys Asp

<210> SEQ ID NO 63
<211> LENGTH: 94
<212> TYPE: PRT
<213> ORGANISM: Artificial Sequence
<220> FEATURE:
<223> OTHER INFORMATION: H280/D373 Deletion mutant of TOE1

<400> SEQUENCE: 63

His Ile Asp Tyr Arg Cys Cys Leu Pro Pro Ala Thr His Arg Pro His
1               5                   10                  15

Pro Thr Ser Ile Cys Asp Asn Phe Ser Ala Tyr Gly Trp Cys Pro Leu
            20                  25                  30

Gly Pro Gln Cys Pro Gln Ser His Asp Ile Asp Leu Ile Ile Asp Thr
        35                  40                  45

Asp Glu Ala Ala Ala Glu Asp Lys Arg Arg Arg Arg Arg Arg Arg Glu
    50                  55                  60

Lys Arg Lys Arg Ala Leu Leu Asn Leu Pro Gly Thr Gln Thr Ser Gly
65                  70                  75                  80

Glu Ala Lys Asp Gly Pro Pro Lys Lys Gln Val Cys Gly Asp
                85                  90

<210> SEQ ID NO 64
<211> LENGTH: 108
<212> TYPE: PRT
<213> ORGANISM: Artificial Sequence
<220> FEATURE:
<223> OTHER INFORMATION: H280/D387 Deletion mutant of TOE1

<400> SEQUENCE: 64

His Ile Asp Tyr Arg Cys Cys Leu Pro Pro Ala Thr His Arg Pro His
1               5                   10                  15

Pro Thr Ser Ile Cys Asp Asn Phe Ser Ala Tyr Gly Trp Cys Pro Leu
            20                  25                  30

Gly Pro Gln Cys Pro Gln Ser His Asp Ile Asp Leu Ile Ile Asp Thr
        35                  40                  45

Asp Glu Ala Ala Ala Glu Asp Lys Arg Arg Arg Arg Arg Arg Arg Glu
    50                  55                  60

Lys Arg Lys Arg Ala Leu Leu Asn Leu Pro Gly Thr Gln Thr Ser Gly
65                  70                  75                  80

Glu Ala Lys Asp Gly Pro Pro Lys Lys Gln Val Cys Gly Asp Ser Ile
                85                  90                  95

Lys Pro Glu Glu Thr Glu Gln Glu Val Ala Ala Asp
                100                 105

<210> SEQ ID NO 65
<211> LENGTH: 123

```
<212> TYPE: PRT
<213> ORGANISM: Artificial Sequence
<220> FEATURE:
<223> OTHER INFORMATION: H280/D402 Deletion mutant of TOE1

<400> SEQUENCE: 65
```

His Ile Asp Tyr Arg Cys Cys Leu Pro Pro Ala Thr His Arg Pro His
1               5                   10                  15

Pro Thr Ser Ile Cys Asp Asn Phe Ser Ala Tyr Gly Trp Cys Pro Leu
            20                  25                  30

Gly Pro Gln Cys Pro Gln Ser His Asp Ile Asp Leu Ile Ile Asp Thr
        35                  40                  45

Asp Glu Ala Ala Ala Glu Asp Lys Arg Arg Arg Arg Arg Arg Arg Glu
    50                  55                  60

Lys Arg Lys Arg Ala Leu Leu Asn Leu Pro Gly Thr Gln Thr Ser Gly
65                  70                  75                  80

Glu Ala Lys Asp Gly Pro Pro Lys Lys Gln Val Cys Gly Asp Ser Ile
                85                  90                  95

Lys Pro Glu Glu Thr Glu Gln Glu Val Ala Ala Asp Glu Thr Arg Asn
            100                 105                 110

Leu Pro His Ser Lys Gln Gly Asn Lys Asn Asp
            115                 120

```
<210> SEQ ID NO 66
<211> LENGTH: 137
<212> TYPE: PRT
<213> ORGANISM: Artificial Sequence
<220> FEATURE:
<223> OTHER INFORMATION: H280/D416 Deletion mutant of TOE1

<400> SEQUENCE: 66
```

His Ile Asp Tyr Arg Cys Cys Leu Pro Pro Ala Thr His Arg Pro His
1               5                   10                  15

Pro Thr Ser Ile Cys Asp Asn Phe Ser Ala Tyr Gly Trp Cys Pro Leu
            20                  25                  30

Gly Pro Gln Cys Pro Gln Ser His Asp Ile Asp Leu Ile Ile Asp Thr
        35                  40                  45

Asp Glu Ala Ala Ala Glu Asp Lys Arg Arg Arg Arg Arg Arg Arg Glu
    50                  55                  60

Lys Arg Lys Arg Ala Leu Leu Asn Leu Pro Gly Thr Gln Thr Ser Gly
65                  70                  75                  80

Glu Ala Lys Asp Gly Pro Pro Lys Lys Gln Val Cys Gly Asp Ser Ile
                85                  90                  95

Lys Pro Glu Glu Thr Glu Gln Glu Val Ala Ala Asp Glu Thr Arg Asn
            100                 105                 110

Leu Pro His Ser Lys Gln Gly Asn Lys Asn Asp Leu Glu Met Gly Ile
            115                 120                 125

Lys Ala Ala Arg Pro Glu Ile Ala Asp
    130                 135

```
<210> SEQ ID NO 67
<211> LENGTH: 156
<212> TYPE: PRT
<213> ORGANISM: Artificial Sequence
<220> FEATURE:
<223> OTHER INFORMATION: H280/D435 Deletion mutant of TOE1

<400> SEQUENCE: 67
```

His Ile Asp Tyr Arg Cys Cys Leu Pro Pro Ala Thr His Arg Pro His

```
                1               5                  10                 15
            Pro Thr Ser Ile Cys Asp Asn Phe Ser Ala Tyr Gly Trp Cys Pro Leu
                           20                  25                 30

Gly Pro Gln Cys Pro Gln Ser His Asp Ile Asp Leu Ile Ile Asp Thr
                       35                  40                  45

Asp Glu Ala Ala Ala Glu Asp Lys Arg Arg Arg Arg Arg Arg Arg Glu
                   50                  55                  60

Lys Arg Lys Arg Ala Leu Leu Asn Leu Pro Gly Thr Gln Thr Ser Gly
            65                  70                  75                  80

Glu Ala Lys Asp Gly Pro Pro Lys Lys Gln Val Cys Gly Asp Ser Ile
                           85                  90                  95

Lys Pro Glu Glu Thr Glu Gln Glu Val Ala Ala Asp Glu Thr Arg Asn
                        100                 105                 110

Leu Pro His Ser Lys Gln Gly Asn Lys Asn Asp Leu Glu Met Gly Ile
                        115                 120                 125

Lys Ala Ala Arg Pro Glu Ile Ala Asp Arg Ala Thr Ser Glu Val Pro
                        130                 135                 140

Gly Ser Gln Ala Ser Pro Asn Pro Val Pro Gly Asp
            145                 150                 155
```

<210> SEQ ID NO 68
<211> LENGTH: 164
<212> TYPE: PRT
<213> ORGANISM: Artificial Sequence
<220> FEATURE:
<223> OTHER INFORMATION: H280/D443 Deletion mutant of TOE1

<400> SEQUENCE: 68

```
            His Ile Asp Tyr Arg Cys Cys Leu Pro Pro Ala Thr His Arg Pro His
            1               5                   10                  15

Pro Thr Ser Ile Cys Asp Asn Phe Ser Ala Tyr Gly Trp Cys Pro Leu
                           20                  25                 30

Gly Pro Gln Cys Pro Gln Ser His Asp Ile Asp Leu Ile Ile Asp Thr
                       35                  40                  45

Asp Glu Ala Ala Ala Glu Asp Lys Arg Arg Arg Arg Arg Arg Arg Glu
                   50                  55                  60

Lys Arg Lys Arg Ala Leu Leu Asn Leu Pro Gly Thr Gln Thr Ser Gly
            65                  70                  75                  80

Glu Ala Lys Asp Gly Pro Pro Lys Lys Gln Val Cys Gly Asp Ser Ile
                           85                  90                  95

Lys Pro Glu Glu Thr Glu Gln Glu Val Ala Ala Asp Glu Thr Arg Asn
                        100                 105                 110

Leu Pro His Ser Lys Gln Gly Asn Lys Asn Asp Leu Glu Met Gly Ile
                        115                 120                 125

Lys Ala Ala Arg Pro Glu Ile Ala Asp Arg Ala Thr Ser Glu Val Pro
                        130                 135                 140

Gly Ser Gln Ala Ser Pro Asn Pro Val Pro Gly Asp Gly Leu His Arg
            145                 150                 155                 160

Ala Gly Phe Asp
```

<210> SEQ ID NO 69
<211> LENGTH: 231
<212> TYPE: PRT
<213> ORGANISM: Artificial Sequence
<220> FEATURE:
<223> OTHER INFORMATION: H280/S510 Deletion mutant of TOE1

```
<400> SEQUENCE: 69

His Ile Asp Tyr Arg Cys Cys Leu Pro Pro Ala Thr His Arg Pro His
1               5                   10                  15

Pro Thr Ser Ile Cys Asp Asn Phe Ser Ala Tyr Gly Trp Cys Pro Leu
            20                  25                  30

Gly Pro Gln Cys Pro Gln Ser His Asp Ile Asp Leu Ile Ile Asp Thr
        35                  40                  45

Asp Glu Ala Ala Glu Asp Lys Arg Arg Arg Arg Arg Arg Arg Arg Glu
    50                  55                  60

Lys Arg Lys Arg Ala Leu Leu Asn Leu Pro Gly Thr Gln Thr Ser Gly
65                  70                  75                  80

Glu Ala Lys Asp Gly Pro Pro Lys Lys Gln Val Cys Gly Asp Ser Ile
                85                  90                  95

Lys Pro Glu Glu Thr Glu Gln Glu Val Ala Ala Asp Glu Thr Arg Asn
            100                 105                 110

Leu Pro His Ser Lys Gln Gly Asn Lys Asn Asp Leu Glu Met Gly Ile
        115                 120                 125

Lys Ala Ala Arg Pro Glu Ile Ala Asp Arg Ala Thr Ser Glu Val Pro
130                 135                 140

Gly Ser Gln Ala Ser Pro Asn Pro Val Pro Gly Asp Gly Leu His Arg
145                 150                 155                 160

Ala Gly Phe Asp Ala Phe Met Thr Gly Tyr Val Met Ala Tyr Val Glu
                165                 170                 175

Val Ser Gln Gly Pro Gln Pro Cys Ser Ser Gly Pro Trp Leu Pro Glu
            180                 185                 190

Cys His Asn Lys Val Tyr Leu Ser Gly Lys Ala Val Pro Leu Thr Val
        195                 200                 205

Ala Lys Ser Gln Phe Ser Arg Ser Ser Lys Ala His Asn Gln Lys Met
    210                 215                 220

Lys Leu Thr Trp Gly Ser Ser
225                 230

<210> SEQ ID NO 70
<211> LENGTH: 135
<212> TYPE: PRT
<213> ORGANISM: Artificial Sequence
<220> FEATURE:
<223> OTHER INFORMATION: T229/D363 Deletion mutant of TOE1

<400> SEQUENCE: 70

Thr Lys Tyr Ala Ala Glu Phe His Ala Arg Phe Val Ala Ser Tyr Leu
1               5                   10                  15

Glu Tyr Ala Phe Arg Lys Cys Glu Arg Glu Asn Gly Lys Gln Arg Ala
            20                  25                  30

Ala Gly Ser Pro His Leu Thr Leu Glu Phe Cys Asn Tyr Pro Ser Ser
        35                  40                  45

Met Arg Asp His Ile Asp Tyr Arg Cys Cys Leu Pro Pro Ala Thr His
    50                  55                  60

Arg Pro His Pro Thr Ser Ile Cys Asp Asn Phe Ser Ala Tyr Gly Trp
65                  70                  75                  80

Cys Pro Leu Gly Pro Gln Cys Pro Gln Ser His Asp Ile Asp Leu Ile
                85                  90                  95

Ile Asp Thr Asp Glu Ala Ala Ala Glu Asp Lys Arg Arg Arg Arg Arg
            100                 105                 110

Arg Arg Glu Lys Arg Lys Arg Ala Leu Leu Asn Leu Pro Gly Thr Gln
```

```
              115                 120                 125

Thr Ser Gly Glu Ala Lys Asp
    130                 135

<210> SEQ ID NO 71
<211> LENGTH: 145
<212> TYPE: PRT
<213> ORGANISM: Artificial Sequence
<220> FEATURE:
<223> OTHER INFORMATION: T229/D373 Deletion mutant of TOE1

<400> SEQUENCE: 71

Thr Lys Tyr Ala Ala Glu Phe His Ala Arg Phe Val Ala Ser Tyr Leu
1               5                   10                  15

Glu Tyr Ala Phe Arg Lys Cys Glu Arg Glu Asn Gly Lys Gln Arg Ala
            20                  25                  30

Ala Gly Ser Pro His Leu Thr Leu Glu Phe Cys Asn Tyr Pro Ser Ser
        35                  40                  45

Met Arg Asp His Ile Asp Tyr Arg Cys Cys Leu Pro Pro Ala Thr His
    50                  55                  60

Arg Pro His Pro Thr Ser Ile Cys Asp Asn Phe Ser Ala Tyr Gly Trp
65                  70                  75                  80

Cys Pro Leu Gly Pro Gln Cys Pro Gln Ser His Asp Ile Asp Leu Ile
                85                  90                  95

Ile Asp Thr Asp Glu Ala Ala Ala Glu Asp Lys Arg Arg Arg Arg Arg
            100                 105                 110

Arg Arg Glu Lys Arg Lys Arg Ala Leu Leu Asn Leu Pro Gly Thr Gln
        115                 120                 125

Thr Ser Gly Glu Ala Lys Asp Gly Pro Pro Lys Lys Gln Val Cys Gly
    130                 135                 140

Asp
145

<210> SEQ ID NO 72
<211> LENGTH: 159
<212> TYPE: PRT
<213> ORGANISM: Artificial Sequence
<220> FEATURE:
<223> OTHER INFORMATION: T229/D387 Deletion mutant of TOE1

<400> SEQUENCE: 72

Thr Lys Tyr Ala Ala Glu Phe His Ala Arg Phe Val Ala Ser Tyr Leu
1               5                   10                  15

Glu Tyr Ala Phe Arg Lys Cys Glu Arg Glu Asn Gly Lys Gln Arg Ala
            20                  25                  30

Ala Gly Ser Pro His Leu Thr Leu Glu Phe Cys Asn Tyr Pro Ser Ser
        35                  40                  45

Met Arg Asp His Ile Asp Tyr Arg Cys Cys Leu Pro Pro Ala Thr His
    50                  55                  60

Arg Pro His Pro Thr Ser Ile Cys Asp Asn Phe Ser Ala Tyr Gly Trp
65                  70                  75                  80

Cys Pro Leu Gly Pro Gln Cys Pro Gln Ser His Asp Ile Asp Leu Ile
                85                  90                  95

Ile Asp Thr Asp Glu Ala Ala Ala Glu Asp Lys Arg Arg Arg Arg Arg
            100                 105                 110

Arg Arg Glu Lys Arg Lys Arg Ala Leu Leu Asn Leu Pro Gly Thr Gln
        115                 120                 125
```

```
Thr Ser Gly Glu Ala Lys Asp Gly Pro Pro Lys Lys Gln Val Cys Gly
    130                 135                 140

Asp Ser Ile Lys Pro Glu Glu Thr Glu Gln Glu Val Ala Ala Asp
145                 150                 155
```

<210> SEQ ID NO 73
<211> LENGTH: 174
<212> TYPE: PRT
<213> ORGANISM: Artificial Sequence
<220> FEATURE:
<223> OTHER INFORMATION: T229/D402 Deletion mutant of TOE1

<400> SEQUENCE: 73

```
Thr Lys Tyr Ala Ala Glu Phe His Ala Arg Phe Val Ala Ser Tyr Leu
1               5                   10                  15

Glu Tyr Ala Phe Arg Lys Cys Glu Arg Glu Asn Gly Lys Gln Arg Ala
            20                  25                  30

Ala Gly Ser Pro His Leu Thr Leu Glu Phe Cys Asn Tyr Pro Ser Ser
        35                  40                  45

Met Arg Asp His Ile Asp Tyr Arg Cys Cys Leu Pro Pro Ala Thr His
    50                  55                  60

Arg Pro His Pro Thr Ser Ile Cys Asp Asn Phe Ser Ala Tyr Gly Trp
65                  70                  75                  80

Cys Pro Leu Gly Pro Gln Cys Pro Gln Ser His Asp Ile Asp Leu Ile
                85                  90                  95

Ile Asp Thr Asp Glu Ala Ala Ala Glu Asp Lys Arg Arg Arg Arg Arg
            100                 105                 110

Arg Arg Glu Lys Arg Lys Arg Ala Leu Leu Asn Leu Pro Gly Thr Gln
        115                 120                 125

Thr Ser Gly Glu Ala Lys Asp Gly Pro Pro Lys Lys Gln Val Cys Gly
    130                 135                 140

Asp Ser Ile Lys Pro Glu Glu Thr Glu Gln Glu Val Ala Ala Asp Glu
145                 150                 155                 160

Thr Arg Asn Leu Pro His Ser Lys Gln Gly Asn Lys Asn Asp
                165                 170
```

<210> SEQ ID NO 74
<211> LENGTH: 188
<212> TYPE: PRT
<213> ORGANISM: Artificial Sequence
<220> FEATURE:
<223> OTHER INFORMATION: T229/D416 Deletion mutant of TOE1

<400> SEQUENCE: 74

```
Thr Lys Tyr Ala Ala Glu Phe His Ala Arg Phe Val Ala Ser Tyr Leu
1               5                   10                  15

Glu Tyr Ala Phe Arg Lys Cys Glu Arg Glu Asn Gly Lys Gln Arg Ala
            20                  25                  30

Ala Gly Ser Pro His Leu Thr Leu Glu Phe Cys Asn Tyr Pro Ser Ser
        35                  40                  45

Met Arg Asp His Ile Asp Tyr Arg Cys Cys Leu Pro Pro Ala Thr His
    50                  55                  60

Arg Pro His Pro Thr Ser Ile Cys Asp Asn Phe Ser Ala Tyr Gly Trp
65                  70                  75                  80

Cys Pro Leu Gly Pro Gln Cys Pro Gln Ser His Asp Ile Asp Leu Ile
                85                  90                  95

Ile Asp Thr Asp Glu Ala Ala Ala Glu Asp Lys Arg Arg Arg Arg Arg
            100                 105                 110
```

```
Arg Arg Glu Lys Arg Lys Arg Ala Leu Leu Asn Leu Pro Gly Thr Gln
        115                 120                 125

Thr Ser Gly Glu Ala Lys Asp Gly Pro Pro Lys Lys Gln Val Cys Gly
    130                 135                 140

Asp Ser Ile Lys Pro Glu Glu Thr Glu Gln Glu Val Ala Ala Asp Glu
145                 150                 155                 160

Thr Arg Asn Leu Pro His Ser Lys Gln Gly Asn Lys Asn Asp Leu Glu
                165                 170                 175

Met Gly Ile Lys Ala Ala Arg Pro Glu Ile Ala Asp
                180                 185

<210> SEQ ID NO 75
<211> LENGTH: 207
<212> TYPE: PRT
<213> ORGANISM: Artificial Sequence
<220> FEATURE:
<223> OTHER INFORMATION: T229/D435 Deletion mutant of TOE1

<400> SEQUENCE: 75

Thr Lys Tyr Ala Ala Glu Phe His Ala Arg Phe Val Ala Ser Tyr Leu
1               5                   10                  15

Glu Tyr Ala Phe Arg Lys Cys Glu Arg Glu Asn Gly Lys Gln Arg Ala
                20                  25                  30

Ala Gly Ser Pro His Leu Thr Leu Glu Phe Cys Asn Tyr Pro Ser Ser
            35                  40                  45

Met Arg Asp His Ile Asp Tyr Arg Cys Cys Leu Pro Pro Ala Thr His
        50                  55                  60

Arg Pro His Pro Thr Ser Ile Cys Asp Asn Phe Ser Ala Tyr Gly Trp
65                  70                  75                  80

Cys Pro Leu Gly Pro Gln Cys Pro Gln Ser His Asp Ile Asp Leu Ile
                85                  90                  95

Ile Asp Thr Asp Glu Ala Ala Ala Glu Asp Lys Arg Arg Arg Arg Arg
                100                 105                 110

Arg Arg Glu Lys Arg Lys Arg Ala Leu Leu Asn Leu Pro Gly Thr Gln
        115                 120                 125

Thr Ser Gly Glu Ala Lys Asp Gly Pro Pro Lys Lys Gln Val Cys Gly
    130                 135                 140

Asp Ser Ile Lys Pro Glu Glu Thr Glu Gln Glu Val Ala Ala Asp Glu
145                 150                 155                 160

Thr Arg Asn Leu Pro His Ser Lys Gln Gly Asn Lys Asn Asp Leu Glu
                165                 170                 175

Met Gly Ile Lys Ala Ala Arg Pro Glu Ile Ala Asp Arg Ala Thr Ser
                180                 185                 190

Glu Val Pro Gly Ser Gln Ala Ser Pro Asn Pro Val Pro Gly Asp
            195                 200                 205

<210> SEQ ID NO 76
<211> LENGTH: 215
<212> TYPE: PRT
<213> ORGANISM: Artificial Sequence
<220> FEATURE:
<223> OTHER INFORMATION: T229/D443 Deletion mutant of TOE1

<400> SEQUENCE: 76

Thr Lys Tyr Ala Ala Glu Phe His Ala Arg Phe Val Ala Ser Tyr Leu
1               5                   10                  15

Glu Tyr Ala Phe Arg Lys Cys Glu Arg Glu Asn Gly Lys Gln Arg Ala
```

```
                20                  25                  30
Ala Gly Ser Pro His Leu Thr Leu Glu Phe Cys Asn Tyr Pro Ser Ser
            35                  40                  45

Met Arg Asp His Ile Asp Tyr Arg Cys Cys Leu Pro Pro Ala Thr His
 50                  55                  60

Arg Pro His Pro Thr Ser Ile Cys Asp Asn Phe Ser Ala Tyr Gly Trp
 65                  70                  75                  80

Cys Pro Leu Gly Pro Gln Cys Pro Gln Ser His Asp Ile Asp Leu Ile
                85                  90                  95

Ile Asp Thr Asp Glu Ala Ala Glu Asp Lys Arg Arg Arg Arg Arg Arg
            100                 105                 110

Arg Arg Glu Lys Arg Lys Arg Ala Leu Leu Asn Leu Pro Gly Thr Gln
            115                 120                 125

Thr Ser Gly Glu Ala Lys Asp Gly Pro Pro Lys Lys Gln Val Cys Gly
            130                 135                 140

Asp Ser Ile Lys Pro Glu Glu Thr Glu Gln Glu Val Ala Ala Asp Glu
145                 150                 155                 160

Thr Arg Asn Leu Pro His Ser Lys Gln Gly Asn Lys Asn Asp Leu Glu
                165                 170                 175

Met Gly Ile Lys Ala Ala Arg Pro Glu Ile Ala Asp Arg Ala Thr Ser
            180                 185                 190

Glu Val Pro Gly Ser Gln Ala Ser Pro Asn Pro Val Pro Gly Asp Gly
            195                 200                 205

Leu His Arg Ala Gly Phe Asp
            210                 215

<210> SEQ ID NO 77
<211> LENGTH: 282
<212> TYPE: PRT
<213> ORGANISM: Artificial Sequence
<220> FEATURE:
<223> OTHER INFORMATION: T229/S510 Deletion mutant of TOE1

<400> SEQUENCE: 77

Thr Lys Tyr Ala Ala Glu Phe His Ala Arg Phe Val Ala Ser Tyr Leu
1               5                  10                  15

Glu Tyr Ala Phe Arg Lys Cys Glu Arg Glu Asn Gly Lys Gln Arg Ala
            20                  25                  30

Ala Gly Ser Pro His Leu Thr Leu Glu Phe Cys Asn Tyr Pro Ser Ser
            35                  40                  45

Met Arg Asp His Ile Asp Tyr Arg Cys Cys Leu Pro Pro Ala Thr His
 50                  55                  60

Arg Pro His Pro Thr Ser Ile Cys Asp Asn Phe Ser Ala Tyr Gly Trp
 65                  70                  75                  80

Cys Pro Leu Gly Pro Gln Cys Pro Gln Ser His Asp Ile Asp Leu Ile
                85                  90                  95

Ile Asp Thr Asp Glu Ala Ala Glu Asp Lys Arg Arg Arg Arg Arg Arg
            100                 105                 110

Arg Arg Glu Lys Arg Lys Arg Ala Leu Leu Asn Leu Pro Gly Thr Gln
            115                 120                 125

Thr Ser Gly Glu Ala Lys Asp Gly Pro Pro Lys Lys Gln Val Cys Gly
            130                 135                 140

Asp Ser Ile Lys Pro Glu Glu Thr Glu Gln Glu Val Ala Ala Asp Glu
145                 150                 155                 160

Thr Arg Asn Leu Pro His Ser Lys Gln Gly Asn Lys Asn Asp Leu Glu
```

```
                    165                 170                 175
Met Gly Ile Lys Ala Ala Arg Pro Glu Ile Ala Asp Arg Ala Thr Ser
                180                 185                 190

Glu Val Pro Gly Ser Gln Ala Ser Pro Asn Pro Val Pro Gly Asp Gly
            195                 200                 205

Leu His Arg Ala Gly Phe Asp Ala Phe Met Thr Gly Tyr Val Met Ala
        210                 215                 220

Tyr Val Glu Val Ser Gln Gly Pro Gln Pro Cys Ser Ser Gly Pro Trp
225                 230                 235                 240

Leu Pro Glu Cys His Asn Lys Val Tyr Leu Ser Gly Lys Ala Val Pro
                245                 250                 255

Leu Thr Val Ala Lys Ser Gln Phe Ser Arg Ser Ser Lys Ala His Asn
            260                 265                 270

Gln Lys Met Lys Leu Thr Trp Gly Ser Ser
        275                 280

<210> SEQ ID NO 78
<211> LENGTH: 146
<212> TYPE: PRT
<213> ORGANISM: Artificial Sequence
<220> FEATURE:
<223> OTHER INFORMATION: L218/D363 Deletion mutant of TOE1

<400> SEQUENCE: 78

Leu Cys Glu Met Phe Pro Ala Gly Ile Tyr Asp Thr Lys Tyr Ala Ala
1               5                   10                  15

Glu Phe His Ala Arg Phe Val Ala Ser Tyr Leu Glu Tyr Ala Phe Arg
            20                  25                  30

Lys Cys Glu Arg Glu Asn Gly Lys Gln Arg Ala Ala Gly Ser Pro His
        35                  40                  45

Leu Thr Leu Glu Phe Cys Asn Tyr Pro Ser Ser Met Arg Asp His Ile
    50                  55                  60

Asp Tyr Arg Cys Cys Leu Pro Pro Ala Thr His Arg Pro His Pro Thr
65                  70                  75                  80

Ser Ile Cys Asp Asn Phe Ser Ala Tyr Gly Trp Cys Pro Leu Gly Pro
                85                  90                  95

Gln Cys Pro Gln Ser His Asp Ile Asp Leu Ile Ile Asp Thr Asp Glu
            100                 105                 110

Ala Ala Ala Glu Asp Lys Arg Arg Arg Arg Arg Glu Lys Arg
        115                 120                 125

Lys Arg Ala Leu Leu Asn Leu Pro Gly Thr Gln Thr Ser Gly Glu Ala
    130                 135                 140

Lys Asp
145

<210> SEQ ID NO 79
<211> LENGTH: 156
<212> TYPE: PRT
<213> ORGANISM: Artificial Sequence
<220> FEATURE:
<223> OTHER INFORMATION: L218/D373 Deletion mutant of TOE1

<400> SEQUENCE: 79

Leu Cys Glu Met Phe Pro Ala Gly Ile Tyr Asp Thr Lys Tyr Ala Ala
1               5                   10                  15

Glu Phe His Ala Arg Phe Val Ala Ser Tyr Leu Glu Tyr Ala Phe Arg
            20                  25                  30
```

Lys Cys Glu Arg Glu Asn Gly Lys Gln Arg Ala Ala Gly Ser Pro His
            35                  40                  45

Leu Thr Leu Glu Phe Cys Asn Tyr Pro Ser Ser Met Arg Asp His Ile
 50                  55                  60

Asp Tyr Arg Cys Cys Leu Pro Pro Ala Thr His Arg Pro His Pro Thr
 65                  70                  75                  80

Ser Ile Cys Asp Asn Phe Ser Ala Tyr Gly Trp Cys Pro Leu Gly Pro
                 85                  90                  95

Gln Cys Pro Gln Ser His Asp Ile Asp Leu Ile Ile Asp Thr Asp Glu
            100                 105                 110

Ala Ala Ala Glu Asp Lys Arg Arg Arg Arg Arg Glu Lys Arg
            115                 120                 125

Lys Arg Ala Leu Leu Asn Leu Pro Gly Thr Gln Thr Ser Gly Glu Ala
130                 135                 140

Lys Asp Gly Pro Pro Lys Lys Gln Val Cys Gly Asp
145                 150                 155

<210> SEQ ID NO 80
<211> LENGTH: 170
<212> TYPE: PRT
<213> ORGANISM: Artificial Sequence
<220> FEATURE:
<223> OTHER INFORMATION: L218/D387 Deletion mutant of TOE1

<400> SEQUENCE: 80

Leu Cys Glu Met Phe Pro Ala Gly Ile Tyr Asp Thr Lys Tyr Ala Ala
 1               5                   10                  15

Glu Phe His Ala Arg Phe Val Ala Ser Tyr Leu Glu Tyr Ala Phe Arg
                20                  25                  30

Lys Cys Glu Arg Glu Asn Gly Lys Gln Arg Ala Ala Gly Ser Pro His
            35                  40                  45

Leu Thr Leu Glu Phe Cys Asn Tyr Pro Ser Ser Met Arg Asp His Ile
 50                  55                  60

Asp Tyr Arg Cys Cys Leu Pro Pro Ala Thr His Arg Pro His Pro Thr
 65                  70                  75                  80

Ser Ile Cys Asp Asn Phe Ser Ala Tyr Gly Trp Cys Pro Leu Gly Pro
                 85                  90                  95

Gln Cys Pro Gln Ser His Asp Ile Asp Leu Ile Ile Asp Thr Asp Glu
            100                 105                 110

Ala Ala Ala Glu Asp Lys Arg Arg Arg Arg Arg Glu Lys Arg
            115                 120                 125

Lys Arg Ala Leu Leu Asn Leu Pro Gly Thr Gln Thr Ser Gly Glu Ala
130                 135                 140

Lys Asp Gly Pro Pro Lys Lys Gln Val Cys Gly Asp Ser Ile Lys Pro
145                 150                 155                 160

Glu Glu Thr Glu Gln Glu Val Ala Ala Asp
                165                 170

<210> SEQ ID NO 81
<211> LENGTH: 185
<212> TYPE: PRT
<213> ORGANISM: Artificial Sequence
<220> FEATURE:
<223> OTHER INFORMATION: L218/D402 Deletion mutant of TOE1

<400> SEQUENCE: 81

Leu Cys Glu Met Phe Pro Ala Gly Ile Tyr Asp Thr Lys Tyr Ala Ala
 1               5                   10                  15

```
Glu Phe His Ala Arg Phe Val Ala Ser Tyr Leu Glu Tyr Ala Phe Arg
            20                  25                  30

Lys Cys Glu Arg Glu Asn Gly Lys Gln Arg Ala Ala Gly Ser Pro His
        35                  40                  45

Leu Thr Leu Glu Phe Cys Asn Tyr Pro Ser Ser Met Arg Asp His Ile
    50                  55                  60

Asp Tyr Arg Cys Cys Leu Pro Pro Ala Thr His Arg Pro His Pro Thr
65                  70                  75                  80

Ser Ile Cys Asp Asn Phe Ser Ala Tyr Gly Trp Cys Pro Leu Gly Pro
                85                  90                  95

Gln Cys Pro Gln Ser His Asp Ile Asp Leu Ile Ile Asp Thr Asp Glu
            100                 105                 110

Ala Ala Ala Glu Asp Lys Arg Arg Arg Arg Arg Arg Glu Lys Arg
        115                 120                 125

Lys Arg Ala Leu Leu Asn Leu Pro Gly Thr Gln Thr Ser Gly Glu Ala
130                 135                 140

Lys Asp Gly Pro Pro Lys Lys Gln Val Cys Gly Asp Ser Ile Lys Pro
145                 150                 155                 160

Glu Glu Thr Glu Gln Glu Val Ala Ala Asp Glu Thr Arg Asn Leu Pro
                165                 170                 175

His Ser Lys Gln Gly Asn Lys Asn Asp
            180                 185

<210> SEQ ID NO 82
<211> LENGTH: 199
<212> TYPE: PRT
<213> ORGANISM: Artificial Sequence
<220> FEATURE:
<223> OTHER INFORMATION: L218/D416 Deletion mutant of TOE1

<400> SEQUENCE: 82

Leu Cys Glu Met Phe Pro Ala Gly Ile Tyr Asp Thr Lys Tyr Ala Ala
1               5                   10                  15

Glu Phe His Ala Arg Phe Val Ala Ser Tyr Leu Glu Tyr Ala Phe Arg
            20                  25                  30

Lys Cys Glu Arg Glu Asn Gly Lys Gln Arg Ala Ala Gly Ser Pro His
        35                  40                  45

Leu Thr Leu Glu Phe Cys Asn Tyr Pro Ser Ser Met Arg Asp His Ile
    50                  55                  60

Asp Tyr Arg Cys Cys Leu Pro Pro Ala Thr His Arg Pro His Pro Thr
65                  70                  75                  80

Ser Ile Cys Asp Asn Phe Ser Ala Tyr Gly Trp Cys Pro Leu Gly Pro
                85                  90                  95

Gln Cys Pro Gln Ser His Asp Ile Asp Leu Ile Ile Asp Thr Asp Glu
            100                 105                 110

Ala Ala Ala Glu Asp Lys Arg Arg Arg Arg Arg Arg Glu Lys Arg
        115                 120                 125

Lys Arg Ala Leu Leu Asn Leu Pro Gly Thr Gln Thr Ser Gly Glu Ala
130                 135                 140

Lys Asp Gly Pro Pro Lys Lys Gln Val Cys Gly Asp Ser Ile Lys Pro
145                 150                 155                 160

Glu Glu Thr Glu Gln Glu Val Ala Ala Asp Glu Thr Arg Asn Leu Pro
                165                 170                 175

His Ser Lys Gln Gly Asn Lys Asn Asp Leu Glu Met Gly Ile Lys Ala
            180                 185                 190
```

```
Ala Arg Pro Glu Ile Ala Asp
        195

<210> SEQ ID NO 83
<211> LENGTH: 218
<212> TYPE: PRT
<213> ORGANISM: Artificial Sequence
<220> FEATURE:
<223> OTHER INFORMATION: L218/D435 Deletion mutant of TOE1

<400> SEQUENCE: 83

Leu Cys Glu Met Phe Pro Ala Gly Ile Tyr Asp Thr Lys Tyr Ala Ala
1               5                   10                  15

Glu Phe His Ala Arg Phe Val Ala Ser Tyr Leu Glu Tyr Ala Phe Arg
            20                  25                  30

Lys Cys Glu Arg Glu Asn Gly Lys Gln Arg Ala Ala Gly Ser Pro His
        35                  40                  45

Leu Thr Leu Glu Phe Cys Asn Tyr Pro Ser Ser Met Arg Asp His Ile
    50                  55                  60

Asp Tyr Arg Cys Cys Leu Pro Pro Ala Thr His Arg Pro His Pro Thr
65                  70                  75                  80

Ser Ile Cys Asp Asn Phe Ser Ala Tyr Gly Trp Cys Pro Leu Gly Pro
                85                  90                  95

Gln Cys Pro Gln Ser His Asp Ile Asp Leu Ile Asp Thr Asp Glu
            100                 105                 110

Ala Ala Ala Glu Asp Lys Arg Arg Arg Arg Arg Arg Glu Lys Arg
        115                 120                 125

Lys Arg Ala Leu Leu Asn Leu Pro Gly Thr Gln Thr Ser Gly Glu Ala
130                 135                 140

Lys Asp Gly Pro Pro Lys Lys Gln Val Cys Gly Asp Ser Ile Lys Pro
145                 150                 155                 160

Glu Glu Thr Glu Gln Glu Val Ala Ala Asp Glu Thr Arg Asn Leu Pro
                165                 170                 175

His Ser Lys Gln Gly Asn Lys Asn Asp Leu Glu Met Gly Ile Lys Ala
            180                 185                 190

Ala Arg Pro Glu Ile Ala Asp Arg Ala Thr Ser Glu Val Pro Gly Ser
        195                 200                 205

Gln Ala Ser Pro Asn Pro Val Pro Gly Asp
    210                 215

<210> SEQ ID NO 84
<211> LENGTH: 226
<212> TYPE: PRT
<213> ORGANISM: Artificial Sequence
<220> FEATURE:
<223> OTHER INFORMATION: L218/D443 Deletion mutant of TOE1

<400> SEQUENCE: 84

Leu Cys Glu Met Phe Pro Ala Gly Ile Tyr Asp Thr Lys Tyr Ala Ala
1               5                   10                  15

Glu Phe His Ala Arg Phe Val Ala Ser Tyr Leu Glu Tyr Ala Phe Arg
            20                  25                  30

Lys Cys Glu Arg Glu Asn Gly Lys Gln Arg Ala Ala Gly Ser Pro His
        35                  40                  45

Leu Thr Leu Glu Phe Cys Asn Tyr Pro Ser Ser Met Arg Asp His Ile
    50                  55                  60

Asp Tyr Arg Cys Cys Leu Pro Pro Ala Thr His Arg Pro His Pro Thr
```

```
                65                  70                  75                  80
Ser Ile Cys Asp Asn Phe Ser Ala Tyr Gly Trp Cys Pro Leu Gly Pro
                    85                  90                  95

Gln Cys Pro Gln Ser His Asp Ile Asp Leu Ile Ile Asp Thr Asp Glu
                100                 105                 110

Ala Ala Ala Glu Asp Lys Arg Arg Arg Arg Arg Arg Glu Lys Arg
            115                 120                 125

Lys Arg Ala Leu Leu Asn Leu Pro Gly Thr Gln Thr Ser Gly Glu Ala
130                 135                 140

Lys Asp Gly Pro Pro Lys Lys Gln Val Cys Gly Asp Ser Ile Lys Pro
145                 150                 155                 160

Glu Glu Thr Glu Gln Glu Val Ala Ala Asp Glu Thr Arg Asn Leu Pro
                165                 170                 175

His Ser Lys Gln Gly Asn Lys Asn Asp Leu Glu Met Gly Ile Lys Ala
                180                 185                 190

Ala Arg Pro Glu Ile Ala Asp Arg Ala Thr Ser Glu Val Pro Gly Ser
            195                 200                 205

Gln Ala Ser Pro Asn Pro Val Pro Gly Asp Gly Leu His Arg Ala Gly
            210                 215                 220

Phe Asp
225

<210> SEQ ID NO 85
<211> LENGTH: 293
<212> TYPE: PRT
<213> ORGANISM: Artificial Sequence
<220> FEATURE:
<223> OTHER INFORMATION: L218/S510 Deletion mutant of TOE1

<400> SEQUENCE: 85

Leu Cys Glu Met Phe Pro Ala Gly Ile Tyr Asp Thr Lys Tyr Ala Ala
1               5                   10                  15

Glu Phe His Ala Arg Phe Val Ala Ser Tyr Leu Glu Tyr Ala Phe Arg
                20                  25                  30

Lys Cys Glu Arg Glu Asn Gly Lys Gln Arg Ala Ala Gly Ser Pro His
            35                  40                  45

Leu Thr Leu Glu Phe Cys Asn Tyr Pro Ser Ser Met Arg Asp His Ile
50                  55                  60

Asp Tyr Arg Cys Cys Leu Pro Pro Ala Thr His Arg Pro His Pro Thr
65                  70                  75                  80

Ser Ile Cys Asp Asn Phe Ser Ala Tyr Gly Trp Cys Pro Leu Gly Pro
                    85                  90                  95

Gln Cys Pro Gln Ser His Asp Ile Asp Leu Ile Ile Asp Thr Asp Glu
                100                 105                 110

Ala Ala Ala Glu Asp Lys Arg Arg Arg Arg Arg Arg Glu Lys Arg
            115                 120                 125

Lys Arg Ala Leu Leu Asn Leu Pro Gly Thr Gln Thr Ser Gly Glu Ala
130                 135                 140

Lys Asp Gly Pro Pro Lys Lys Gln Val Cys Gly Asp Ser Ile Lys Pro
145                 150                 155                 160

Glu Glu Thr Glu Gln Glu Val Ala Ala Asp Glu Thr Arg Asn Leu Pro
                165                 170                 175

His Ser Lys Gln Gly Asn Lys Asn Asp Leu Glu Met Gly Ile Lys Ala
                180                 185                 190

Ala Arg Pro Glu Ile Ala Asp Arg Ala Thr Ser Glu Val Pro Gly Ser
```

```
                    195                 200                 205
Gln Ala Ser Pro Asn Pro Val Pro Gly Asp Gly Leu His Arg Ala Gly
210                 215                 220

Phe Asp Ala Phe Met Thr Gly Tyr Val Met Ala Tyr Val Glu Val Ser
225                 230                 235                 240

Gln Gly Pro Gln Pro Cys Ser Ser Gly Pro Trp Leu Pro Glu Cys His
                245                 250                 255

Asn Lys Val Tyr Leu Ser Gly Lys Ala Val Pro Leu Thr Val Ala Lys
                260                 265                 270

Ser Gln Phe Ser Arg Ser Ser Lys Ala His Asn Gln Lys Met Lys Leu
                275                 280                 285

Thr Trp Gly Ser Ser
                290

<210> SEQ ID NO 86
<211> LENGTH: 240
<212> TYPE: PRT
<213> ORGANISM: Artificial Sequence
<220> FEATURE:
<223> OTHER INFORMATION: L196/D435 Deletion mutant of TOE1

<400> SEQUENCE: 86

Leu Val Phe Leu Tyr Gln Asn Phe Tyr Ala His Leu Pro Glu Ser Leu
1               5                   10                  15

Gly Thr Phe Thr Ala Asp Leu Cys Glu Met Phe Pro Ala Gly Ile Tyr
                20                  25                  30

Asp Thr Lys Tyr Ala Ala Glu Phe His Ala Arg Phe Val Ala Ser Tyr
            35                  40                  45

Leu Glu Tyr Ala Phe Arg Lys Cys Glu Arg Glu Asn Gly Lys Gln Arg
    50                  55                  60

Ala Ala Gly Ser Pro His Leu Thr Leu Glu Phe Cys Asn Tyr Pro Ser
65                  70                  75                  80

Ser Met Arg Asp His Ile Asp Tyr Arg Cys Cys Leu Pro Pro Ala Thr
                85                  90                  95

His Arg Pro His Pro Thr Ser Ile Cys Asp Asn Phe Ser Ala Tyr Gly
            100                 105                 110

Trp Cys Pro Leu Gly Pro Gln Cys Pro Gln Ser His Asp Ile Asp Leu
        115                 120                 125

Ile Ile Asp Thr Asp Glu Ala Ala Glu Asp Lys Arg Arg Arg Arg
    130                 135                 140

Arg Arg Arg Glu Lys Arg Lys Arg Ala Leu Leu Asn Leu Pro Gly Thr
145                 150                 155                 160

Gln Thr Ser Gly Glu Ala Lys Asp Gly Pro Lys Lys Gln Val Cys
                165                 170                 175

Gly Asp Ser Ile Lys Pro Glu Glu Thr Glu Gln Val Ala Ala Asp
            180                 185                 190

Glu Thr Arg Asn Leu Pro His Ser Lys Gln Gly Asn Lys Asn Asp Leu
    195                 200                 205

Glu Met Gly Ile Lys Ala Ala Arg Pro Glu Ile Ala Asp Arg Ala Thr
    210                 215                 220

Ser Glu Val Pro Gly Ser Gln Ala Ser Pro Asn Pro Val Pro Gly Asp
225                 230                 235                 240

<210> SEQ ID NO 87
<211> LENGTH: 248
<212> TYPE: PRT
```

```
<213> ORGANISM: Artificial Sequence
<220> FEATURE:
<223> OTHER INFORMATION: L196/D443 Deletion mutant of TOE1

<400> SEQUENCE: 87

Leu Val Phe Leu Tyr Gln Asn Phe Tyr Ala His Leu Pro Glu Ser Leu
1               5                   10                  15

Gly Thr Phe Thr Ala Asp Leu Cys Glu Met Phe Pro Ala Gly Ile Tyr
            20                  25                  30

Asp Thr Lys Tyr Ala Ala Glu Phe His Ala Arg Phe Val Ala Ser Tyr
        35                  40                  45

Leu Glu Tyr Ala Phe Arg Lys Cys Glu Arg Glu Asn Gly Lys Gln Arg
    50                  55                  60

Ala Ala Gly Ser Pro His Leu Thr Leu Glu Phe Cys Asn Tyr Pro Ser
65                  70                  75                  80

Ser Met Arg Asp His Ile Asp Tyr Arg Cys Cys Leu Pro Pro Ala Thr
                85                  90                  95

His Arg Pro His Pro Thr Ser Ile Cys Asp Asn Phe Ser Ala Tyr Gly
            100                 105                 110

Trp Cys Pro Leu Gly Pro Gln Cys Pro Gln Ser His Asp Ile Asp Leu
        115                 120                 125

Ile Ile Asp Thr Asp Glu Ala Ala Glu Asp Lys Arg Arg Arg Arg Arg
130                 135                 140

Arg Arg Arg Glu Lys Arg Lys Arg Ala Leu Leu Asn Leu Pro Gly Thr
145                 150                 155                 160

Gln Thr Ser Gly Glu Ala Lys Asp Gly Pro Pro Lys Lys Gln Val Cys
                165                 170                 175

Gly Asp Ser Ile Lys Pro Glu Glu Thr Glu Gln Glu Val Ala Ala Asp
            180                 185                 190

Glu Thr Arg Asn Leu Pro His Ser Lys Gln Gly Asn Lys Asn Asp Leu
        195                 200                 205

Glu Met Gly Ile Lys Ala Ala Arg Pro Gly Ile Ala Asp Arg Ala Thr
    210                 215                 220

Ser Glu Val Pro Gly Ser Gln Ala Ser Pro Asn Pro Val Pro Gly Asp
225                 230                 235                 240

Gly Leu His Arg Ala Gly Phe Asp
                245

<210> SEQ ID NO 88
<211> LENGTH: 253
<212> TYPE: PRT
<213> ORGANISM: Artificial Sequence
<220> FEATURE:
<223> OTHER INFORMATION: K111/D363 Deletion mutant of TOE1

<400> SEQUENCE: 88

Lys Gly Glu His Ser Tyr Leu Ala Gln Val Phe Asn Leu Thr Leu Leu
1               5                   10                  15

Cys Met Glu Glu Tyr Val Ile Glu Pro Lys Ser Val Gln Phe Leu Ile
            20                  25                  30

Gln His Gly Phe Asn Phe Asn Gln Gln Tyr Ala Gln Gly Ile Pro Tyr
        35                  40                  45

His Lys Gly Asn Asp Lys Gly Asp Glu Ser Gln Ser Gln Ser Val Arg
    50                  55                  60

Thr Leu Phe Leu Glu Leu Ile Arg Ala Arg Arg Pro Leu Val Leu His
65                  70                  75                  80
```

```
Asn Gly Leu Ile Asp Leu Val Phe Leu Tyr Gln Asn Phe Tyr Ala His
            85                  90                  95

Leu Pro Glu Ser Leu Gly Thr Phe Thr Ala Asp Leu Cys Glu Met Phe
        100                 105                 110

Pro Ala Gly Ile Tyr Asp Thr Lys Tyr Ala Ala Glu Phe His Ala Arg
        115                 120                 125

Phe Val Ala Ser Tyr Leu Glu Tyr Ala Phe Arg Lys Cys Glu Arg Glu
    130                 135                 140

Asn Gly Lys Gln Arg Ala Ala Gly Ser Pro His Leu Thr Leu Glu Phe
145                 150                 155                 160

Cys Asn Tyr Pro Ser Ser Met Arg Asp His Ile Asp Tyr Arg Cys Cys
            165                 170                 175

Leu Pro Pro Ala Thr His Arg Pro His Pro Thr Ser Ile Cys Asp Asn
        180                 185                 190

Phe Ser Ala Tyr Gly Trp Cys Pro Leu Gly Pro Gln Cys Pro Gln Ser
        195                 200                 205

His Asp Ile Asp Leu Ile Ile Asp Thr Asp Glu Ala Ala Ala Glu Asp
    210                 215                 220

Lys Arg Arg Arg Arg Arg Arg Glu Lys Arg Lys Arg Ala Leu Leu
225                 230                 235                 240

Asn Leu Pro Gly Thr Gln Thr Ser Gly Glu Ala Lys Asp
            245                 250
```

<210> SEQ ID NO 89
<211> LENGTH: 263
<212> TYPE: PRT
<213> ORGANISM: Artificial Sequence
<220> FEATURE:
<223> OTHER INFORMATION: K111/D373 Deletion mutant of TOE1

<400> SEQUENCE: 89

```
Lys Gly Glu His Ser Tyr Leu Ala Gln Val Phe Asn Leu Thr Leu Leu
1               5                   10                  15

Cys Met Glu Glu Tyr Val Ile Glu Pro Lys Ser Val Gln Phe Leu Ile
            20                  25                  30

Gln His Gly Phe Asn Phe Asn Gln Gln Tyr Ala Gln Gly Ile Pro Tyr
        35                  40                  45

His Lys Gly Asn Asp Lys Gly Asp Glu Ser Gln Ser Gln Ser Val Arg
    50                  55                  60

Thr Leu Phe Leu Glu Leu Ile Arg Ala Arg Arg Pro Leu Val Leu His
65                  70                  75                  80

Asn Gly Leu Ile Asp Leu Val Phe Leu Tyr Gln Asn Phe Tyr Ala His
            85                  90                  95

Leu Pro Glu Ser Leu Gly Thr Phe Thr Ala Asp Leu Cys Glu Met Phe
        100                 105                 110

Pro Ala Gly Ile Tyr Asp Thr Lys Tyr Ala Ala Glu Phe His Ala Arg
        115                 120                 125

Phe Val Ala Ser Tyr Leu Glu Tyr Ala Phe Arg Lys Cys Glu Arg Glu
    130                 135                 140

Asn Gly Lys Gln Arg Ala Ala Gly Ser Pro His Leu Thr Leu Glu Phe
145                 150                 155                 160

Cys Asn Tyr Pro Ser Ser Met Arg Asp His Ile Asp Tyr Arg Cys Cys
            165                 170                 175

Leu Pro Pro Ala Thr His Arg Pro His Pro Thr Ser Ile Cys Asp Asn
        180                 185                 190
```

Phe Ser Ala Tyr Gly Trp Cys Pro Leu Gly Pro Gln Cys Pro Gln Ser
            195                 200                 205

His Asp Ile Asp Leu Ile Ile Asp Thr Asp Glu Ala Ala Ala Glu Asp
        210                 215                 220

Lys Arg Arg Arg Arg Arg Arg Glu Lys Lys Arg Ala Leu Leu
225                 230                 235                 240

Asn Leu Pro Gly Thr Gln Thr Ser Gly Glu Ala Lys Asp Gly Pro Pro
                245                 250                 255

Lys Lys Gln Val Cys Gly Asp
            260

<210> SEQ ID NO 90
<211> LENGTH: 277
<212> TYPE: PRT
<213> ORGANISM: Artificial Sequence
<220> FEATURE:
<223> OTHER INFORMATION: K111/D387 Deletion mutant of TOE1

<400> SEQUENCE: 90

Lys Gly Glu His Ser Tyr Leu Ala Gln Val Phe Asn Leu Thr Leu Leu
1               5                   10                  15

Cys Met Glu Glu Tyr Val Ile Glu Pro Lys Ser Val Gln Phe Leu Ile
            20                  25                  30

Gln His Gly Phe Asn Phe Asn Gln Gln Tyr Ala Gln Gly Ile Pro Tyr
        35                  40                  45

His Lys Gly Asn Asp Lys Gly Asp Glu Ser Gln Ser Gln Ser Val Arg
    50                  55                  60

Thr Leu Phe Leu Glu Leu Ile Arg Ala Arg Arg Pro Leu Val Leu His
65                  70                  75                  80

Asn Gly Leu Ile Asp Leu Val Phe Leu Tyr Gln Asn Phe Tyr Ala His
                85                  90                  95

Leu Pro Glu Ser Leu Gly Thr Phe Thr Ala Asp Leu Cys Glu Met Phe
            100                 105                 110

Pro Ala Gly Ile Tyr Asp Thr Lys Tyr Ala Ala Glu Phe His Ala Arg
        115                 120                 125

Phe Val Ala Ser Tyr Leu Glu Tyr Ala Phe Arg Lys Cys Glu Arg Glu
    130                 135                 140

Asn Gly Lys Gln Arg Ala Ala Gly Ser Pro His Leu Thr Leu Glu Phe
145                 150                 155                 160

Cys Asn Tyr Pro Ser Ser Met Arg Asp His Ile Asp Tyr Arg Cys Cys
                165                 170                 175

Leu Pro Pro Ala Thr His Arg Pro His Pro Thr Ser Ile Cys Asp Asn
            180                 185                 190

Phe Ser Ala Tyr Gly Trp Cys Pro Leu Gly Pro Gln Cys Pro Gln Ser
        195                 200                 205

His Asp Ile Asp Leu Ile Ile Asp Thr Asp Glu Ala Ala Ala Glu Asp
    210                 215                 220

Lys Arg Arg Arg Arg Arg Arg Glu Lys Lys Arg Ala Leu Leu
225                 230                 235                 240

Asn Leu Pro Gly Thr Gln Thr Ser Gly Glu Ala Lys Asp Gly Pro Pro
                245                 250                 255

Lys Lys Gln Val Cys Gly Asp Ser Ile Lys Pro Glu Glu Thr Glu Gln
            260                 265                 270

Glu Val Ala Ala Asp
        275

<210> SEQ ID NO 91
<211> LENGTH: 292
<212> TYPE: PRT
<213> ORGANISM: Artificial Sequence
<220> FEATURE:
<223> OTHER INFORMATION: K111/D402 Deletion mutant of TOE1

<400> SEQUENCE: 91

Lys Gly Glu His Ser Tyr Leu Ala Gln Val Phe Asn Leu Thr Leu Leu
1               5                   10                  15

Cys Met Glu Glu Tyr Val Ile Glu Pro Lys Ser Val Gln Phe Leu Ile
            20                  25                  30

Gln His Gly Phe Asn Phe Asn Gln Tyr Ala Gln Gly Ile Pro Tyr
        35                  40                  45

His Lys Gly Asn Asp Lys Gly Asp Glu Ser Gln Ser Gln Ser Val Arg
    50                  55                  60

Thr Leu Phe Leu Glu Leu Ile Arg Ala Arg Arg Pro Leu Val Leu His
65                  70                  75                  80

Asn Gly Leu Ile Asp Leu Val Phe Leu Tyr Gln Asn Phe Tyr Ala His
                85                  90                  95

Leu Pro Glu Ser Leu Gly Thr Phe Thr Ala Asp Leu Cys Glu Met Phe
            100                 105                 110

Pro Ala Gly Ile Tyr Asp Thr Lys Tyr Ala Ala Glu Phe His Ala Arg
        115                 120                 125

Phe Val Ala Ser Tyr Leu Glu Tyr Ala Phe Arg Lys Cys Glu Arg Glu
    130                 135                 140

Asn Gly Lys Gln Arg Ala Ala Gly Ser Pro His Leu Thr Leu Glu Phe
145                 150                 155                 160

Cys Asn Tyr Pro Ser Ser Met Arg Asp His Ile Asp Tyr Arg Cys Cys
                165                 170                 175

Leu Pro Pro Ala Thr His Arg Pro His Pro Thr Ser Ile Cys Asp Asn
            180                 185                 190

Phe Ser Ala Tyr Gly Trp Cys Pro Leu Gly Pro Gln Cys Pro Gln Ser
        195                 200                 205

His Asp Ile Asp Leu Ile Ile Asp Thr Asp Glu Ala Ala Ala Glu Asp
    210                 215                 220

Lys Arg Arg Arg Arg Arg Arg Glu Lys Arg Lys Arg Ala Leu Leu
225                 230                 235                 240

Asn Leu Pro Gly Thr Gln Thr Ser Gly Glu Ala Lys Asp Gly Pro Pro
                245                 250                 255

Lys Lys Gln Val Cys Gly Asp Ser Ile Lys Pro Glu Gly Thr Glu Gln
            260                 265                 270

Glu Val Ala Ala Asp Glu Thr Arg Asn Leu Pro His Ser Lys Gln Gly
        275                 280                 285

Asn Lys Asn Asp
    290

<210> SEQ ID NO 92
<211> LENGTH: 306
<212> TYPE: PRT
<213> ORGANISM: Artificial Sequence
<220> FEATURE:
<223> OTHER INFORMATION: K111/D416 Deletion mutant of TOE1

<400> SEQUENCE: 92

Lys Gly Glu His Ser Tyr Leu Ala Gln Val Phe Asn Leu Thr Leu Leu
1               5                   10                  15

Cys Met Glu Glu Tyr Val Ile Glu Pro Lys Ser Val Gln Phe Leu Ile
            20                  25                  30

Gln His Gly Phe Asn Phe Asn Gln Gln Tyr Ala Gln Gly Ile Pro Tyr
            35                  40                  45

His Lys Gly Asn Asp Lys Gly Asp Glu Ser Gln Ser Gln Ser Val Arg
 50                  55                  60

Thr Leu Phe Leu Glu Leu Ile Arg Ala Arg Pro Leu Val Leu His
 65                  70                  75                  80

Asn Gly Leu Ile Asp Leu Val Phe Leu Tyr Gln Asn Phe Tyr Ala His
                85                  90                  95

Leu Pro Glu Ser Leu Gly Thr Phe Thr Ala Asp Leu Cys Glu Met Phe
            100                 105                 110

Pro Ala Gly Ile Tyr Asp Thr Lys Tyr Ala Ala Glu Phe His Ala Arg
            115                 120                 125

Phe Val Ala Ser Tyr Leu Glu Tyr Ala Phe Arg Lys Cys Glu Arg Glu
130                 135                 140

Asn Gly Lys Gln Arg Ala Ala Gly Ser Pro His Leu Thr Leu Glu Phe
145                 150                 155                 160

Cys Asn Tyr Pro Ser Ser Met Arg Asp His Ile Asp Tyr Arg Cys Cys
            165                 170                 175

Leu Pro Pro Ala Thr His Arg Pro His Pro Thr Ser Ile Cys Asp Asn
            180                 185                 190

Phe Ser Ala Tyr Gly Trp Cys Pro Leu Gly Pro Gln Cys Pro Gln Ser
            195                 200                 205

His Asp Ile Asp Leu Ile Ile Asp Thr Asp Glu Ala Ala Ala Glu Asp
            210                 215                 220

Lys Arg Arg Arg Arg Arg Arg Glu Lys Arg Lys Arg Ala Leu Leu
225                 230                 235                 240

Asn Leu Pro Gly Thr Gln Thr Ser Gly Glu Ala Lys Asp Gly Pro Pro
            245                 250                 255

Lys Lys Gln Val Cys Gly Asp Ser Ile Lys Pro Glu Glu Thr Glu Gln
            260                 265                 270

Glu Val Ala Ala Asp Glu Thr Arg Asn Leu Pro His Ser Lys Gln Gly
            275                 280                 285

Asn Lys Asn Asp Leu Glu Met Gly Ile Lys Ala Ala Arg Pro Glu Ile
290                 295                 300

Ala Asp
305

<210> SEQ ID NO 93
<211> LENGTH: 325
<212> TYPE: PRT
<213> ORGANISM: Artificial Sequence
<220> FEATURE:
<223> OTHER INFORMATION: K111/D435 Deletion mutant of TOE1

<400> SEQUENCE: 93

Lys Gly Glu His Ser Tyr Leu Ala Gln Val Phe Asn Leu Thr Leu Leu
1               5                   10                  15

Cys Met Glu Glu Tyr Val Ile Glu Pro Lys Ser Val Gln Phe Leu Ile
            20                  25                  30

Gln His Gly Phe Asn Phe Asn Gln Gln Tyr Ala Gln Gly Ile Pro Tyr
            35                  40                  45

His Lys Gly Asn Asp Lys Gly Asp Glu Ser Gln Ser Gln Ser Val Arg
 50                  55                  60

```
Thr Leu Phe Leu Glu Leu Ile Arg Ala Arg Arg Pro Leu Val Leu His
 65                  70                  75                  80

Asn Gly Leu Ile Asp Leu Val Phe Leu Tyr Gln Asn Phe Tyr Ala His
                 85                  90                  95

Leu Pro Glu Ser Leu Gly Thr Thr Ala Asp Leu Cys Glu Met Phe
            100                 105                 110

Pro Ala Gly Ile Tyr Asp Thr Lys Tyr Ala Ala Glu Phe His Ala Arg
            115                 120                 125

Phe Val Ala Ser Tyr Leu Glu Tyr Ala Phe Arg Lys Cys Glu Arg Glu
130                 135                 140

Asn Gly Lys Gln Arg Ala Ala Gly Ser Pro His Leu Thr Leu Glu Phe
145                 150                 155                 160

Cys Asn Tyr Pro Ser Ser Met Arg Asp His Ile Asp Tyr Arg Cys Cys
                165                 170                 175

Leu Pro Pro Ala Thr His Arg Pro His Pro Thr Ser Ile Cys Asp Asn
            180                 185                 190

Phe Ser Ala Tyr Gly Trp Cys Pro Leu Gly Pro Gln Cys Pro Gln Ser
            195                 200                 205

His Asp Ile Asp Leu Ile Ile Asp Thr Asp Glu Ala Ala Ala Glu Asp
            210                 215                 220

Lys Arg Arg Arg Arg Arg Arg Glu Lys Arg Lys Arg Ala Leu Leu
225                 230                 235                 240

Asn Leu Pro Gly Thr Gln Thr Ser Gly Glu Ala Lys Asp Gly Pro Pro
                245                 250                 255

Lys Lys Gln Val Cys Gly Asp Ser Ile Lys Pro Glu Glu Thr Glu Gln
                260                 265                 270

Glu Val Ala Ala Asp Glu Thr Arg Asn Leu Pro His Ser Lys Gln Gly
            275                 280                 285

Asn Lys Asn Asp Leu Glu Met Gly Ile Lys Ala Arg Pro Glu Ile
290                 295                 300

Ala Asp Arg Ala Thr Ser Glu Val Pro Gly Ser Gln Ala Ser Pro Asn
305                 310                 315                 320

Pro Val Pro Gly Asp
            325

<210> SEQ ID NO 94
<211> LENGTH: 333
<212> TYPE: PRT
<213> ORGANISM: Artificial Sequence
<220> FEATURE:
<223> OTHER INFORMATION: K111/D443 Deletion mutant of TOE1

<400> SEQUENCE: 94

Lys Gly Glu His Ser Tyr Leu Ala Gln Val Phe Asn Leu Thr Leu Leu
  1               5                  10                  15

Cys Met Glu Glu Tyr Val Ile Glu Pro Lys Ser Val Gln Phe Leu Ile
             20                  25                  30

Gln His Gly Phe Asn Phe Asn Gln Gln Tyr Ala Gln Gly Ile Pro Tyr
         35                  40                  45

His Lys Gly Asn Asp Lys Gly Asp Glu Ser Gln Ser Gln Ser Val Arg
     50                  55                  60

Thr Leu Phe Leu Glu Leu Ile Arg Ala Arg Arg Pro Leu Val Leu His
 65                  70                  75                  80

Asn Gly Leu Ile Asp Leu Val Phe Leu Tyr Gln Asn Phe Tyr Ala His
                 85                  90                  95
```

```
Leu Pro Glu Ser Leu Gly Thr Phe Thr Ala Asp Leu Cys Glu Met Phe
            100                 105                 110

Pro Ala Gly Ile Tyr Asp Thr Lys Tyr Ala Ala Glu Phe His Ala Arg
        115                 120                 125

Phe Val Ala Ser Tyr Leu Glu Tyr Ala Phe Arg Lys Cys Glu Arg Glu
    130                 135                 140

Asn Gly Lys Gln Arg Ala Ala Gly Ser Pro His Leu Thr Leu Glu Phe
145                 150                 155                 160

Cys Asn Tyr Pro Ser Ser Met Arg Asp His Ile Asp Tyr Arg Cys Cys
                165                 170                 175

Leu Pro Pro Ala Thr His Arg Pro His Pro Thr Ser Ile Cys Asp Asn
            180                 185                 190

Phe Ser Ala Tyr Gly Trp Cys Pro Leu Gly Pro Gln Cys Pro Gln Ser
        195                 200                 205

His Asp Ile Asp Leu Ile Ile Asp Thr Asp Glu Ala Ala Ala Glu Asp
    210                 215                 220

Lys Arg Arg Arg Arg Arg Arg Glu Lys Arg Lys Arg Ala Leu Leu
225                 230                 235                 240

Asn Leu Pro Gly Thr Gln Thr Ser Gly Glu Ala Lys Asp Gly Pro Pro
                245                 250                 255

Lys Lys Gln Val Cys Gly Asp Ser Ile Lys Pro Glu Glu Thr Glu Gln
            260                 265                 270

Glu Val Ala Ala Asp Glu Thr Arg Asn Leu Pro His Ser Lys Gln Gly
        275                 280                 285

Asn Lys Asn Asp Leu Glu Met Gly Ile Lys Ala Ala Arg Pro Glu Ile
    290                 295                 300

Ala Asp Arg Ala Thr Ser Glu Val Pro Gly Ser Gln Ala Ser Pro Asn
305                 310                 315                 320

Pro Val Pro Gly Asp Gly Leu His Arg Ala Gly Phe Asp
                325                 330

<210> SEQ ID NO 95
<211> LENGTH: 400
<212> TYPE: PRT
<213> ORGANISM: Artificial Sequence
<220> FEATURE:
<223> OTHER INFORMATION: K111/S510 Deletion mutant of TOE1

<400> SEQUENCE: 95

Lys Gly Glu His Ser Tyr Leu Ala Gln Val Phe Asn Leu Thr Leu Leu
1               5                   10                  15

Cys Met Glu Glu Tyr Val Ile Glu Pro Lys Ser Val Gln Phe Leu Ile
            20                  25                  30

Gln His Gly Phe Asn Phe Asn Gln Tyr Ala Gln Gly Ile Pro Tyr
        35                  40                  45

His Lys Gly Asn Asp Lys Gly Asp Glu Ser Gln Ser Gln Ser Val Arg
    50                  55                  60

Thr Leu Phe Leu Glu Leu Ile Arg Ala Arg Arg Pro Leu Val Leu His
65                  70                  75                  80

Asn Gly Leu Ile Asp Leu Val Phe Leu Tyr Gln Asn Tyr Ala His
                85                  90                  95

Leu Pro Glu Ser Leu Gly Thr Phe Thr Ala Asp Leu Cys Glu Met Phe
            100                 105                 110

Pro Ala Gly Ile Tyr Asp Thr Lys Tyr Ala Ala Glu Phe His Ala Arg
        115                 120                 125
```

-continued

```
Phe Val Ala Ser Tyr Leu Glu Tyr Ala Phe Arg Lys Cys Glu Arg Glu
    130                 135                 140

Asn Gly Lys Gln Arg Ala Ala Gly Ser Pro His Leu Thr Leu Glu Phe
145                 150                 155                 160

Cys Asn Tyr Pro Ser Ser Met Arg Asp His Ile Asp Tyr Arg Cys Cys
                165                 170                 175

Leu Pro Pro Ala Thr His Arg Pro His Pro Thr Ser Ile Cys Asp Asn
            180                 185                 190

Phe Ser Ala Tyr Gly Trp Cys Pro Leu Gly Pro Gln Cys Pro Gln Ser
        195                 200                 205

His Asp Ile Asp Leu Ile Ile Asp Thr Asp Glu Ala Ala Ala Glu Asp
    210                 215                 220

Lys Arg Arg Arg Arg Arg Arg Glu Lys Arg Lys Arg Ala Leu Leu
225                 230                 235                 240

Asn Leu Pro Gly Thr Gln Thr Ser Gly Glu Ala Lys Asp Gly Pro Pro
                245                 250                 255

Lys Lys Gln Val Cys Gly Asp Ser Ile Lys Pro Glu Glu Thr Glu Gln
            260                 265                 270

Glu Val Ala Ala Asp Glu Thr Arg Asn Leu Pro His Ser Lys Gln Gly
        275                 280                 285

Asn Lys Asn Asp Leu Glu Met Gly Ile Lys Ala Ala Arg Pro Glu Ile
    290                 295                 300

Ala Asp Arg Ala Thr Ser Glu Val Pro Gly Ser Gln Ala Ser Pro Asn
305                 310                 315                 320

Pro Val Pro Gly Asp Gly Leu His Arg Ala Gly Phe Asp Ala Phe Met
                325                 330                 335

Thr Gly Tyr Val Met Ala Tyr Val Glu Val Ser Gln Gly Pro Gln Pro
            340                 345                 350

Cys Ser Ser Gly Pro Trp Leu Pro Glu Cys His Asn Lys Val Tyr Leu
        355                 360                 365

Ser Gly Lys Ala Val Pro Leu Thr Val Ala Lys Ser Gln Phe Ser Arg
    370                 375                 380

Ser Ser Lys Ala His Asn Gln Lys Met Lys Leu Thr Trp Gly Ser Ser
385                 390                 395                 400
```

<210> SEQ ID NO 96
<211> LENGTH: 299
<212> TYPE: PRT
<213> ORGANISM: Artificial Sequence
<220> FEATURE:
<223> OTHER INFORMATION: T65/D363 Deletion mutant of TOE1

<400> SEQUENCE: 96

```
Thr Glu Leu Ser Gly Leu Gly Asp Arg Lys Ser Leu Asn Gln Cys
1               5                   10                  15

Ile Glu Glu Arg Tyr Lys Ala Val Cys His Ala Ala Arg Thr Arg Ser
                20                  25                  30

Ile Leu Ser Leu Gly Leu Ala Cys Phe Lys Arg Gln Pro Asp Lys Gly
            35                  40                  45

Glu His Ser Tyr Leu Ala Gln Val Phe Asn Leu Thr Leu Leu Cys Met
        50                  55                  60

Glu Glu Tyr Val Ile Glu Pro Lys Ser Val Gln Phe Leu Ile Gln His
65                  70                  75                  80

Gly Phe Asn Phe Asn Gln Gln Tyr Ala Gln Gly Ile Pro Tyr His Lys
                85                  90                  95
```

```
Gly Asn Asp Lys Gly Asp Glu Ser Gln Ser Gln Ser Val Arg Thr Leu
                100                 105                 110

Phe Leu Glu Leu Ile Arg Ala Arg Arg Pro Leu Val Leu His Asn Gly
            115                 120                 125

Leu Ile Asp Leu Val Phe Leu Tyr Gln Asn Phe Tyr Ala His Leu Pro
        130                 135                 140

Glu Ser Leu Gly Thr Phe Thr Ala Asp Leu Cys Glu Met Phe Pro Ala
145                 150                 155                 160

Gly Ile Tyr Asp Thr Lys Tyr Ala Ala Glu Phe His Ala Arg Phe Val
                165                 170                 175

Ala Ser Tyr Leu Glu Tyr Ala Phe Arg Lys Cys Glu Arg Glu Asn Gly
            180                 185                 190

Lys Gln Arg Ala Ala Gly Ser Pro His Leu Thr Leu Glu Phe Cys Asn
        195                 200                 205

Tyr Pro Ser Ser Met Arg Asp His Ile Asp Tyr Arg Cys Cys Leu Pro
    210                 215                 220

Pro Ala Thr His Arg Pro His Pro Thr Ser Ile Cys Asp Asn Phe Ser
225                 230                 235                 240

Ala Tyr Gly Trp Cys Pro Leu Gly Pro Gln Cys Pro Gln Ser His Asp
                245                 250                 255

Ile Asp Leu Ile Ile Asp Thr Asp Glu Ala Ala Glu Asp Lys Arg
            260                 265                 270

Arg Arg Arg Arg Arg Glu Lys Arg Lys Arg Ala Leu Leu Asn Leu
        275                 280                 285

Pro Gly Thr Gln Thr Ser Gly Glu Ala Lys Asp
    290                 295
```

<210> SEQ ID NO 97
<211> LENGTH: 309
<212> TYPE: PRT
<213> ORGANISM: Artificial Sequence
<220> FEATURE:
<223> OTHER INFORMATION: T65/D373 Deletion mutant of TOE1

<400> SEQUENCE: 97

```
Thr Glu Leu Ser Gly Leu Gly Asp Arg Lys Ser Leu Leu Asn Gln Cys
1               5                   10                  15

Ile Glu Glu Arg Tyr Lys Ala Val Cys His Ala Ala Arg Thr Arg Ser
            20                  25                  30

Ile Leu Ser Leu Gly Leu Ala Cys Phe Lys Arg Gln Pro Asp Lys Gly
        35                  40                  45

Glu His Ser Tyr Leu Ala Gln Val Phe Asn Leu Thr Leu Leu Cys Met
    50                  55                  60

Glu Glu Tyr Val Ile Glu Pro Lys Ser Val Gln Phe Leu Ile Gln His
65                  70                  75                  80

Gly Phe Asn Phe Asn Gln Gln Tyr Ala Gln Gly Ile Pro Tyr His Lys
                85                  90                  95

Gly Asn Asp Lys Gly Asp Glu Ser Gln Ser Gln Ser Val Arg Thr Leu
            100                 105                 110

Phe Leu Glu Leu Ile Arg Ala Arg Arg Pro Leu Val Leu His Asn Gly
        115                 120                 125

Leu Ile Asp Leu Val Phe Leu Tyr Gln Asn Phe Tyr Ala His Leu Pro
    130                 135                 140

Glu Ser Leu Gly Thr Phe Thr Ala Asp Leu Cys Glu Met Phe Pro Ala
145                 150                 155                 160
```

```
Gly Ile Tyr Asp Thr Lys Tyr Ala Ala Glu Phe His Ala Arg Phe Val
            165                 170                 175

Ala Ser Tyr Leu Glu Tyr Ala Phe Arg Lys Cys Glu Arg Glu Asn Gly
            180                 185                 190

Lys Gln Arg Ala Ala Gly Ser Pro His Leu Thr Leu Glu Phe Cys Asn
            195                 200                 205

Tyr Pro Ser Ser Met Arg Asp His Ile Asp Tyr Arg Cys Cys Leu Pro
            210                 215                 220

Pro Ala Thr His Arg Pro His Pro Thr Ser Ile Cys Asp Asn Phe Ser
225                 230                 235                 240

Ala Tyr Gly Trp Cys Pro Leu Gly Pro Gln Cys Pro Gln Ser His Asp
            245                 250                 255

Ile Asp Leu Ile Ile Asp Thr Asp Glu Ala Ala Glu Asp Lys Arg
            260                 265                 270

Arg Arg Arg Arg Arg Glu Lys Arg Lys Arg Ala Leu Leu Asn Leu
275                 280                 285

Pro Gly Thr Gln Thr Ser Gly Glu Ala Lys Asp Gly Pro Pro Lys Lys
            290                 295                 300

Gln Val Cys Gly Asp
305

<210> SEQ ID NO 98
<211> LENGTH: 323
<212> TYPE: PRT
<213> ORGANISM: Artificial Sequence
<220> FEATURE:
<223> OTHER INFORMATION: T65/D387 Deletion mutant of TOE1

<400> SEQUENCE: 98

Thr Glu Leu Ser Gly Leu Gly Asp Arg Lys Ser Leu Leu Asn Gln Cys
1               5                   10                  15

Ile Glu Glu Arg Tyr Lys Ala Val Cys His Ala Ala Arg Thr Arg Ser
            20                  25                  30

Ile Leu Ser Leu Gly Leu Ala Cys Phe Lys Arg Gln Pro Asp Lys Gly
            35                  40                  45

Glu His Ser Tyr Leu Ala Gln Val Phe Asn Leu Thr Leu Leu Cys Met
            50                  55                  60

Glu Glu Tyr Val Ile Glu Pro Lys Ser Val Gln Phe Leu Ile Gln His
65                  70                  75                  80

Gly Phe Asn Phe Asn Gln Gln Tyr Ala Gln Gly Ile Pro Tyr His Lys
            85                  90                  95

Gly Asn Asp Lys Gly Asp Glu Ser Gln Ser Gln Ser Val Arg Thr Leu
            100                 105                 110

Phe Leu Glu Leu Ile Arg Ala Arg Arg Pro Leu Val Leu His Asn Gly
            115                 120                 125

Leu Ile Asp Leu Val Phe Leu Tyr Gln Asn Phe Tyr Ala His Leu Pro
            130                 135                 140

Glu Ser Leu Gly Thr Phe Thr Ala Asp Leu Cys Glu Met Phe Pro Ala
145                 150                 155                 160

Gly Ile Tyr Asp Thr Lys Tyr Ala Ala Glu Phe His Ala Arg Phe Val
            165                 170                 175

Ala Ser Tyr Leu Glu Tyr Ala Phe Arg Lys Cys Glu Arg Glu Asn Gly
            180                 185                 190

Lys Gln Arg Ala Ala Gly Ser Pro His Leu Thr Leu Glu Phe Cys Asn
            195                 200                 205
```

```
Tyr Pro Ser Ser Met Arg Asp His Ile Asp Tyr Arg Cys Cys Leu Pro
    210                 215                 220

Pro Ala Thr His Arg Pro His Pro Thr Ser Ile Cys Asp Asn Phe Ser
225                 230                 235                 240

Ala Tyr Gly Trp Cys Pro Leu Gly Pro Gln Cys Pro Gln Ser His Asp
                245                 250                 255

Ile Asp Leu Ile Ile Asp Thr Asp Glu Ala Ala Glu Asp Lys Arg
                260                 265                 270

Arg Arg Arg Arg Arg Glu Lys Arg Lys Arg Ala Leu Leu Asn Leu
            275                 280                 285

Pro Gly Thr Gln Thr Ser Gly Glu Ala Lys Asp Gly Pro Pro Lys Lys
    290                 295                 300

Gln Val Cys Gly Asp Ser Ile Lys Pro Glu Glu Thr Glu Gln Glu Val
305                 310                 315                 320

Ala Ala Asp
```

<210> SEQ ID NO 99
<211> LENGTH: 338
<212> TYPE: PRT
<213> ORGANISM: Artificial Sequence
<220> FEATURE:
<223> OTHER INFORMATION: T65/D402 Deletion mutant of TOE1

<400> SEQUENCE: 99

```
Thr Glu Leu Ser Gly Leu Gly Asp Arg Lys Ser Leu Leu Asn Gln Cys
1               5                   10                  15

Ile Glu Glu Arg Tyr Lys Ala Val Cys His Ala Ala Arg Thr Arg Ser
                20                  25                  30

Ile Leu Ser Leu Gly Leu Ala Cys Phe Lys Arg Gln Pro Asp Lys Gly
            35                  40                  45

Glu His Ser Tyr Leu Ala Gln Val Phe Asn Leu Thr Leu Leu Cys Met
        50                  55                  60

Glu Glu Tyr Val Ile Glu Pro Lys Ser Val Gln Phe Leu Ile Gln His
65                  70                  75                  80

Gly Phe Asn Phe Asn Gln Gln Tyr Ala Gln Gly Ile Pro Tyr His Lys
                85                  90                  95

Gly Asn Asp Lys Gly Asp Glu Ser Gln Ser Gln Ser Val Arg Thr Leu
                100                 105                 110

Phe Leu Glu Leu Ile Arg Ala Arg Arg Pro Leu Val Leu His Asn Gly
            115                 120                 125

Leu Ile Asp Leu Val Phe Leu Tyr Gln Asn Phe Tyr Ala His Leu Pro
        130                 135                 140

Glu Ser Leu Gly Thr Phe Thr Ala Asp Leu Cys Glu Met Phe Pro Ala
145                 150                 155                 160

Gly Ile Tyr Asp Thr Lys Tyr Ala Ala Glu Phe His Ala Arg Phe Val
                165                 170                 175

Ala Ser Tyr Leu Glu Tyr Ala Phe Arg Lys Cys Glu Arg Glu Asn Gly
            180                 185                 190

Lys Gln Arg Ala Ala Gly Ser Pro His Leu Thr Leu Glu Phe Cys Asn
        195                 200                 205

Tyr Pro Ser Ser Met Arg Asp His Ile Asp Tyr Arg Cys Cys Leu Pro
    210                 215                 220

Pro Ala Thr His Arg Pro His Pro Thr Ser Ile Cys Asp Asn Phe Ser
225                 230                 235                 240
```

```
Ala Tyr Gly Trp Cys Pro Leu Gly Pro Gln Cys Pro Gln Ser His Asp
                245                 250                 255

Ile Asp Leu Ile Ile Asp Thr Asp Glu Ala Ala Ala Glu Asp Lys Arg
            260                 265                 270

Arg Arg Arg Arg Arg Glu Lys Arg Lys Arg Ala Leu Leu Asn Leu
        275                 280                 285

Pro Gly Thr Gln Thr Ser Gly Glu Ala Lys Asp Gly Pro Pro Lys Lys
        290                 295                 300

Gln Val Cys Gly Asp Ser Ile Lys Pro Glu Thr Glu Gln Glu Val
305                 310                 315                 320

Ala Ala Asp Glu Thr Arg Asn Leu Pro His Ser Lys Gln Gly Asn Lys
                325                 330                 335

Asn Asp

<210> SEQ ID NO 100
<211> LENGTH: 352
<212> TYPE: PRT
<213> ORGANISM: Artificial Sequence
<220> FEATURE:
<223> OTHER INFORMATION: T65/D416 Deletion mutant of TOE1

<400> SEQUENCE: 100

Thr Glu Leu Ser Gly Leu Gly Asp Arg Lys Ser Leu Leu Asn Gln Cys
1               5                   10                  15

Ile Glu Glu Arg Tyr Lys Ala Val Cys His Ala Ala Arg Thr Arg Ser
                20                  25                  30

Ile Leu Ser Leu Gly Leu Ala Cys Phe Lys Arg Gln Pro Asp Lys Gly
            35                  40                  45

Glu His Ser Tyr Leu Ala Gln Val Phe Asn Leu Thr Leu Leu Cys Met
        50                  55                  60

Glu Glu Tyr Val Ile Glu Pro Lys Ser Val Gln Phe Leu Ile Gln His
65                  70                  75                  80

Gly Phe Asn Phe Asn Gln Gln Tyr Ala Gln Gly Ile Pro Tyr His Lys
                85                  90                  95

Gly Asn Asp Lys Gly Asp Glu Ser Gln Ser Gln Ser Val Arg Thr Leu
            100                 105                 110

Phe Leu Glu Leu Ile Arg Ala Arg Arg Pro Leu Val Leu His Asn Gly
        115                 120                 125

Leu Ile Asp Leu Val Phe Leu Tyr Gln Asn Phe Tyr Ala His Leu Pro
    130                 135                 140

Glu Ser Leu Gly Thr Phe Thr Ala Asp Leu Cys Glu Met Phe Pro Ala
145                 150                 155                 160

Gly Ile Tyr Asp Thr Lys Tyr Ala Ala Glu Phe His Ala Arg Phe Val
                165                 170                 175

Ala Ser Tyr Leu Glu Tyr Ala Phe Arg Lys Cys Glu Arg Glu Asn Gly
            180                 185                 190

Lys Gln Arg Ala Ala Gly Ser Pro His Leu Thr Leu Glu Phe Cys Asn
        195                 200                 205

Tyr Pro Ser Ser Met Arg Asp His Ile Asp Tyr Arg Cys Cys Leu Pro
    210                 215                 220

Pro Ala Thr His Arg Pro His Pro Thr Ser Ile Cys Asp Asn Phe Ser
225                 230                 235                 240

Ala Tyr Gly Trp Cys Pro Leu Gly Pro Gln Cys Pro Gln Ser His Asp
                245                 250                 255

Ile Asp Leu Ile Ile Asp Thr Asp Glu Ala Ala Ala Glu Asp Lys Arg
```

```
                260                 265                 270
Arg Arg Arg Arg Arg Arg Glu Lys Arg Lys Arg Ala Leu Leu Asn Leu
            275                 280                 285

Pro Gly Thr Gln Thr Ser Gly Glu Ala Lys Asp Gly Pro Lys Lys
            290                 295                 300

Gln Val Cys Gly Asp Ser Ile Lys Pro Glu Glu Thr Glu Gln Glu Val
305                 310                 315                 320

Ala Ala Asp Glu Thr Arg Asn Leu Pro His Ser Lys Gln Gly Asn Lys
            325                 330                 335

Asn Asp Leu Glu Met Gly Ile Lys Ala Ala Arg Pro Glu Ile Ala Asp
            340                 345                 350

<210> SEQ ID NO 101
<211> LENGTH: 371
<212> TYPE: PRT
<213> ORGANISM: Artificial Sequence
<220> FEATURE:
<223> OTHER INFORMATION: T65/D435 Deletion mutant of TOE1

<400> SEQUENCE: 101

Thr Glu Leu Ser Gly Leu Gly Asp Arg Lys Ser Leu Leu Asn Gln Cys
1               5                   10                  15

Ile Glu Glu Arg Tyr Lys Ala Val Cys His Ala Ala Arg Thr Arg Ser
            20                  25                  30

Ile Leu Ser Leu Gly Leu Ala Cys Phe Lys Arg Gln Pro Asp Lys Gly
        35                  40                  45

Glu His Ser Tyr Leu Ala Gln Val Phe Asn Leu Thr Leu Leu Cys Met
    50                  55                  60

Glu Glu Tyr Val Ile Glu Pro Lys Ser Val Gln Phe Leu Ile Gln His
65                  70                  75                  80

Gly Phe Asn Phe Asn Gln Gln Tyr Ala Gln Gly Ile Pro Tyr His Lys
                85                  90                  95

Gly Asn Asp Lys Gly Asp Glu Ser Gln Ser Gln Ser Val Arg Thr Leu
            100                 105                 110

Phe Leu Glu Leu Ile Arg Ala Arg Arg Pro Leu Val Leu His Asn Gly
        115                 120                 125

Leu Ile Asp Leu Val Phe Leu Tyr Gln Asn Phe Tyr Ala His Leu Pro
    130                 135                 140

Glu Ser Leu Gly Thr Phe Thr Ala Asp Leu Cys Glu Met Phe Pro Ala
145                 150                 155                 160

Gly Ile Tyr Asp Thr Lys Tyr Ala Ala Glu Phe His Ala Arg Phe Val
                165                 170                 175

Ala Ser Tyr Leu Glu Tyr Ala Phe Arg Lys Cys Glu Arg Glu Asn Gly
            180                 185                 190

Lys Gln Arg Ala Ala Gly Ser Pro His Leu Thr Leu Glu Phe Cys Asn
        195                 200                 205

Tyr Pro Ser Ser Met Arg Asp His Ile Asp Tyr Arg Cys Cys Leu Pro
    210                 215                 220

Pro Ala Thr His Arg Pro His Pro Thr Ser Ile Cys Asp Asn Phe Ser
225                 230                 235                 240

Ala Tyr Gly Trp Cys Pro Leu Gly Pro Gln Cys Pro Gln Ser His Asp
                245                 250                 255

Ile Asp Leu Ile Ile Asp Thr Asp Glu Ala Ala Ala Glu Asp Lys Arg
            260                 265                 270

Arg Arg Arg Arg Arg Arg Glu Lys Arg Lys Arg Ala Leu Leu Asn Leu
```

```
                        275                 280                 285
Pro Gly Thr Gln Thr Ser Gly Glu Ala Lys Asp Gly Pro Lys Lys
    290                 295                 300
Gln Val Cys Gly Asp Ser Ile Lys Pro Glu Glu Thr Glu Gln Glu Val
305                 310                 315                 320
Ala Ala Asp Glu Thr Arg Asn Leu Pro His Ser Lys Gln Gly Asn Lys
                325                 330                 335
Asn Asp Leu Glu Met Gly Ile Lys Ala Ala Arg Pro Glu Ile Ala Asp
                340                 345                 350
Arg Ala Thr Ser Glu Val Pro Gly Ser Gln Ala Ser Pro Asn Pro Val
                355                 360                 365
Pro Gly Asp
    370

<210> SEQ ID NO 102
<211> LENGTH: 379
<212> TYPE: PRT
<213> ORGANISM: Artificial Sequence
<220> FEATURE:
<223> OTHER INFORMATION: T65/D443 Deletion mutant of TOE1

<400> SEQUENCE: 102

Thr Glu Leu Ser Gly Leu Gly Asp Arg Lys Ser Leu Leu Asn Gln Cys
1               5                   10                  15

Ile Glu Glu Arg Tyr Lys Ala Val Cys His Ala Ala Arg Thr Arg Ser
                20                  25                  30

Ile Leu Ser Leu Gly Leu Ala Cys Phe Lys Arg Gln Pro Asp Lys Gly
            35                  40                  45

Glu His Ser Tyr Leu Ala Gln Val Phe Asn Leu Thr Leu Leu Cys Met
        50                  55                  60

Glu Glu Tyr Val Ile Glu Pro Lys Ser Val Gln Phe Leu Ile Gln His
65                  70                  75                  80

Gly Phe Asn Phe Asn Gln Gln Tyr Ala Gln Gly Ile Pro Tyr His Lys
                85                  90                  95

Gly Asn Asp Lys Gly Asp Glu Ser Gln Ser Gln Ser Val Arg Thr Leu
            100                 105                 110

Phe Leu Glu Leu Ile Arg Ala Arg Arg Pro Leu Val Leu His Asn Gly
        115                 120                 125

Leu Ile Asp Leu Val Phe Leu Tyr Gln Asn Phe Tyr Ala His Leu Pro
    130                 135                 140

Glu Ser Leu Gly Thr Phe Thr Ala Asp Leu Cys Glu Met Phe Pro Ala
145                 150                 155                 160

Gly Ile Tyr Asp Thr Lys Tyr Ala Ala Glu Phe His Ala Arg Phe Val
                165                 170                 175

Ala Ser Tyr Leu Glu Tyr Ala Phe Arg Lys Cys Glu Arg Glu Asn Gly
            180                 185                 190

Lys Gln Arg Ala Ala Gly Ser Pro His Leu Thr Leu Glu Phe Cys Asn
        195                 200                 205

Tyr Pro Ser Ser Met Arg Asp His Ile Asp Tyr Arg Cys Cys Leu Pro
    210                 215                 220

Pro Ala Thr His Arg Pro His Pro Thr Ser Ile Cys Asp Asn Phe Ser
225                 230                 235                 240

Ala Tyr Gly Trp Cys Pro Leu Gly Pro Gln Cys Pro Gln Ser His Asp
                245                 250                 255

Ile Asp Leu Ile Ile Asp Thr Asp Glu Ala Ala Ala Glu Asp Lys Arg
```

```
                260                 265                 270
Arg Arg Arg Arg Arg Glu Lys Arg Lys Ala Leu Leu Asn Leu
            275                 280                 285

Pro Gly Thr Gln Thr Ser Gly Glu Ala Lys Asp Gly Pro Lys Lys
        290                 295                 300

Gln Val Cys Gly Asp Ser Ile Lys Pro Glu Glu Thr Glu Gln Glu Val
305                 310                 315                 320

Ala Ala Asp Glu Thr Arg Asn Leu Pro His Ser Lys Gln Gly Asn Lys
                325                 330                 335

Asn Asp Leu Glu Met Gly Ile Lys Ala Ala Arg Pro Glu Ile Ala Asp
                340                 345                 350

Arg Ala Thr Ser Glu Val Pro Gly Ser Gln Ala Ser Pro Asn Pro Val
            355                 360                 365

Pro Gly Asp Gly Leu His Arg Ala Gly Phe Asp
            370                 375

<210> SEQ ID NO 103
<211> LENGTH: 446
<212> TYPE: PRT
<213> ORGANISM: Artificial Sequence
<220> FEATURE:
<223> OTHER INFORMATION: T65/S510 Deletion mutant of TOE1

<400> SEQUENCE: 103

Thr Glu Leu Ser Gly Leu Gly Asp Arg Lys Ser Leu Leu Asn Gln Cys
1               5                  10                  15

Ile Glu Glu Arg Tyr Lys Ala Val Cys His Ala Ala Arg Thr Arg Ser
                20                  25                  30

Ile Leu Ser Leu Gly Leu Ala Cys Phe Lys Arg Gln Pro Asp Lys Gly
            35                  40                  45

Glu His Ser Tyr Leu Ala Gln Val Phe Asn Leu Thr Leu Leu Cys Met
        50                  55                  60

Glu Glu Tyr Val Ile Glu Pro Lys Ser Val Gln Phe Leu Ile Gln His
65                  70                  75                  80

Gly Phe Asn Phe Asn Gln Gln Tyr Ala Gln Gly Ile Pro Tyr His Lys
                85                  90                  95

Gly Asn Asp Lys Gly Asp Glu Ser Gln Ser Gln Ser Val Arg Thr Leu
            100                 105                 110

Phe Leu Glu Leu Ile Arg Ala Arg Pro Leu Val Leu His Asn Gly
        115                 120                 125

Leu Ile Asp Leu Val Phe Leu Tyr Gln Asn Phe Tyr Ala His Leu Pro
    130                 135                 140

Glu Ser Leu Gly Thr Phe Thr Ala Asp Leu Cys Glu Met Phe Pro Ala
145                 150                 155                 160

Gly Ile Tyr Asp Thr Lys Tyr Ala Ala Glu Phe His Ala Arg Phe Val
                165                 170                 175

Ala Ser Tyr Leu Glu Tyr Ala Phe Arg Lys Cys Glu Arg Glu Asn Gly
            180                 185                 190

Lys Gln Arg Ala Ala Gly Ser Pro His Leu Thr Leu Glu Phe Cys Asn
        195                 200                 205

Tyr Pro Ser Ser Met Arg Asp His Ile Asp Tyr Arg Cys Cys Leu Pro
    210                 215                 220

Pro Ala Thr His Arg Pro His Pro Thr Ser Ile Cys Asp Asn Phe Ser
225                 230                 235                 240

Ala Tyr Gly Trp Cys Pro Leu Gly Pro Gln Cys Pro Gln Ser His Asp
```

```
                245                 250                 255
Ile Asp Leu Ile Ile Asp Thr Asp Glu Ala Ala Glu Asp Lys Arg
            260                 265                 270
Arg Arg Arg Arg Arg Glu Lys Arg Lys Arg Ala Leu Leu Asn Leu
        275                 280                 285
Pro Gly Thr Gln Thr Ser Gly Glu Ala Lys Asp Gly Pro Lys Lys
    290                 295                 300
Gln Val Cys Gly Asp Ser Ile Lys Pro Glu Glu Thr Glu Gln Glu Val
305                 310                 315                 320
Ala Ala Asp Glu Thr Arg Asn Leu Pro His Ser Lys Gln Gly Asn Lys
                325                 330                 335
Asn Asp Leu Glu Met Gly Ile Lys Ala Ala Arg Pro Glu Ile Ala Asp
            340                 345                 350
Arg Ala Thr Ser Glu Val Pro Gly Ser Gln Ala Ser Pro Asn Pro Val
        355                 360                 365
Pro Gly Asp Gly Leu His Arg Ala Gly Phe Asp Ala Phe Met Thr Gly
    370                 375                 380
Tyr Val Met Ala Tyr Val Glu Val Ser Gln Gly Pro Gln Pro Cys Ser
385                 390                 395                 400
Ser Gly Pro Trp Leu Pro Glu Cys His Asn Lys Val Tyr Leu Ser Gly
                405                 410                 415
Lys Ala Val Pro Leu Thr Val Ala Lys Ser Gln Phe Ser Arg Ser Ser
            420                 425                 430
Lys Ala His Asn Gln Lys Met Lys Leu Thr Trp Gly Ser Ser
        435                 440                 445

<210> SEQ ID NO 104
<211> LENGTH: 346
<212> TYPE: PRT
<213> ORGANISM: Artificial Sequence
<220> FEATURE:
<223> OTHER INFORMATION: G18/D363 Deletion mutant of TOE1

<400> SEQUENCE: 104

Gly Gly Val Ser Lys Ser Thr Thr Ser Gly Glu Glu Leu Val Val Gln
1               5                   10                  15

Val Pro Val Val Asp Val Gln Ser Asn Asn Phe Lys Glu Met Trp Pro
                20                  25                  30

Ser Leu Leu Leu Ala Ile Lys Thr Ala Asn Phe Val Ala Val Asp Thr
            35                  40                  45

Glu Leu Ser Gly Leu Gly Asp Arg Lys Ser Leu Leu Asn Gln Cys Ile
        50                  55                  60

Glu Glu Arg Tyr Lys Ala Val Cys His Ala Ala Arg Thr Arg Ser Ile
65                  70                  75                  80

Leu Ser Leu Gly Leu Ala Cys Phe Lys Arg Gln Pro Asp Lys Gly Glu
                85                  90                  95

His Ser Tyr Leu Ala Gln Val Phe Asn Leu Thr Leu Leu Cys Met Glu
            100                 105                 110

Glu Tyr Val Ile Glu Pro Lys Ser Val Gln Phe Leu Ile Gln His Gly
        115                 120                 125

Phe Asn Phe Asn Gln Gln Tyr Ala Gln Gly Ile Pro Tyr His Lys Gly
    130                 135                 140

Asn Asp Lys Gly Asp Glu Ser Gln Ser Gln Ser Val Arg Thr Leu Phe
145                 150                 155                 160

Leu Glu Leu Ile Arg Ala Arg Arg Pro Leu Val Leu His Asn Gly Leu
```

```
              165                 170                 175
Ile Asp Leu Val Phe Leu Tyr Gln Asn Phe Tyr Ala His Leu Pro Glu
            180                 185                 190

Ser Leu Gly Thr Phe Thr Ala Asp Leu Cys Glu Met Phe Pro Ala Gly
            195                 200                 205

Ile Tyr Asp Thr Lys Tyr Ala Ala Glu Phe His Ala Arg Phe Val Ala
            210                 215                 220

Ser Tyr Leu Glu Tyr Ala Phe Arg Lys Cys Glu Arg Glu Asn Gly Lys
225                 230                 235                 240

Gln Arg Ala Ala Gly Ser Pro His Leu Thr Leu Glu Phe Cys Asn Tyr
            245                 250                 255

Pro Ser Ser Met Arg Asp His Ile Asp Tyr Arg Cys Cys Leu Pro Pro
            260                 265                 270

Ala Thr His Arg Pro His Pro Thr Ser Ile Cys Asp Asn Phe Ser Ala
            275                 280                 285

Tyr Gly Trp Cys Pro Leu Gly Pro Gln Cys Pro Gln Ser His Asp Ile
            290                 295                 300

Asp Leu Ile Ile Asp Thr Asp Glu Ala Ala Glu Asp Lys Arg Arg
305                 310                 315                 320

Arg Arg Arg Arg Glu Lys Arg Lys Arg Ala Leu Leu Asn Leu Pro
            325                 330                 335

Gly Thr Gln Thr Ser Gly Glu Ala Lys Asp
            340                 345

<210> SEQ ID NO 105
<211> LENGTH: 356
<212> TYPE: PRT
<213> ORGANISM: Artificial Sequence
<220> FEATURE:
<223> OTHER INFORMATION: G18/D373 Deletion mutant of TOE1

<400> SEQUENCE: 105

Gly Gly Val Ser Lys Ser Thr Thr Ser Gly Glu Glu Leu Val Val Gln
1               5                   10                  15

Val Pro Val Val Asp Val Gln Ser Asn Asn Phe Lys Glu Met Trp Pro
            20                  25                  30

Ser Leu Leu Leu Ala Ile Lys Thr Ala Asn Phe Val Ala Val Asp Thr
            35                  40                  45

Glu Leu Ser Gly Leu Gly Asp Arg Lys Ser Leu Leu Asn Gln Cys Ile
            50                  55                  60

Glu Glu Arg Tyr Lys Ala Val Cys His Ala Ala Arg Thr Arg Ser Ile
65                  70                  75                  80

Leu Ser Leu Gly Leu Ala Cys Phe Lys Arg Gln Pro Asp Lys Gly Glu
            85                  90                  95

His Ser Tyr Leu Ala Gln Val Phe Asn Leu Thr Leu Leu Cys Met Glu
            100                 105                 110

Glu Tyr Val Ile Glu Pro Lys Ser Val Gln Phe Leu Ile Gln His Gly
            115                 120                 125

Phe Asn Phe Asn Gln Gln Tyr Ala Gln Gly Ile Pro Tyr His Lys Gly
            130                 135                 140

Asn Asp Lys Gly Asp Glu Ser Gln Ser Gln Ser Val Arg Thr Leu Phe
145                 150                 155                 160

Leu Glu Leu Ile Arg Ala Arg Arg Pro Leu Val Leu His Asn Gly Leu
            165                 170                 175

Ile Asp Leu Val Phe Leu Tyr Gln Asn Phe Tyr Ala His Leu Pro Glu
```

```
            180                 185                 190
Ser Leu Gly Thr Phe Thr Ala Asp Leu Cys Glu Met Phe Pro Ala Gly
        195                 200                 205

Ile Tyr Asp Thr Lys Tyr Ala Ala Glu Phe His Ala Arg Phe Val Ala
        210                 215                 220

Ser Tyr Leu Glu Tyr Ala Phe Arg Lys Cys Glu Arg Glu Asn Gly Lys
225                 230                 235                 240

Gln Arg Ala Ala Gly Ser Pro His Leu Thr Leu Glu Phe Cys Asn Tyr
                245                 250                 255

Pro Ser Ser Met Arg Asp His Ile Asp Tyr Arg Cys Cys Leu Pro Pro
            260                 265                 270

Ala Thr His Arg Pro His Pro Thr Ser Ile Cys Asp Asn Phe Ser Ala
        275                 280                 285

Tyr Gly Trp Cys Pro Leu Gly Pro Gln Cys Pro Gln Ser His Asp Ile
    290                 295                 300

Asp Leu Ile Ile Asp Thr Asp Glu Ala Ala Glu Asp Lys Arg Arg
305                 310                 315                 320

Arg Arg Arg Arg Arg Glu Lys Arg Lys Arg Ala Leu Leu Asn Leu Pro
                325                 330                 335

Gly Thr Gln Thr Ser Gly Glu Ala Lys Asp Gly Pro Lys Lys Gln
            340                 345                 350

Val Cys Gly Asp
        355

<210> SEQ ID NO 106
<211> LENGTH: 370
<212> TYPE: PRT
<213> ORGANISM: Artificial Sequence
<220> FEATURE:
<223> OTHER INFORMATION: G18/D387 Deletion mutant of TOE1

<400> SEQUENCE: 106

Gly Gly Val Ser Lys Ser Thr Thr Ser Gly Glu Glu Leu Val Val Gln
1               5                   10                  15

Val Pro Val Val Asp Val Gln Ser Asn Asn Phe Lys Glu Met Trp Pro
            20                  25                  30

Ser Leu Leu Leu Ala Ile Lys Thr Ala Asn Phe Val Ala Val Asp Thr
        35                  40                  45

Glu Leu Ser Gly Leu Gly Asp Arg Lys Ser Leu Leu Asn Gln Cys Ile
    50                  55                  60

Glu Glu Arg Tyr Lys Ala Val Cys His Ala Ala Arg Thr Arg Ser Ile
65                  70                  75                  80

Leu Ser Leu Gly Leu Ala Cys Phe Lys Arg Gln Pro Asp Lys Gly Glu
                85                  90                  95

His Ser Tyr Leu Ala Gln Val Phe Asn Leu Thr Leu Cys Met Glu
            100                 105                 110

Glu Tyr Val Ile Glu Pro Lys Ser Val Gln Phe Leu Ile Gln His Gly
        115                 120                 125

Phe Asn Phe Asn Gln Gln Tyr Ala Gln Gly Ile Pro Tyr His Lys Gly
    130                 135                 140

Asn Asp Lys Gly Asp Glu Ser Gln Ser Gln Ser Val Arg Thr Leu Phe
145                 150                 155                 160

Leu Glu Leu Ile Arg Ala Arg Arg Pro Leu Val Leu His Asn Gly Leu
                165                 170                 175

Ile Asp Leu Val Phe Leu Tyr Gln Asn Phe Tyr Ala His Leu Pro Glu
```

```
                180             185                 190
Ser Leu Gly Thr Phe Thr Ala Asp Leu Cys Glu Met Phe Pro Ala Gly
            195                 200                 205

Ile Tyr Asp Thr Lys Tyr Ala Ala Glu Phe His Ala Arg Phe Val Ala
        210                 215                 220

Ser Tyr Leu Glu Tyr Ala Phe Arg Lys Cys Glu Arg Glu Asn Gly Lys
225                 230                 235                 240

Gln Arg Ala Ala Gly Ser Pro His Leu Thr Leu Glu Phe Cys Asn Tyr
                245                 250                 255

Pro Ser Ser Met Arg Asp His Ile Asp Tyr Arg Cys Cys Leu Pro Pro
            260                 265                 270

Ala Thr His Arg Pro His Pro Thr Ser Ile Cys Asp Asn Phe Ser Ala
        275                 280                 285

Tyr Gly Trp Cys Pro Leu Gly Pro Gln Cys Pro Gln Ser His Asp Ile
    290                 295                 300

Asp Leu Ile Ile Asp Thr Asp Glu Ala Ala Glu Asp Lys Arg Arg
305                 310                 315                 320

Arg Arg Arg Arg Arg Glu Lys Arg Lys Arg Ala Leu Leu Asn Leu Pro
                325                 330                 335

Gly Thr Gln Thr Ser Gly Glu Ala Lys Asp Gly Pro Pro Lys Lys Gln
            340                 345                 350

Val Cys Gly Asp Ser Ile Lys Pro Glu Glu Thr Glu Gln Glu Val Ala
        355                 360                 365

Ala Asp
    370

<210> SEQ ID NO 107
<211> LENGTH: 385
<212> TYPE: PRT
<213> ORGANISM: Artificial Sequence
<220> FEATURE:
<223> OTHER INFORMATION: G18/D402 Deletion mutant of TOE1

<400> SEQUENCE: 107

Gly Gly Val Ser Lys Ser Thr Thr Ser Gly Glu Glu Leu Val Val Gln
1               5                   10                  15

Val Pro Val Val Asp Val Gln Ser Asn Asn Phe Lys Glu Met Trp Pro
            20                  25                  30

Ser Leu Leu Leu Ala Ile Lys Thr Ala Asn Phe Val Ala Val Asp Thr
        35                  40                  45

Glu Leu Ser Gly Leu Gly Asp Arg Lys Ser Leu Leu Asn Gln Cys Ile
    50                  55                  60

Glu Glu Arg Tyr Lys Ala Val Cys His Ala Ala Arg Thr Arg Ser Ile
65                  70                  75                  80

Leu Ser Leu Gly Leu Ala Cys Phe Lys Arg Gln Pro Asp Lys Gly Glu
                85                  90                  95

His Ser Tyr Leu Ala Gln Val Phe Asn Leu Thr Leu Leu Cys Met Glu
            100                 105                 110

Glu Tyr Val Ile Glu Pro Lys Ser Val Gln Phe Leu Ile Gln His Gly
        115                 120                 125

Phe Asn Phe Asn Gln Gln Tyr Ala Gln Gly Ile Pro Tyr His Lys Gly
    130                 135                 140

Asn Asp Lys Gly Asp Glu Ser Gln Ser Gln Ser Val Arg Thr Leu Phe
145                 150                 155                 160

Leu Glu Leu Ile Arg Ala Arg Arg Pro Leu Val Leu His Asn Gly Leu
```

```
                165                 170                 175
Ile Asp Leu Val Phe Leu Tyr Gln Asn Phe Tyr Ala His Leu Pro Glu
            180                 185                 190

Ser Leu Gly Thr Phe Thr Ala Asp Leu Cys Glu Met Phe Pro Ala Gly
            195                 200                 205

Ile Tyr Asp Thr Lys Tyr Ala Ala Glu Phe His Ala Arg Phe Val Ala
            210                 215                 220

Ser Tyr Leu Glu Tyr Ala Phe Arg Lys Cys Glu Arg Glu Asn Gly Lys
225                 230                 235                 240

Gln Arg Ala Ala Gly Ser Pro His Leu Thr Leu Glu Phe Cys Asn Tyr
                245                 250                 255

Pro Ser Ser Met Arg Asp His Ile Asp Tyr Arg Cys Cys Leu Pro Pro
            260                 265                 270

Ala Thr His Arg Pro His Pro Thr Ser Ile Cys Asp Asn Phe Ser Ala
            275                 280                 285

Tyr Gly Trp Cys Pro Leu Gly Pro Gln Cys Pro Gln Ser His Asp Ile
            290                 295                 300

Asp Leu Ile Ile Asp Thr Asp Glu Ala Ala Glu Asp Lys Arg Arg
305                 310                 315                 320

Arg Arg Arg Arg Glu Lys Arg Lys Arg Ala Leu Leu Asn Leu Pro
                325                 330                 335

Gly Thr Gln Thr Ser Gly Glu Ala Lys Asp Gly Pro Pro Lys Lys Gln
            340                 345                 350

Val Cys Gly Asp Ser Ile Lys Pro Glu Glu Thr Glu Gln Glu Val Ala
            355                 360                 365

Ala Asp Glu Thr Arg Asn Leu Pro His Ser Lys Gln Gly Asn Lys Asn
            370                 375                 380

Asp
385

<210> SEQ ID NO 108
<211> LENGTH: 399
<212> TYPE: PRT
<213> ORGANISM: Artificial Sequence
<220> FEATURE:
<223> OTHER INFORMATION: G18/D416 Deletion mutant of TOE1

<400> SEQUENCE: 108

Gly Gly Val Ser Lys Ser Thr Thr Ser Gly Glu Glu Leu Val Val Gln
1               5                   10                  15

Val Pro Val Val Asp Val Gln Ser Asn Asn Phe Lys Glu Met Trp Pro
            20                  25                  30

Ser Leu Leu Leu Ala Ile Lys Thr Ala Asn Phe Val Ala Val Asp Thr
            35                  40                  45

Glu Leu Ser Gly Leu Gly Asp Arg Lys Ser Leu Leu Asn Gln Cys Ile
        50                  55                  60

Glu Glu Arg Tyr Lys Ala Val Cys His Ala Ala Arg Thr Arg Ser Ile
65                  70                  75                  80

Leu Ser Leu Gly Leu Ala Cys Phe Lys Arg Gln Pro Asp Lys Gly Glu
                85                  90                  95

His Ser Tyr Leu Ala Gln Val Phe Asn Leu Thr Leu Leu Cys Met Glu
            100                 105                 110

Glu Tyr Val Ile Glu Pro Lys Ser Val Gln Phe Leu Ile Gln His Gly
            115                 120                 125

Phe Asn Phe Asn Gln Gln Tyr Ala Gln Gly Ile Pro Tyr His Lys Gly
```

```
                    130                 135                 140
Asn Asp Lys Gly Asp Glu Ser Gln Ser Gln Ser Val Arg Thr Leu Phe
145                 150                 155                 160

Leu Glu Leu Ile Arg Ala Arg Arg Pro Leu Val Leu His Asn Gly Leu
                    165                 170                 175

Ile Asp Leu Val Phe Leu Tyr Gln Asn Phe Tyr Ala His Leu Pro Glu
                    180                 185                 190

Ser Leu Gly Thr Phe Thr Ala Asp Leu Cys Glu Met Phe Pro Ala Gly
                    195                 200                 205

Ile Tyr Asp Thr Lys Tyr Ala Ala Glu Phe His Ala Arg Phe Val Ala
                    210                 215                 220

Ser Tyr Leu Glu Tyr Ala Phe Arg Lys Cys Glu Arg Glu Asn Gly Lys
225                 230                 235                 240

Gln Arg Ala Ala Gly Ser Pro His Leu Thr Leu Glu Phe Cys Asn Tyr
                    245                 250                 255

Pro Ser Ser Met Arg Asp His Ile Asp Tyr Arg Cys Cys Leu Pro Pro
                    260                 265                 270

Ala Thr His Arg Pro His Pro Thr Ser Ile Cys Asp Asn Phe Ser Ala
                    275                 280                 285

Tyr Gly Trp Cys Pro Leu Gly Pro Gln Cys Pro Gln Ser His Asp Ile
                    290                 295                 300

Asp Leu Ile Ile Asp Thr Asp Glu Ala Ala Glu Asp Lys Arg Arg
305                 310                 315                 320

Arg Arg Arg Arg Glu Lys Arg Lys Arg Ala Leu Leu Asn Leu Pro
                    325                 330                 335

Gly Thr Gln Thr Ser Gly Glu Ala Lys Asp Gly Pro Pro Lys Lys Gln
                    340                 345                 350

Val Cys Gly Asp Ser Ile Lys Pro Glu Glu Thr Glu Gln Glu Val Ala
                    355                 360                 365

Ala Asp Glu Thr Arg Asn Leu Pro His Ser Lys Gln Gly Asn Lys Asn
                    370                 375                 380

Asp Leu Glu Met Gly Ile Lys Ala Ala Arg Pro Glu Ile Ala Asp
385                 390                 395

<210> SEQ ID NO 109
<211> LENGTH: 418
<212> TYPE: PRT
<213> ORGANISM: Artificial Sequence
<220> FEATURE:
<223> OTHER INFORMATION: G18/D435 Deletion mutant of TOE1

<400> SEQUENCE: 109

Gly Gly Val Ser Lys Ser Thr Thr Ser Gly Glu Glu Leu Val Val Gln
1               5                   10                  15

Val Pro Val Val Asp Val Gln Ser Asn Asn Phe Lys Glu Met Trp Pro
                    20                  25                  30

Ser Leu Leu Leu Ala Ile Lys Thr Ala Asn Phe Val Ala Val Asp Thr
                    35                  40                  45

Glu Leu Ser Gly Leu Gly Asp Arg Lys Ser Leu Leu Asn Gln Cys Ile
                    50                  55                  60

Glu Glu Arg Tyr Lys Ala Val Cys His Ala Ala Arg Thr Arg Ser Ile
65                  70                  75                  80

Leu Ser Leu Gly Leu Ala Cys Phe Lys Arg Gln Pro Asp Lys Gly Glu
                    85                  90                  95

His Ser Tyr Leu Ala Gln Val Phe Asn Leu Thr Leu Leu Cys Met Glu
```

```
            100                 105                 110
Glu Tyr Val Ile Glu Pro Lys Ser Val Gln Phe Leu Ile Gln His Gly
            115                 120                 125

Phe Asn Phe Asn Gln Gln Tyr Ala Gln Gly Ile Pro Tyr His Lys Gly
    130                 135                 140

Asn Asp Lys Gly Asp Glu Ser Gln Ser Gln Ser Val Arg Thr Leu Phe
145                 150                 155                 160

Leu Glu Leu Ile Arg Ala Arg Arg Pro Leu Val Leu His Asn Gly Leu
                165                 170                 175

Ile Asp Leu Val Phe Leu Tyr Gln Asn Phe Tyr Ala His Leu Pro Glu
            180                 185                 190

Ser Leu Gly Thr Phe Thr Ala Asp Leu Cys Glu Met Phe Pro Ala Gly
            195                 200                 205

Ile Tyr Asp Thr Lys Tyr Ala Ala Glu Phe His Ala Arg Phe Val Ala
            210                 215                 220

Ser Tyr Leu Glu Tyr Ala Phe Arg Lys Cys Glu Arg Glu Asn Gly Lys
225                 230                 235                 240

Gln Arg Ala Ala Gly Ser Pro His Leu Thr Leu Glu Phe Cys Asn Tyr
                245                 250                 255

Pro Ser Ser Met Arg Asp His Ile Asp Tyr Arg Cys Cys Leu Pro Pro
            260                 265                 270

Ala Thr His Arg Pro His Pro Thr Ser Ile Cys Asp Asn Phe Ser Ala
            275                 280                 285

Tyr Gly Trp Cys Pro Leu Gly Pro Gln Cys Pro Gln Ser His Asp Ile
            290                 295                 300

Asp Leu Ile Ile Asp Thr Asp Glu Ala Ala Ala Glu Asp Lys Arg Arg
305                 310                 315                 320

Arg Arg Arg Arg Glu Lys Arg Lys Arg Ala Leu Leu Asn Leu Pro
                325                 330                 335

Gly Thr Gln Thr Ser Gly Glu Ala Lys Asp Gly Pro Pro Lys Lys Gln
            340                 345                 350

Val Cys Gly Asp Ser Ile Lys Pro Glu Glu Thr Glu Gln Glu Val Ala
            355                 360                 365

Ala Asp Glu Thr Arg Asn Leu Pro His Ser Lys Gln Gly Asn Lys Asn
    370                 375                 380

Asp Leu Glu Met Gly Ile Lys Ala Ala Arg Pro Glu Ile Ala Asp Arg
385                 390                 395                 400

Ala Thr Ser Glu Val Pro Gly Ser Gln Ala Ser Pro Asn Pro Val Pro
                405                 410                 415

Gly Asp

<210> SEQ ID NO 110
<211> LENGTH: 426
<212> TYPE: PRT
<213> ORGANISM: Artificial Sequence
<220> FEATURE:
<223> OTHER INFORMATION: G18/D443 Deletion mutant of TOE1

<400> SEQUENCE: 110

Gly Gly Val Ser Lys Ser Thr Thr Ser Gly Glu Glu Leu Val Val Gln
1               5                   10                  15

Val Pro Val Val Asp Val Gln Ser Asn Asn Phe Lys Glu Met Trp Pro
            20                  25                  30

Ser Leu Leu Leu Ala Ile Lys Thr Ala Asn Phe Val Ala Val Asp Thr
        35                  40                  45
```

-continued

```
Glu Leu Ser Gly Leu Gly Asp Arg Lys Ser Leu Leu Asn Gln Cys Ile
 50                  55                  60

Glu Glu Arg Tyr Lys Ala Val Cys His Ala Ala Arg Thr Arg Ser Ile
 65                  70                  75                  80

Leu Ser Leu Gly Leu Ala Cys Phe Lys Arg Gln Pro Asp Lys Gly Glu
                 85                  90                  95

His Ser Tyr Leu Ala Gln Val Phe Asn Leu Thr Leu Leu Cys Met Glu
            100                 105                 110

Glu Tyr Val Ile Glu Pro Lys Ser Val Gln Phe Leu Ile Gln His Gly
            115                 120                 125

Phe Asn Phe Asn Gln Gln Tyr Ala Gln Gly Ile Pro Tyr His Lys Gly
130                 135                 140

Asn Asp Lys Gly Asp Glu Ser Gln Ser Gln Ser Val Arg Thr Leu Phe
145                 150                 155                 160

Leu Glu Leu Ile Arg Ala Arg Arg Pro Leu Val Leu His Asn Gly Leu
                165                 170                 175

Ile Asp Leu Val Phe Leu Tyr Gln Asn Phe Tyr Ala His Leu Pro Glu
            180                 185                 190

Ser Leu Gly Thr Phe Thr Ala Asp Leu Cys Glu Met Phe Pro Ala Gly
            195                 200                 205

Ile Tyr Asp Thr Lys Tyr Ala Ala Glu Phe His Ala Arg Phe Val Ala
210                 215                 220

Ser Tyr Leu Glu Tyr Ala Phe Arg Lys Cys Glu Arg Glu Asn Gly Lys
225                 230                 235                 240

Gln Arg Ala Ala Gly Ser Pro His Leu Thr Leu Glu Phe Cys Asn Tyr
                245                 250                 255

Pro Ser Ser Met Arg Asp His Ile Asp Tyr Arg Cys Cys Leu Pro Pro
            260                 265                 270

Ala Thr His Arg Pro His Pro Thr Ser Ile Cys Asp Asn Phe Ser Ala
            275                 280                 285

Tyr Gly Trp Cys Pro Leu Gly Pro Gln Cys Pro Gln Ser His Asp Ile
290                 295                 300

Asp Leu Ile Ile Asp Thr Asp Glu Ala Ala Glu Asp Lys Arg Arg
305                 310                 315                 320

Arg Arg Arg Arg Glu Lys Arg Lys Arg Ala Leu Leu Asn Leu Pro
                325                 330                 335

Gly Thr Gln Thr Ser Gly Glu Ala Lys Asp Gly Pro Pro Lys Lys Gln
            340                 345                 350

Val Cys Gly Asp Ser Ile Lys Pro Glu Glu Thr Glu Gln Glu Val Ala
            355                 360                 365

Ala Asp Glu Thr Arg Asn Leu Pro His Ser Lys Gln Gly Asn Lys Asn
370                 375                 380

Asp Leu Glu Met Gly Ile Lys Ala Ala Arg Pro Glu Ile Ala Asp Arg
385                 390                 395                 400

Ala Thr Ser Glu Val Pro Gly Ser Gln Ala Ser Pro Asn Pro Val Pro
                405                 410                 415

Gly Asp Gly Leu His Arg Ala Gly Phe Asp
            420                 425
```

<210> SEQ ID NO 111
<211> LENGTH: 493
<212> TYPE: PRT
<213> ORGANISM: Artificial Sequence
<220> FEATURE:

<223> OTHER INFORMATION: G18/S510 Deletion mutant of TOE1

<400> SEQUENCE: 111

```
Gly Gly Val Ser Lys Ser Thr Thr Ser Gly Glu Glu Leu Val Val Gln
1               5                   10                  15

Val Pro Val Val Asp Val Gln Ser Asn Asn Phe Lys Glu Met Trp Pro
            20                  25                  30

Ser Leu Leu Leu Ala Ile Lys Thr Ala Asn Phe Val Ala Val Asp Thr
        35                  40                  45

Glu Leu Ser Gly Leu Gly Asp Arg Lys Ser Leu Leu Asn Gln Cys Ile
50                  55                  60

Glu Glu Arg Tyr Lys Ala Val Cys His Ala Ala Arg Thr Arg Ser Ile
65                  70                  75                  80

Leu Ser Leu Gly Leu Ala Cys Phe Lys Arg Gln Pro Asp Lys Gly Glu
                85                  90                  95

His Ser Tyr Leu Ala Gln Val Phe Asn Leu Thr Leu Leu Cys Met Glu
            100                 105                 110

Glu Tyr Val Ile Glu Pro Lys Ser Val Gln Phe Leu Ile Gln His Gly
        115                 120                 125

Phe Asn Phe Asn Gln Gln Tyr Ala Gln Gly Ile Pro Tyr His Lys Gly
130                 135                 140

Asn Asp Lys Gly Asp Glu Ser Gln Ser Gln Ser Val Arg Thr Leu Phe
145                 150                 155                 160

Leu Glu Leu Ile Arg Ala Arg Arg Pro Leu Val Leu His Asn Gly Leu
                165                 170                 175

Ile Asp Leu Val Phe Leu Tyr Gln Asn Phe Tyr Ala His Leu Pro Glu
            180                 185                 190

Ser Leu Gly Thr Phe Thr Ala Asp Leu Cys Glu Met Phe Pro Ala Gly
        195                 200                 205

Ile Tyr Asp Thr Lys Tyr Ala Ala Glu Phe His Ala Arg Phe Val Ala
210                 215                 220

Ser Tyr Leu Glu Tyr Ala Phe Arg Lys Cys Glu Arg Glu Asn Gly Lys
225                 230                 235                 240

Gln Arg Ala Ala Gly Ser Pro His Leu Thr Leu Glu Phe Cys Asn Tyr
                245                 250                 255

Pro Ser Ser Met Arg Asp His Ile Asp Tyr Arg Cys Cys Leu Pro Pro
            260                 265                 270

Ala Thr His Arg Pro His Pro Thr Ser Ile Cys Asp Asn Phe Ser Ala
        275                 280                 285

Tyr Gly Trp Cys Pro Leu Gly Pro Gln Cys Pro Gln Ser His Asp Ile
290                 295                 300

Asp Leu Ile Ile Asp Thr Asp Glu Ala Ala Glu Asp Lys Arg Arg
305                 310                 315                 320

Arg Arg Arg Arg Glu Lys Arg Lys Arg Ala Leu Leu Asn Leu Pro
                325                 330                 335

Gly Thr Gln Thr Ser Gly Glu Ala Lys Asp Gly Pro Lys Lys Gln
            340                 345                 350

Val Cys Gly Asp Ser Ile Lys Pro Glu Glu Thr Glu Gln Glu Val Ala
        355                 360                 365

Ala Asp Glu Thr Arg Asn Leu Pro His Ser Lys Gln Gly Asn Lys Asn
370                 375                 380

Asp Leu Glu Met Gly Ile Lys Ala Ala Arg Pro Glu Ile Ala Asp Arg
385                 390                 395                 400
```

```
Ala Thr Ser Glu Val Pro Gly Ser Gln Ala Ser Pro Asn Pro Val Pro
                405                 410                 415

Gly Asp Gly Leu His Arg Ala Gly Phe Asp Ala Phe Met Thr Gly Tyr
            420                 425                 430

Val Met Ala Tyr Val Glu Val Ser Gln Gly Pro Gln Pro Cys Ser Ser
        435                 440                 445

Gly Pro Trp Leu Pro Glu Cys His Asn Lys Val Tyr Leu Ser Gly Lys
    450                 455                 460

Ala Val Pro Leu Thr Val Ala Lys Ser Gln Phe Ser Arg Ser Ser Lys
465                 470                 475                 480

Ala His Asn Gln Lys Met Lys Leu Thr Trp Gly Ser Ser
                485                 490
```

<210> SEQ ID NO 112
<211> LENGTH: 356
<212> TYPE: PRT
<213> ORGANISM: Artificial Sequence
<220> FEATURE:
<223> OTHER INFORMATION: G8/D363 Deletion mutant of TOE1

<400> SEQUENCE: 112

```
Gly Ala Val Ser Thr Pro Ala Ala Ser Asp Gly Gly Val Ser Lys Ser
1               5                   10                  15

Thr Thr Ser Gly Glu Glu Leu Val Val Gln Val Pro Val Val Asp Val
            20                  25                  30

Gln Ser Asn Asn Phe Lys Glu Met Trp Pro Ser Leu Leu Leu Ala Ile
        35                  40                  45

Lys Thr Ala Asn Phe Val Ala Val Asp Thr Glu Leu Ser Gly Leu Gly
    50                  55                  60

Asp Arg Lys Ser Leu Leu Asn Gln Cys Ile Glu Glu Arg Tyr Lys Ala
65                  70                  75                  80

Val Cys His Ala Ala Arg Thr Arg Ser Ile Leu Ser Leu Gly Leu Ala
                85                  90                  95

Cys Phe Lys Arg Gln Pro Asp Lys Gly Glu His Ser Tyr Leu Ala Gln
                100                 105                 110

Val Phe Asn Leu Thr Leu Leu Cys Met Glu Glu Tyr Val Ile Glu Pro
            115                 120                 125

Lys Ser Val Gln Phe Leu Ile Gln His Gly Phe Asn Phe Asn Gln Gln
        130                 135                 140

Tyr Ala Gln Gly Ile Pro Tyr His Lys Gly Asn Asp Lys Gly Asp Glu
145                 150                 155                 160

Ser Gln Ser Gln Ser Val Arg Thr Leu Phe Leu Glu Leu Ile Arg Ala
                165                 170                 175

Arg Arg Pro Leu Val Leu His Asn Gly Leu Ile Asp Leu Val Phe Leu
                180                 185                 190

Tyr Gln Asn Phe Tyr Ala His Leu Pro Glu Ser Leu Gly Thr Phe Thr
            195                 200                 205

Ala Asp Leu Cys Glu Met Phe Pro Ala Gly Ile Tyr Asp Thr Lys Tyr
        210                 215                 220

Ala Ala Glu Phe His Ala Arg Phe Val Ala Ser Tyr Leu Glu Tyr Ala
225                 230                 235                 240

Phe Arg Lys Cys Glu Arg Glu Asn Gly Lys Gln Arg Ala Ala Gly Ser
                245                 250                 255

Pro His Leu Thr Leu Glu Phe Cys Asn Tyr Pro Ser Ser Met Arg Asp
            260                 265                 270
```

His Ile Asp Tyr Arg Cys Cys Leu Pro Pro Ala Thr His Arg Pro His
            275                 280                 285

Pro Thr Ser Ile Cys Asp Asn Phe Ser Ala Tyr Gly Trp Cys Pro Leu
290                 295                 300

Gly Pro Gln Cys Pro Gln Ser His Asp Ile Asp Leu Ile Ile Asp Thr
305                 310                 315                 320

Asp Glu Ala Ala Ala Glu Asp Lys Arg Arg Arg Arg Arg Arg Arg Glu
                325                 330                 335

Lys Arg Lys Arg Ala Leu Leu Asn Leu Pro Gly Thr Gln Thr Ser Gly
                340                 345                 350

Glu Ala Lys Asp
        355

<210> SEQ ID NO 113
<211> LENGTH: 366
<212> TYPE: PRT
<213> ORGANISM: Artificial Sequence
<220> FEATURE:
<223> OTHER INFORMATION: G8/D373 Deletion mutant of TOE1

<400> SEQUENCE: 113

Gly Ala Val Ser Thr Pro Ala Ala Ser Asp Gly Gly Val Ser Lys Ser
1               5                   10                  15

Thr Thr Ser Gly Glu Glu Leu Val Val Gln Val Pro Val Val Asp Val
            20                  25                  30

Gln Ser Asn Asn Phe Lys Glu Met Trp Pro Ser Leu Leu Leu Ala Ile
        35                  40                  45

Lys Thr Ala Asn Phe Val Ala Val Asp Thr Glu Leu Ser Gly Leu Gly
50                  55                  60

Asp Arg Lys Ser Leu Leu Asn Gln Cys Ile Glu Glu Arg Tyr Lys Ala
65                  70                  75                  80

Val Cys His Ala Ala Arg Thr Arg Ser Ile Leu Ser Leu Gly Leu Ala
                85                  90                  95

Cys Phe Lys Arg Gln Pro Asp Lys Gly Glu His Ser Tyr Leu Ala Gln
            100                 105                 110

Val Phe Asn Leu Thr Leu Leu Cys Met Glu Glu Tyr Val Ile Glu Pro
        115                 120                 125

Lys Ser Val Gln Phe Leu Ile Gln His Gly Phe Asn Phe Asn Gln Gln
130                 135                 140

Tyr Ala Gln Gly Ile Pro Tyr His Lys Gly Asn Asp Lys Gly Asp Glu
145                 150                 155                 160

Ser Gln Ser Gln Ser Val Arg Thr Leu Phe Leu Glu Leu Ile Arg Ala
                165                 170                 175

Arg Arg Pro Leu Val Leu His Asn Gly Leu Ile Asp Leu Val Phe Leu
            180                 185                 190

Tyr Gln Asn Phe Tyr Ala His Leu Pro Glu Ser Leu Gly Thr Phe Thr
        195                 200                 205

Ala Asp Leu Cys Glu Met Phe Pro Ala Gly Ile Tyr Asp Thr Lys Tyr
210                 215                 220

Ala Ala Glu Phe His Ala Arg Phe Val Ala Ser Tyr Leu Glu Tyr Ala
225                 230                 235                 240

Phe Arg Lys Cys Glu Arg Glu Asn Gly Lys Gln Arg Ala Ala Gly Ser
                245                 250                 255

Pro His Leu Thr Leu Glu Phe Cys Asn Tyr Pro Ser Ser Met Arg Asp
            260                 265                 270

His Ile Asp Tyr Arg Cys Cys Leu Pro Pro Ala Thr His Arg Pro His
            275                 280                 285

Pro Thr Ser Ile Cys Asp Asn Phe Ser Ala Tyr Gly Trp Cys Pro Leu
        290                 295                 300

Gly Pro Gln Cys Pro Gln Ser His Asp Ile Asp Leu Ile Ile Asp Thr
305                 310                 315                 320

Asp Glu Ala Ala Ala Glu Asp Lys Arg Arg Arg Arg Arg Arg Arg Glu
                325                 330                 335

Lys Arg Lys Arg Ala Leu Leu Asn Pro Gly Thr Gln Thr Ser Gly
                340                 345                 350

Glu Ala Lys Asp Gly Pro Pro Lys Lys Gln Val Cys Gly Asp
            355                 360                 365

<210> SEQ ID NO 114
<211> LENGTH: 380
<212> TYPE: PRT
<213> ORGANISM: Artificial Sequence
<220> FEATURE:
<223> OTHER INFORMATION: G8/D387 Deletion mutant of TOE1

<400> SEQUENCE: 114

Gly Ala Val Ser Thr Pro Ala Ala Ser Asp Gly Gly Val Ser Lys Ser
1               5                   10                  15

Thr Thr Ser Gly Glu Glu Leu Val Val Gln Val Pro Val Val Asp Val
                20                  25                  30

Gln Ser Asn Asn Phe Lys Glu Met Trp Pro Ser Leu Leu Leu Ala Ile
            35                  40                  45

Lys Thr Ala Asn Phe Val Ala Val Asp Thr Glu Leu Ser Gly Leu Gly
        50                  55                  60

Asp Arg Lys Ser Leu Leu Asn Gln Cys Ile Glu Glu Arg Tyr Lys Ala
65                  70                  75                  80

Val Cys His Ala Ala Arg Thr Arg Ser Ile Leu Ser Leu Gly Leu Ala
                85                  90                  95

Cys Phe Lys Arg Gln Pro Asp Lys Gly Glu His Ser Tyr Leu Ala Gln
            100                 105                 110

Val Phe Asn Leu Thr Leu Leu Cys Met Glu Glu Tyr Val Ile Glu Pro
        115                 120                 125

Lys Ser Val Gln Phe Leu Ile Gln His Gly Phe Asn Phe Asn Gln Gln
    130                 135                 140

Tyr Ala Gln Gly Ile Pro Tyr His Lys Gly Asn Asp Lys Gly Asp Glu
145                 150                 155                 160

Ser Gln Ser Gln Ser Val Arg Thr Leu Phe Leu Glu Leu Ile Arg Ala
                165                 170                 175

Arg Arg Pro Leu Val Leu His Asn Gly Leu Ile Asp Leu Val Phe Leu
            180                 185                 190

Tyr Gln Asn Phe Tyr Ala His Leu Pro Glu Ser Leu Gly Thr Phe Thr
        195                 200                 205

Ala Asp Leu Cys Glu Met Phe Pro Ala Gly Ile Tyr Asp Thr Lys Tyr
    210                 215                 220

Ala Ala Glu Phe His Ala Arg Phe Val Ala Ser Tyr Leu Glu Tyr Ala
225                 230                 235                 240

Phe Arg Lys Cys Glu Arg Glu Asn Gly Lys Gln Arg Ala Ala Gly Ser
                245                 250                 255

Pro His Leu Thr Leu Glu Phe Cys Asn Tyr Pro Ser Ser Met Arg Asp
            260                 265                 270

```
His Ile Asp Tyr Arg Cys Cys Leu Pro Pro Ala Thr His Arg Pro His
            275                 280                 285

Pro Thr Ser Ile Cys Asp Asn Phe Ser Ala Tyr Gly Trp Cys Pro Leu
    290                 295                 300

Gly Pro Gln Cys Pro Gln Ser His Asp Ile Asp Leu Ile Ile Asp Thr
305                 310                 315                 320

Asp Glu Ala Ala Ala Glu Asp Lys Arg Arg Arg Arg Arg Arg Arg Glu
                325                 330                 335

Lys Arg Lys Arg Ala Leu Leu Asn Leu Pro Gly Thr Gln Thr Ser Gly
                340                 345                 350

Glu Ala Lys Asp Gly Pro Pro Lys Lys Gln Val Cys Gly Asp Ser Ile
                355                 360                 365

Lys Pro Glu Glu Thr Glu Gln Glu Val Ala Ala Asp
                370                 375                 380

<210> SEQ ID NO 115
<211> LENGTH: 395
<212> TYPE: PRT
<213> ORGANISM: Artificial Sequence
<220> FEATURE:
<223> OTHER INFORMATION: G8/D402 Deletion mutant of TOE1

<400> SEQUENCE: 115

Gly Ala Val Ser Thr Pro Ala Ala Ser Asp Gly Gly Val Ser Lys Ser
1               5                   10                  15

Thr Thr Ser Gly Glu Glu Leu Val Val Gln Val Pro Val Val Asp Val
                20                  25                  30

Gln Ser Asn Asn Phe Lys Glu Met Trp Pro Ser Leu Leu Leu Ala Ile
            35                  40                  45

Lys Thr Ala Asn Phe Val Ala Val Asp Thr Glu Leu Ser Gly Leu Gly
    50                  55                  60

Asp Arg Lys Ser Leu Leu Asn Gln Cys Ile Glu Glu Arg Tyr Lys Ala
65                  70                  75                  80

Val Cys His Ala Ala Arg Thr Arg Ser Ile Leu Ser Leu Gly Leu Ala
                85                  90                  95

Cys Phe Lys Arg Gln Pro Asp Lys Gly Glu His Ser Tyr Leu Ala Gln
            100                 105                 110

Val Phe Asn Leu Thr Leu Leu Cys Met Glu Glu Tyr Val Ile Glu Pro
        115                 120                 125

Lys Ser Val Gln Phe Leu Ile Gln His Gly Phe Asn Phe Asn Gln Gln
130                 135                 140

Tyr Ala Gln Gly Ile Pro Tyr His Lys Gly Asn Asp Lys Gly Asp Glu
145                 150                 155                 160

Ser Gln Ser Gln Ser Val Arg Thr Leu Phe Leu Glu Leu Ile Arg Ala
                165                 170                 175

Arg Arg Pro Leu Val Leu His Asn Gly Leu Ile Asp Leu Val Phe Leu
            180                 185                 190

Tyr Gln Asn Phe Tyr Ala His Leu Pro Glu Ser Leu Gly Thr Phe Thr
        195                 200                 205

Ala Asp Leu Cys Glu Met Phe Pro Ala Gly Ile Tyr Asp Thr Lys Tyr
    210                 215                 220

Ala Ala Glu Phe His Ala Arg Phe Val Ala Ser Tyr Leu Glu Tyr Ala
225                 230                 235                 240

Phe Arg Lys Cys Glu Arg Glu Asn Gly Lys Gln Arg Ala Ala Gly Ser
                245                 250                 255
```

```
Pro His Leu Thr Leu Glu Phe Cys Asn Tyr Pro Ser Ser Met Arg Asp
            260                 265                 270

His Ile Asp Tyr Arg Cys Cys Leu Pro Pro Ala Thr His Arg Pro His
        275                 280                 285

Pro Thr Ser Ile Cys Asp Asn Phe Ser Ala Tyr Gly Trp Cys Pro Leu
    290                 295                 300

Gly Pro Gln Cys Pro Gln Ser His Asp Ile Asp Leu Ile Ile Asp Thr
305                 310                 315                 320

Asp Glu Ala Ala Ala Glu Asp Lys Arg Arg Arg Arg Arg Arg Arg Glu
                325                 330                 335

Lys Arg Lys Arg Ala Leu Leu Asn Leu Pro Gly Thr Gln Thr Ser Gly
            340                 345                 350

Glu Ala Lys Asp Gly Pro Pro Lys Lys Gln Val Cys Gly Asp Ser Ile
        355                 360                 365

Lys Pro Glu Glu Thr Glu Gln Glu Val Ala Ala Asp Glu Thr Arg Asn
    370                 375                 380

Leu Pro His Ser Lys Gln Gly Asn Lys Asn Asp
385                 390                 395

<210> SEQ ID NO 116
<211> LENGTH: 409
<212> TYPE: PRT
<213> ORGANISM: Artificial Sequence
<220> FEATURE:
<223> OTHER INFORMATION: G8/D416 Deletion mutant of TOE1

<400> SEQUENCE: 116

Gly Ala Val Ser Thr Pro Ala Ala Ser Asp Gly Gly Val Ser Lys Ser
1               5                   10                  15

Thr Thr Ser Gly Glu Glu Leu Val Val Gln Val Pro Val Asp Val
            20                  25                  30

Gln Ser Asn Asn Phe Lys Glu Met Trp Pro Ser Leu Leu Leu Ala Ile
        35                  40                  45

Lys Thr Ala Asn Phe Val Ala Val Asp Thr Glu Leu Ser Gly Leu Gly
    50                  55                  60

Asp Arg Lys Ser Leu Leu Asn Gln Cys Ile Glu Arg Tyr Lys Ala
65                  70                  75                  80

Val Cys His Ala Ala Arg Thr Arg Ser Ile Leu Ser Leu Gly Leu Ala
            85                  90                  95

Cys Phe Lys Arg Gln Pro Asp Lys Gly Glu His Ser Tyr Leu Ala Gln
        100                 105                 110

Val Phe Asn Leu Thr Leu Leu Cys Met Glu Glu Tyr Val Ile Glu Pro
    115                 120                 125

Lys Ser Val Gln Phe Leu Ile Gln His Gly Phe Asn Phe Asn Gln Gln
130                 135                 140

Tyr Ala Gln Gly Ile Pro Tyr His Lys Gly Asn Asp Lys Gly Asp Glu
145                 150                 155                 160

Ser Gln Ser Gln Ser Val Arg Thr Leu Phe Leu Glu Leu Ile Arg Ala
            165                 170                 175

Arg Arg Pro Leu Val Leu His Asn Gly Leu Ile Asp Leu Val Phe Leu
        180                 185                 190

Tyr Gln Asn Phe Tyr Ala His Leu Pro Glu Ser Leu Gly Thr Phe Thr
    195                 200                 205

Ala Asp Leu Cys Glu Met Phe Pro Ala Gly Ile Tyr Asp Thr Lys Tyr
210                 215                 220
```

Ala Ala Glu Phe His Ala Arg Phe Val Ala Ser Tyr Leu Glu Tyr Ala
225                 230                 235                 240

Phe Arg Lys Cys Glu Arg Glu Asn Gly Lys Gln Arg Ala Ala Gly Ser
            245                 250                 255

Pro His Leu Thr Leu Glu Phe Cys Asn Tyr Pro Ser Ser Met Arg Asp
            260                 265                 270

His Ile Asp Tyr Arg Cys Cys Leu Pro Pro Ala Thr His Arg Pro His
            275                 280                 285

Pro Thr Ser Ile Cys Asp Asn Phe Ser Ala Tyr Gly Trp Cys Pro Leu
290                 295                 300

Gly Pro Gln Cys Pro Gln Ser His Asp Ile Asp Leu Ile Ile Asp Thr
305                 310                 315                 320

Asp Glu Ala Ala Ala Glu Asp Lys Arg Arg Arg Arg Arg Arg Arg Glu
            325                 330                 335

Lys Arg Lys Arg Ala Leu Leu Asn Leu Pro Gly Thr Gln Thr Ser Gly
            340                 345                 350

Glu Ala Lys Asp Gly Pro Pro Lys Lys Gln Val Cys Gly Asp Ser Ile
            355                 360                 365

Lys Pro Glu Glu Thr Glu Gln Glu Val Ala Ala Asp Glu Thr Arg Asn
370                 375                 380

Leu Pro His Ser Lys Gln Gly Asn Lys Asn Asp Leu Glu Met Gly Ile
385                 390                 395                 400

Lys Ala Ala Arg Pro Glu Ile Ala Asp
            405

<210> SEQ ID NO 117
<211> LENGTH: 428
<212> TYPE: PRT
<213> ORGANISM: Artificial Sequence
<220> FEATURE:
<223> OTHER INFORMATION: G8/D435 Deletion mutant of TOE1

<400> SEQUENCE: 117

Gly Ala Val Ser Thr Pro Ala Ala Ser Asp Gly Gly Val Ser Lys Ser
1               5                   10                  15

Thr Thr Ser Gly Glu Glu Leu Val Val Gln Val Pro Val Val Asp Val
            20                  25                  30

Gln Ser Asn Asn Phe Lys Glu Met Trp Pro Ser Leu Leu Leu Ala Ile
            35                  40                  45

Lys Thr Ala Asn Phe Val Ala Val Asp Thr Glu Leu Ser Gly Leu Gly
        50                  55                  60

Asp Arg Lys Ser Leu Leu Asn Gln Cys Ile Glu Arg Tyr Lys Ala
65                  70                  75                  80

Val Cys His Ala Ala Arg Thr Arg Ser Ile Leu Ser Leu Gly Leu Ala
                85                  90                  95

Cys Phe Lys Arg Gln Pro Asp Lys Gly Glu His Ser Tyr Leu Ala Gln
            100                 105                 110

Val Phe Asn Leu Thr Leu Leu Cys Met Glu Glu Tyr Val Ile Glu Pro
            115                 120                 125

Lys Ser Val Gln Phe Leu Ile Gln His Gly Phe Asn Phe Asn Gln Gln
        130                 135                 140

Tyr Ala Gln Gly Ile Pro Tyr His Lys Gly Asn Asp Lys Gly Asp Glu
145                 150                 155                 160

Ser Gln Ser Gln Ser Val Arg Thr Leu Phe Leu Glu Leu Ile Arg Ala
                165                 170                 175

```
Arg Arg Pro Leu Val Leu His Asn Gly Ile Asp Leu Val Phe Leu
            180                 185                 190

Tyr Gln Asn Phe Tyr Ala His Leu Pro Glu Ser Leu Gly Thr Phe Thr
        195                 200                 205

Ala Asp Leu Cys Glu Met Phe Pro Ala Gly Ile Tyr Asp Thr Lys Tyr
    210                 215                 220

Ala Ala Glu Phe His Ala Arg Phe Val Ala Ser Tyr Leu Glu Tyr Ala
225                 230                 235                 240

Phe Arg Lys Cys Glu Arg Glu Asn Gly Lys Gln Arg Ala Ala Gly Ser
                245                 250                 255

Pro His Leu Thr Leu Glu Phe Cys Asn Tyr Pro Ser Ser Met Arg Asp
            260                 265                 270

His Ile Asp Tyr Arg Cys Cys Leu Pro Pro Ala Thr His Arg Pro His
        275                 280                 285

Pro Thr Ser Ile Cys Asp Asn Phe Ser Ala Tyr Gly Trp Cys Pro Leu
    290                 295                 300

Gly Pro Gln Cys Pro Gln Ser His Asp Ile Asp Leu Ile Ile Asp Thr
305                 310                 315                 320

Asp Glu Ala Ala Ala Glu Asp Lys Arg Arg Arg Arg Arg Arg Arg Glu
                325                 330                 335

Lys Arg Lys Arg Ala Leu Leu Asn Leu Pro Gly Thr Gln Thr Ser Gly
            340                 345                 350

Glu Ala Lys Asp Gly Pro Pro Lys Lys Gln Val Cys Gly Asp Ser Ile
        355                 360                 365

Lys Pro Glu Glu Thr Gln Glu Val Ala Ala Asp Glu Thr Arg Asn
    370                 375                 380

Leu Pro His Ser Lys Gln Gly Asn Lys Asn Asp Leu Glu Met Gly Ile
385                 390                 395                 400

Lys Ala Ala Arg Pro Glu Ile Ala Asp Arg Ala Thr Ser Glu Val Pro
                405                 410                 415

Gly Ser Gln Ala Ser Pro Asn Pro Val Pro Gly Asp
            420                 425

<210> SEQ ID NO 118
<211> LENGTH: 436
<212> TYPE: PRT
<213> ORGANISM: Artificial Sequence
<220> FEATURE:
<223> OTHER INFORMATION: G8/D443 Deletion mutant of TOE1

<400> SEQUENCE: 118

Gly Ala Val Ser Thr Pro Ala Ala Ser Asp Gly Val Ser Lys Ser
1               5                   10                  15

Thr Thr Ser Gly Glu Glu Leu Val Val Gln Val Pro Val Asp Val
            20                  25                  30

Gln Ser Asn Asn Phe Lys Glu Met Trp Pro Ser Leu Leu Ala Ile
        35                  40                  45

Lys Thr Ala Asn Phe Val Ala Val Asp Thr Glu Leu Ser Gly Leu Gly
    50                  55                  60

Asp Arg Lys Ser Leu Leu Asn Gln Cys Ile Glu Glu Arg Tyr Lys Ala
65                  70                  75                  80

Val Cys His Ala Ala Arg Thr Arg Ser Ile Leu Ser Leu Gly Leu Ala
                85                  90                  95

Cys Phe Lys Arg Gln Pro Asp Lys Gly Glu His Ser Tyr Leu Ala Gln
            100                 105                 110
```

```
Val Phe Asn Leu Thr Leu Leu Cys Met Glu Glu Tyr Val Ile Glu Pro
            115                 120                 125

Lys Ser Val Gln Phe Leu Ile Gln His Gly Phe Asn Phe Asn Gln Gln
130                 135                 140

Tyr Ala Gln Gly Ile Pro Tyr His Lys Gly Asn Asp Lys Gly Asp Glu
145                 150                 155                 160

Ser Gln Ser Gln Ser Val Arg Thr Leu Phe Leu Glu Leu Ile Arg Ala
                165                 170                 175

Arg Arg Pro Leu Val Leu His Asn Gly Leu Ile Asp Leu Val Phe Leu
            180                 185                 190

Tyr Gln Asn Phe Tyr Ala His Leu Pro Glu Ser Leu Gly Thr Phe Thr
            195                 200                 205

Ala Asp Leu Cys Glu Met Phe Pro Ala Gly Ile Tyr Asp Thr Lys Tyr
210                 215                 220

Ala Ala Glu Phe His Ala Arg Phe Val Ala Ser Tyr Leu Glu Tyr Ala
225                 230                 235                 240

Phe Arg Lys Cys Glu Arg Glu Asn Gly Lys Gln Arg Ala Ala Gly Ser
                245                 250                 255

Pro His Leu Thr Leu Glu Phe Cys Asn Tyr Pro Ser Ser Met Arg Asp
            260                 265                 270

His Ile Asp Tyr Arg Cys Cys Leu Pro Pro Ala Thr His Arg Pro His
            275                 280                 285

Pro Thr Ser Ile Cys Asp Asn Phe Ser Ala Tyr Gly Trp Cys Pro Leu
290                 295                 300

Gly Pro Gln Cys Pro Gln Ser His Asp Ile Asp Leu Ile Ile Asp Thr
305                 310                 315                 320

Asp Glu Ala Ala Ala Glu Asp Lys Arg Arg Arg Arg Arg Arg Arg Glu
                325                 330                 335

Lys Arg Lys Arg Ala Leu Leu Asn Leu Pro Gly Thr Gln Thr Ser Gly
            340                 345                 350

Glu Ala Lys Asp Gly Pro Pro Lys Lys Gln Val Cys Gly Asp Ser Ile
            355                 360                 365

Lys Pro Glu Glu Thr Gln Glu Val Ala Ala Asp Glu Thr Arg Asn
370                 375                 380

Leu Pro His Ser Lys Gln Gly Asn Lys Asn Asp Leu Glu Met Gly Ile
385                 390                 395                 400

Lys Ala Ala Arg Pro Glu Ile Ala Asp Arg Ala Thr Ser Glu Val Pro
                405                 410                 415

Gly Ser Gln Ala Ser Pro Asn Val Pro Gly Asp Gly Leu His Arg
            420                 425                 430

Ala Gly Phe Asp
            435

<210> SEQ ID NO 119
<211> LENGTH: 503
<212> TYPE: PRT
<213> ORGANISM: Artificial Sequence
<220> FEATURE:
<223> OTHER INFORMATION: G8/S510 Deletion mutant of TOE1

<400> SEQUENCE: 119

Gly Ala Val Ser Thr Pro Ala Ala Ser Asp Gly Gly Val Ser Lys Ser
1               5                   10                  15

Thr Thr Ser Gly Glu Glu Leu Val Val Gln Val Pro Val Val Asp Val
                20                  25                  30
```

```
Gln Ser Asn Asn Phe Lys Glu Met Trp Pro Ser Leu Leu Ala Ile
     35                  40                  45

Lys Thr Ala Asn Phe Val Ala Val Asp Thr Glu Leu Ser Gly Leu Gly
 50                  55                  60

Asp Arg Lys Ser Leu Leu Asn Gln Cys Ile Glu Glu Arg Tyr Lys Ala
 65                  70                  75                  80

Val Cys His Ala Ala Arg Thr Arg Ser Ile Leu Ser Leu Gly Leu Ala
                 85                  90                  95

Cys Phe Lys Arg Gln Pro Asp Lys Gly Glu His Ser Tyr Leu Ala Gln
            100                 105                 110

Val Phe Asn Leu Thr Leu Leu Cys Met Glu Glu Tyr Val Ile Glu Pro
        115                 120                 125

Lys Ser Val Gln Phe Leu Ile Gln His Gly Phe Asn Phe Asn Gln Gln
130                 135                 140

Tyr Ala Gln Gly Ile Pro Tyr His Lys Gly Asn Asp Lys Gly Asp Glu
145                 150                 155                 160

Ser Gln Ser Gln Ser Val Arg Thr Leu Phe Leu Glu Leu Ile Arg Ala
                165                 170                 175

Arg Arg Pro Leu Val Leu His Asn Gly Leu Ile Asp Leu Val Phe Leu
            180                 185                 190

Tyr Gln Asn Phe Tyr Ala His Leu Pro Glu Ser Leu Gly Thr Phe Thr
        195                 200                 205

Ala Asp Leu Cys Glu Met Phe Pro Ala Gly Ile Tyr Asp Thr Lys Tyr
210                 215                 220

Ala Ala Glu Phe His Ala Arg Phe Val Ala Ser Tyr Leu Glu Tyr Ala
225                 230                 235                 240

Phe Arg Lys Cys Glu Arg Glu Asn Gly Lys Gln Arg Ala Ala Gly Ser
                245                 250                 255

Pro His Leu Thr Leu Glu Phe Cys Asn Tyr Pro Ser Ser Met Arg Asp
            260                 265                 270

His Ile Asp Tyr Arg Cys Cys Leu Pro Pro Ala Thr His Arg Pro His
        275                 280                 285

Pro Thr Ser Ile Cys Asp Asn Phe Ser Ala Tyr Gly Trp Cys Pro Leu
290                 295                 300

Gly Pro Gln Cys Pro Gln Ser His Asp Ile Asp Leu Ile Ile Asp Thr
305                 310                 315                 320

Asp Glu Ala Ala Ala Glu Asp Lys Arg Arg Arg Arg Arg Arg Arg Glu
                325                 330                 335

Lys Arg Lys Arg Ala Leu Leu Asn Leu Pro Gly Thr Gln Thr Ser Gly
            340                 345                 350

Glu Ala Lys Asp Gly Pro Pro Lys Lys Gln Val Cys Gly Asp Ser Ile
        355                 360                 365

Lys Pro Glu Glu Thr Glu Gln Glu Val Ala Ala Asp Glu Thr Arg Asn
370                 375                 380

Leu Pro His Ser Lys Gln Gly Asn Lys Asn Asp Leu Glu Met Gly Ile
385                 390                 395                 400

Lys Ala Ala Arg Pro Glu Ile Ala Asp Arg Ala Thr Ser Glu Val Pro
                405                 410                 415

Gly Ser Gln Ala Ser Pro Asn Pro Val Pro Gly Asp Gly Leu His Arg
            420                 425                 430

Ala Gly Phe Asp Ala Phe Met Thr Gly Tyr Val Met Ala Tyr Val Glu
        435                 440                 445

Val Ser Gln Gly Pro Gln Pro Cys Ser Ser Gly Pro Trp Leu Pro Glu
```

```
                    450              455              460
Cys His Asn Lys Val Tyr Leu Ser Gly Lys Ala Val Pro Leu Thr Val
465                 470              475              480

Ala Lys Ser Gln Phe Ser Arg Ser Lys Ala His Asn Gln Lys Met
                    485              490              495

Lys Leu Thr Trp Gly Ser Ser
                500

<210> SEQ ID NO 120
<211> LENGTH: 359
<212> TYPE: PRT
<213> ORGANISM: Artificial Sequence
<220> FEATURE:
<223> OTHER INFORMATION: S5/D363 Deletion mutant of TOE1

<400> SEQUENCE: 120

Ser Asp Asp Gly Ala Val Ser Thr Pro Ala Ala Ser Asp Gly Gly Val
1               5                   10                  15

Ser Lys Ser Thr Thr Ser Gly Glu Glu Leu Val Val Gln Val Pro Val
                20                  25                  30

Val Asp Val Gln Ser Asn Asn Phe Lys Glu Met Trp Pro Ser Leu Leu
            35                  40                  45

Leu Ala Ile Lys Thr Ala Asn Phe Val Ala Val Asp Thr Glu Leu Ser
        50                  55                  60

Gly Leu Gly Asp Arg Lys Ser Leu Leu Asn Gln Cys Ile Glu Glu Arg
65                  70                  75                  80

Tyr Lys Ala Val Cys His Ala Ala Arg Thr Arg Ser Ile Leu Ser Leu
                85                  90                  95

Gly Leu Ala Cys Phe Lys Arg Gln Pro Asp Lys Gly Glu His Ser Tyr
            100                 105                 110

Leu Ala Gln Val Phe Asn Leu Thr Leu Leu Cys Met Glu Glu Tyr Val
        115                 120                 125

Ile Glu Pro Lys Ser Val Gln Phe Leu Ile Gln His Gly Phe Asn Phe
130                 135                 140

Asn Gln Gln Tyr Ala Gln Gly Ile Pro Tyr His Lys Gly Asn Asp Lys
145                 150                 155                 160

Gly Asp Glu Ser Gln Ser Gln Ser Val Arg Thr Leu Phe Leu Glu Leu
                165                 170                 175

Ile Arg Ala Arg Arg Pro Leu Val Leu His Asn Gly Leu Ile Asp Leu
            180                 185                 190

Val Phe Leu Tyr Gln Asn Phe Tyr Ala His Leu Pro Glu Ser Leu Gly
        195                 200                 205

Thr Phe Thr Ala Asp Leu Cys Glu Met Phe Pro Ala Gly Ile Tyr Asp
    210                 215                 220

Thr Lys Tyr Ala Ala Glu Phe His Ala Arg Phe Val Ala Ser Tyr Leu
225                 230                 235                 240

Glu Tyr Ala Phe Arg Lys Cys Glu Arg Glu Asn Gly Lys Gln Arg Ala
                245                 250                 255

Ala Gly Ser Pro His Leu Thr Leu Glu Phe Cys Asn Tyr Pro Ser Ser
            260                 265                 270

Met Arg Asp His Ile Asp Tyr Arg Cys Cys Leu Pro Pro Ala Thr His
        275                 280                 285

Arg Pro His Pro Thr Ser Ile Cys Asp Asn Phe Ser Ala Tyr Gly Trp
    290                 295                 300

Cys Pro Leu Gly Pro Gln Cys Pro Gln Ser His Asp Ile Asp Leu Ile
```

```
            305                 310                 315                 320
Ile Asp Thr Asp Glu Ala Ala Ala Glu Asp Lys Arg Arg Arg Arg
                325                 330                 335

Arg Arg Glu Lys Arg Lys Arg Ala Leu Leu Asn Leu Pro Gly Thr Gln
            340                 345                 350

Thr Ser Gly Glu Ala Lys Asp
        355

<210> SEQ ID NO 121
<211> LENGTH: 369
<212> TYPE: PRT
<213> ORGANISM: Artificial Sequence
<220> FEATURE:
<223> OTHER INFORMATION: S5/D373 Deletion mutant of TOE1

<400> SEQUENCE: 121

Ser Asp Asp Gly Ala Val Ser Thr Pro Ala Ala Ser Asp Gly Gly Val
1               5                   10                  15

Ser Lys Ser Thr Thr Ser Gly Glu Glu Leu Val Val Gln Val Pro Val
            20                  25                  30

Val Asp Val Gln Ser Asn Asn Phe Lys Glu Met Trp Pro Ser Leu Leu
        35                  40                  45

Leu Ala Ile Lys Thr Ala Asn Phe Val Ala Val Asp Thr Glu Leu Ser
    50                  55                  60

Gly Leu Gly Asp Arg Lys Ser Leu Leu Asn Gln Cys Ile Glu Glu Arg
65                  70                  75                  80

Tyr Lys Ala Val Cys His Ala Ala Arg Thr Arg Ser Ile Leu Ser Leu
                85                  90                  95

Gly Leu Ala Cys Phe Lys Arg Gln Pro Asp Lys Gly Glu His Ser Tyr
            100                 105                 110

Leu Ala Gln Val Phe Asn Leu Thr Leu Leu Cys Met Glu Glu Tyr Val
        115                 120                 125

Ile Glu Pro Lys Ser Val Gln Phe Leu Ile Gln His Gly Phe Asn Phe
    130                 135                 140

Asn Gln Gln Tyr Ala Gln Gly Ile Pro Tyr His Lys Gly Asn Asp Lys
145                 150                 155                 160

Gly Asp Glu Ser Gln Ser Gln Ser Val Arg Thr Leu Phe Leu Glu Leu
                165                 170                 175

Ile Arg Ala Arg Arg Pro Leu Val Leu His Asn Gly Leu Ile Asp Leu
            180                 185                 190

Val Phe Leu Tyr Gln Asn Phe Tyr Ala His Leu Pro Glu Ser Leu Gly
        195                 200                 205

Thr Phe Thr Ala Asp Leu Cys Glu Met Phe Pro Ala Gly Ile Tyr Asp
    210                 215                 220

Thr Lys Tyr Ala Ala Glu Phe His Ala Arg Phe Val Ala Ser Tyr Leu
225                 230                 235                 240

Glu Tyr Ala Phe Arg Lys Cys Glu Arg Glu Asn Gly Lys Gln Arg Ala
                245                 250                 255

Ala Gly Ser Pro His Leu Thr Leu Glu Phe Cys Asn Tyr Pro Ser Ser
            260                 265                 270

Met Arg Asp His Ile Asp Tyr Arg Cys Cys Leu Pro Pro Ala Thr His
        275                 280                 285

Arg Pro His Pro Thr Ser Ile Cys Asp Asn Phe Ser Ala Tyr Gly Trp
    290                 295                 300

Cys Pro Leu Gly Pro Gln Cys Pro Gln Ser His Asp Ile Asp Leu Ile
```

```
                305                 310                 315                 320
Ile Asp Thr Asp Glu Ala Ala Glu Asp Lys Arg Arg Arg Arg
                    325                 330                 335
Arg Arg Glu Lys Arg Lys Arg Ala Leu Leu Asn Leu Pro Gly Thr Gln
                340                 345                 350
Thr Ser Gly Glu Ala Lys Asp Gly Pro Pro Lys Lys Gln Val Cys Gly
                355                 360                 365
Asp
```

<210> SEQ ID NO 122
<211> LENGTH: 383
<212> TYPE: PRT
<213> ORGANISM: Artificial Sequence
<220> FEATURE:
<223> OTHER INFORMATION: S5/D387 Deletion mutant of TOE1

<400> SEQUENCE: 122

```
Ser Asp Asp Gly Ala Val Ser Thr Pro Ala Ala Ser Asp Gly Gly Val
1               5                   10                  15
Ser Lys Ser Thr Thr Ser Gly Glu Glu Leu Val Val Gln Val Pro Val
                20                  25                  30
Val Asp Val Gln Ser Asn Asn Phe Lys Glu Met Trp Pro Ser Leu Leu
                35                  40                  45
Leu Ala Ile Lys Thr Ala Asn Phe Val Ala Val Asp Thr Glu Leu Ser
            50                  55                  60
Gly Leu Gly Asp Arg Lys Ser Leu Leu Asn Gln Cys Ile Glu Glu Arg
65                  70                  75                  80
Tyr Lys Ala Val Cys His Ala Ala Arg Thr Arg Ser Ile Leu Ser Leu
                85                  90                  95
Gly Leu Ala Cys Phe Lys Arg Gln Pro Asp Lys Gly Glu His Ser Tyr
                100                 105                 110
Leu Ala Gln Val Phe Asn Leu Thr Leu Leu Cys Met Glu Glu Tyr Val
            115                 120                 125
Ile Glu Pro Lys Ser Val Gln Phe Leu Ile Gln His Gly Phe Asn Phe
130                 135                 140
Asn Gln Gln Tyr Ala Gln Gly Ile Pro Tyr His Lys Gly Asn Asp Lys
145                 150                 155                 160
Gly Asp Glu Ser Gln Ser Gln Ser Val Arg Thr Leu Phe Leu Glu Leu
                165                 170                 175
Ile Arg Ala Arg Arg Pro Leu Val Leu His Asn Gly Leu Ile Asp Leu
                180                 185                 190
Val Phe Leu Tyr Gln Asn Phe Tyr Ala His Leu Pro Glu Ser Leu Gly
            195                 200                 205
Thr Phe Thr Ala Asp Leu Cys Glu Met Phe Pro Ala Gly Ile Tyr Asp
        210                 215                 220
Thr Lys Tyr Ala Ala Glu Phe His Ala Arg Phe Val Ala Ser Tyr Leu
225                 230                 235                 240
Glu Tyr Ala Phe Arg Lys Cys Glu Arg Glu Asn Gly Lys Gln Arg Ala
                245                 250                 255
Ala Gly Ser Pro His Leu Thr Leu Glu Phe Cys Asn Tyr Pro Ser Ser
                260                 265                 270
Met Arg Asp His Ile Asp Tyr Arg Cys Cys Leu Pro Pro Ala Thr His
            275                 280                 285
Arg Pro His Pro Thr Ser Ile Cys Asp Asn Phe Ser Ala Tyr Gly Trp
        290                 295                 300
```

```
Cys Pro Leu Gly Pro Gln Cys Pro Gln Ser His Asp Ile Asp Leu Ile
305                 310                 315                 320

Ile Asp Thr Asp Glu Ala Ala Glu Asp Lys Arg Arg Arg Arg
            325                 330                 335

Arg Arg Glu Lys Arg Lys Arg Ala Leu Leu Asn Leu Pro Gly Thr Gln
            340                 345                 350

Thr Ser Gly Glu Ala Lys Asp Gly Pro Pro Lys Lys Gln Val Cys Gly
            355                 360                 365

Asp Ser Ile Lys Pro Glu Glu Thr Glu Gln Glu Val Ala Ala Asp
            370                 375                 380

<210> SEQ ID NO 123
<211> LENGTH: 398
<212> TYPE: PRT
<213> ORGANISM: Artificial Sequence
<220> FEATURE:
<223> OTHER INFORMATION: S5/D402 Deletion mutant of TOE1

<400> SEQUENCE: 123

Ser Asp Asp Gly Ala Val Ser Thr Pro Ala Ala Ser Asp Gly Gly Val
1               5                   10                  15

Ser Lys Ser Thr Thr Ser Gly Glu Glu Leu Val Val Gln Val Pro Val
                20                  25                  30

Val Asp Val Gln Ser Asn Asn Phe Lys Glu Met Trp Pro Ser Leu Leu
            35                  40                  45

Leu Ala Ile Lys Thr Ala Asn Phe Val Ala Val Asp Thr Glu Leu Ser
        50                  55                  60

Gly Leu Gly Asp Arg Lys Ser Leu Leu Asn Gln Cys Ile Glu Glu Arg
65                  70                  75                  80

Tyr Lys Ala Val Cys His Ala Ala Arg Thr Arg Ser Ile Leu Ser Leu
                85                  90                  95

Gly Leu Ala Cys Phe Lys Arg Gln Pro Asp Lys Gly Glu His Ser Tyr
            100                 105                 110

Leu Ala Gln Val Phe Asn Leu Thr Leu Leu Cys Met Glu Glu Tyr Val
        115                 120                 125

Ile Glu Pro Lys Ser Val Gln Phe Leu Ile Gln His Gly Phe Asn Phe
130                 135                 140

Asn Gln Gln Tyr Ala Gln Gly Ile Pro Tyr His Lys Gly Asn Asp Lys
145                 150                 155                 160

Gly Asp Glu Ser Gln Ser Gln Ser Val Arg Thr Leu Phe Leu Glu Leu
                165                 170                 175

Ile Arg Ala Arg Arg Pro Leu Val Leu His Asn Gly Leu Ile Asp Leu
            180                 185                 190

Val Phe Leu Tyr Gln Asn Phe Tyr Ala His Leu Pro Glu Ser Leu Gly
        195                 200                 205

Thr Phe Thr Ala Asp Leu Cys Glu Met Phe Pro Ala Gly Ile Tyr Asp
    210                 215                 220

Thr Lys Tyr Ala Ala Glu Phe His Ala Arg Phe Val Ala Ser Tyr Leu
225                 230                 235                 240

Glu Tyr Ala Phe Arg Lys Cys Glu Arg Glu Asn Gly Lys Gln Arg Ala
                245                 250                 255

Ala Gly Ser Pro His Leu Thr Leu Glu Phe Cys Asn Tyr Pro Ser Ser
            260                 265                 270

Met Arg Asp His Ile Asp Tyr Arg Cys Cys Leu Pro Pro Ala Thr His
        275                 280                 285
```

```
Arg Pro His Pro Thr Ser Ile Cys Asp Asn Phe Ser Ala Tyr Gly Trp
            290                 295                 300

Cys Pro Leu Gly Pro Gln Cys Pro Gln Ser His Asp Ile Asp Leu Ile
305                 310                 315                 320

Ile Asp Thr Asp Glu Ala Ala Ala Glu Asp Lys Arg Arg Arg Arg Arg
                325                 330                 335

Arg Arg Glu Lys Arg Lys Arg Ala Leu Leu Asn Leu Pro Gly Thr Gln
            340                 345                 350

Thr Ser Gly Glu Ala Lys Asp Gly Pro Pro Lys Lys Gln Val Cys Gly
            355                 360                 365

Asp Ser Ile Lys Pro Glu Glu Thr Glu Gln Val Ala Ala Asp Glu
            370                 375                 380

Thr Arg Asn Leu Pro His Ser Lys Gln Gly Asn Lys Asn Asp
385                 390                 395

<210> SEQ ID NO 124
<211> LENGTH: 412
<212> TYPE: PRT
<213> ORGANISM: Artificial Sequence
<220> FEATURE:
<223> OTHER INFORMATION: S5/D416 Deletion mutant of TOE1

<400> SEQUENCE: 124

Ser Asp Asp Gly Ala Val Ser Thr Pro Ala Ala Ser Asp Gly Gly Val
1               5                   10                  15

Ser Lys Ser Thr Thr Ser Gly Glu Glu Leu Val Val Gln Val Pro Val
            20                  25                  30

Val Asp Val Gln Ser Asn Asn Phe Lys Glu Met Trp Pro Ser Leu Leu
        35                  40                  45

Leu Ala Ile Lys Thr Ala Asn Phe Val Ala Val Asp Thr Glu Leu Ser
    50                  55                  60

Gly Leu Gly Asp Arg Lys Ser Leu Leu Asn Gln Cys Ile Glu Glu Arg
65                  70                  75                  80

Tyr Lys Ala Val Cys His Ala Ala Arg Thr Arg Ser Ile Leu Ser Leu
                85                  90                  95

Gly Leu Ala Cys Phe Lys Arg Gln Pro Asp Lys Gly Glu His Ser Tyr
            100                 105                 110

Leu Ala Gln Val Phe Asn Leu Thr Leu Leu Cys Met Glu Glu Tyr Val
        115                 120                 125

Ile Glu Pro Lys Ser Val Gln Phe Leu Ile Gln His Gly Phe Asn Phe
    130                 135                 140

Asn Gln Gln Tyr Ala Gln Gly Ile Pro Tyr His Lys Gly Asn Asp Lys
145                 150                 155                 160

Gly Asp Glu Ser Gln Ser Gln Ser Val Arg Thr Leu Phe Leu Glu Leu
                165                 170                 175

Ile Arg Ala Arg Arg Pro Leu Val Leu His Asn Gly Leu Ile Asp Leu
            180                 185                 190

Val Phe Leu Tyr Gln Asn Phe Tyr Ala His Leu Pro Glu Ser Leu Gly
        195                 200                 205

Thr Phe Thr Ala Asp Leu Cys Glu Met Phe Pro Ala Gly Ile Tyr Asp
    210                 215                 220

Thr Lys Tyr Ala Ala Glu Phe His Ala Arg Phe Val Ala Ser Tyr Leu
225                 230                 235                 240

Glu Tyr Ala Phe Arg Lys Cys Glu Arg Glu Asn Gly Lys Gln Arg Ala
                245                 250                 255
```

```
Ala Gly Ser Pro His Leu Thr Leu Glu Phe Cys Asn Tyr Pro Ser Ser
            260                 265                 270

Met Arg Asp His Ile Asp Tyr Arg Cys Cys Leu Pro Pro Ala Thr His
            275                 280                 285

Arg Pro His Pro Thr Ser Ile Cys Asp Asn Phe Ser Ala Tyr Gly Trp
            290                 295                 300

Cys Pro Leu Gly Pro Gln Cys Pro Gln Ser His Asp Ile Asp Leu Ile
305                 310                 315                 320

Ile Asp Thr Asp Glu Ala Ala Glu Asp Lys Arg Arg Arg Arg
                325                 330                 335

Arg Arg Glu Lys Arg Lys Arg Ala Leu Leu Asn Leu Pro Gly Thr Gln
            340                 345                 350

Thr Ser Gly Glu Ala Lys Asp Gly Pro Pro Lys Lys Gln Val Cys Gly
            355                 360                 365

Asp Ser Ile Lys Pro Glu Glu Thr Gly Gln Glu Val Ala Ala Asp Glu
            370                 375                 380

Thr Arg Asn Leu Pro His Ser Lys Gln Gly Asn Lys Asn Asp Leu Glu
385                 390                 395                 400

Met Gly Ile Lys Ala Ala Arg Pro Glu Ile Ala Asp
                405                 410

<210> SEQ ID NO 125
<211> LENGTH: 431
<212> TYPE: PRT
<213> ORGANISM: Artificial Sequence
<220> FEATURE:
<223> OTHER INFORMATION: S5/D435 Deletion mutant of TOE1

<400> SEQUENCE: 125

Ser Asp Asp Gly Ala Val Ser Thr Pro Ala Ala Ser Asp Gly Gly Val
1               5                   10                  15

Ser Lys Ser Thr Thr Ser Gly Glu Glu Leu Val Val Gln Val Pro Val
            20                  25                  30

Val Asp Val Gln Ser Asn Asn Phe Lys Glu Met Trp Pro Ser Leu Leu
            35                  40                  45

Leu Ala Ile Lys Thr Ala Asn Phe Val Ala Val Asp Thr Glu Leu Ser
        50                  55                  60

Gly Leu Gly Asp Arg Lys Ser Leu Leu Asn Gln Cys Ile Glu Glu Arg
65                  70                  75                  80

Tyr Lys Ala Val Cys His Ala Ala Arg Thr Arg Ser Ile Leu Ser Leu
                85                  90                  95

Gly Leu Ala Cys Phe Lys Arg Gln Pro Asp Lys Gly Glu His Ser Tyr
            100                 105                 110

Leu Ala Gln Val Phe Asn Leu Thr Leu Leu Cys Met Glu Glu Tyr Val
        115                 120                 125

Ile Glu Pro Lys Ser Val Gln Phe Leu Ile Gln His Gly Phe Asn Phe
    130                 135                 140

Asn Gln Gln Tyr Ala Gln Gly Ile Pro Tyr His Lys Gly Asn Asp Lys
145                 150                 155                 160

Gly Asp Glu Ser Gln Ser Gln Val Arg Thr Leu Phe Leu Glu Leu
                165                 170                 175

Ile Arg Ala Arg Arg Pro Leu Val Leu His Asn Gly Leu Ile Asp Leu
            180                 185                 190

Val Phe Leu Tyr Gln Asn Phe Tyr Ala His Leu Pro Glu Ser Leu Gly
        195                 200                 205
```

```
Thr Phe Thr Ala Asp Leu Cys Glu Met Phe Pro Ala Gly Ile Tyr Asp
    210                 215                 220
Thr Lys Tyr Ala Ala Glu Phe His Ala Arg Phe Val Ala Ser Tyr Leu
225                 230                 235                 240
Glu Tyr Ala Phe Arg Lys Cys Glu Arg Glu Asn Gly Lys Gln Arg Ala
                245                 250                 255
Ala Gly Ser Pro His Leu Thr Leu Glu Phe Cys Asn Tyr Pro Ser Ser
            260                 265                 270
Met Arg Asp His Ile Asp Tyr Arg Cys Cys Leu Pro Pro Ala Thr His
        275                 280                 285
Arg Pro His Pro Thr Ser Ile Cys Asp Asn Phe Ser Ala Tyr Gly Trp
    290                 295                 300
Cys Pro Leu Gly Pro Gln Cys Pro Gln Ser His Asp Ile Asp Leu Ile
305                 310                 315                 320
Ile Asp Thr Asp Glu Ala Ala Ala Glu Asp Lys Arg Arg Arg Arg Arg
                325                 330                 335
Arg Arg Glu Lys Arg Lys Arg Ala Leu Leu Asn Leu Pro Gly Thr Gln
            340                 345                 350
Thr Ser Gly Glu Ala Lys Asp Gly Pro Pro Lys Lys Gln Val Cys Gly
        355                 360                 365
Asp Ser Ile Lys Pro Glu Glu Thr Gln Glu Val Ala Ala Asp Glu
    370                 375                 380
Thr Arg Asn Leu Pro His Ser Lys Gln Gly Asn Lys Asn Asp Leu Glu
385                 390                 395                 400
Met Gly Ile Lys Ala Ala Arg Pro Glu Ile Ala Asp Arg Ala Thr Ser
                405                 410                 415
Glu Val Pro Gly Ser Gln Ala Ser Pro Asn Pro Val Pro Gly Asp
            420                 425                 430

<210> SEQ ID NO 126
<211> LENGTH: 439
<212> TYPE: PRT
<213> ORGANISM: Artificial Sequence
<220> FEATURE:
<223> OTHER INFORMATION: S5/D443 Deletion mutant of TOE1

<400> SEQUENCE: 126

Ser Asp Asp Gly Ala Val Ser Thr Pro Ala Ala Ser Asp Gly Gly Val
1               5                   10                  15
Ser Lys Ser Thr Thr Ser Gly Glu Glu Leu Val Val Gln Val Pro Val
                20                  25                  30
Val Asp Val Gln Ser Asn Asn Phe Lys Glu Met Trp Pro Ser Leu Leu
            35                  40                  45
Leu Ala Ile Lys Thr Ala Asn Phe Val Ala Val Asp Thr Glu Leu Ser
        50                  55                  60
Gly Leu Gly Asp Arg Lys Ser Leu Leu Asn Gln Cys Ile Glu Glu Arg
65                  70                  75                  80
Tyr Lys Ala Val Cys His Ala Ala Arg Thr Arg Ser Ile Leu Ser Leu
                85                  90                  95
Gly Leu Ala Cys Phe Lys Arg Gln Pro Asp Lys Gly Glu His Ser Tyr
            100                 105                 110
Leu Ala Gln Val Phe Asn Leu Thr Leu Leu Cys Met Glu Glu Tyr Val
        115                 120                 125
Ile Glu Pro Lys Ser Val Gln Phe Leu Ile Gln His Gly Phe Asn Phe
    130                 135                 140
```

Asn Gln Gln Tyr Ala Gln Gly Ile Pro Tyr His Lys Gly Asn Asp Lys
145                 150                 155                 160

Gly Asp Glu Ser Gln Ser Gln Ser Val Arg Thr Leu Phe Leu Glu Leu
            165                 170                 175

Ile Arg Ala Arg Arg Pro Leu Val Leu His Asn Gly Leu Ile Asp Leu
        180                 185                 190

Val Phe Leu Tyr Gln Asn Phe Tyr Ala His Leu Pro Glu Ser Leu Gly
            195                 200                 205

Thr Phe Thr Ala Asp Leu Cys Glu Met Phe Pro Ala Gly Ile Tyr Asp
        210                 215                 220

Thr Lys Tyr Ala Ala Glu Phe His Ala Arg Phe Val Ala Ser Tyr Leu
225                 230                 235                 240

Glu Tyr Ala Phe Arg Lys Cys Glu Arg Glu Asn Gly Lys Gln Arg Ala
                245                 250                 255

Ala Gly Ser Pro His Leu Thr Leu Glu Phe Cys Asn Tyr Pro Ser Ser
            260                 265                 270

Met Arg Asp His Ile Asp Tyr Arg Cys Cys Leu Pro Pro Ala Thr His
        275                 280                 285

Arg Pro His Pro Thr Ser Ile Cys Asp Asn Phe Ser Ala Tyr Gly Trp
    290                 295                 300

Cys Pro Leu Gly Pro Gln Cys Pro Gln Ser His Asp Ile Asp Leu Ile
305                 310                 315                 320

Ile Asp Thr Asp Glu Ala Ala Ala Glu Asp Lys Arg Arg Arg Arg Arg
                325                 330                 335

Arg Arg Glu Lys Arg Lys Arg Ala Leu Leu Asn Leu Pro Gly Thr Gln
            340                 345                 350

Thr Ser Gly Glu Ala Lys Asp Gly Pro Pro Lys Lys Gln Val Cys Gly
        355                 360                 365

Asp Ser Ile Lys Pro Glu Glu Thr Gln Glu Val Ala Ala Asp Glu
    370                 375                 380

Thr Arg Asn Leu Pro His Ser Lys Gln Gly Asn Lys Asn Asp Leu Glu
385                 390                 395                 400

Met Gly Ile Lys Ala Ala Arg Pro Glu Ile Ala Asp Arg Ala Thr Ser
                405                 410                 415

Glu Val Pro Gly Ser Gln Ala Ser Pro Asn Pro Val Pro Gly Asp Gly
            420                 425                 430

Leu His Arg Ala Gly Phe Asp
        435

<210> SEQ ID NO 127
<211> LENGTH: 506
<212> TYPE: PRT
<213> ORGANISM: Artificial Sequence
<220> FEATURE:
<223> OTHER INFORMATION: S5/S510 Deletion mutant of TOE1

<400> SEQUENCE: 127

Ser Asp Asp Gly Ala Val Ser Thr Pro Ala Ser Asp Gly Gly Val
1               5                   10                  15

Ser Lys Ser Thr Thr Ser Gly Glu Glu Leu Val Val Gln Val Pro Val
            20                  25                  30

Val Asp Val Gln Ser Asn Asn Phe Lys Glu Met Trp Pro Ser Leu Leu
        35                  40                  45

Leu Ala Ile Lys Thr Ala Asn Phe Val Ala Val Asp Thr Glu Leu Ser
    50                  55                  60

-continued

```
Gly Leu Gly Asp Arg Lys Ser Leu Leu Asn Gln Cys Ile Glu Glu Arg
 65                  70                  75                  80

Tyr Lys Ala Val Cys His Ala Ala Arg Thr Arg Ser Ile Leu Ser Leu
                 85                  90                  95

Gly Leu Ala Cys Phe Lys Arg Gln Pro Asp Lys Gly Glu His Ser Tyr
            100                 105                 110

Leu Ala Gln Val Phe Asn Leu Thr Leu Leu Cys Met Glu Glu Tyr Val
        115                 120                 125

Ile Glu Pro Lys Ser Val Gln Phe Leu Ile Gln His Gly Phe Asn Phe
    130                 135                 140

Asn Gln Gln Tyr Ala Gln Gly Ile Pro Tyr His Lys Gly Asn Asp Lys
145                 150                 155                 160

Gly Asp Glu Ser Gln Ser Gln Ser Val Arg Thr Leu Phe Leu Glu Leu
                165                 170                 175

Ile Arg Ala Arg Arg Pro Leu Val Leu His Asn Gly Leu Ile Asp Leu
            180                 185                 190

Val Phe Leu Tyr Gln Asn Phe Tyr Ala His Leu Pro Glu Ser Leu Gly
        195                 200                 205

Thr Phe Thr Ala Asp Leu Cys Glu Met Phe Pro Ala Gly Ile Tyr Asp
    210                 215                 220

Thr Lys Tyr Ala Ala Glu Phe His Ala Arg Phe Val Ala Ser Tyr Leu
225                 230                 235                 240

Glu Tyr Ala Phe Arg Lys Cys Glu Arg Glu Asn Gly Lys Gln Arg Ala
                245                 250                 255

Ala Gly Ser Pro His Leu Thr Leu Glu Phe Cys Asn Tyr Pro Ser Ser
            260                 265                 270

Met Arg Asp His Ile Asp Tyr Arg Cys Cys Leu Pro Pro Ala Thr His
        275                 280                 285

Arg Pro His Pro Thr Ser Ile Cys Asp Asn Phe Ser Ala Tyr Gly Trp
    290                 295                 300

Cys Pro Leu Gly Pro Gln Cys Pro Gln Ser His Asp Ile Asp Leu Ile
305                 310                 315                 320

Ile Asp Thr Asp Glu Ala Ala Ala Glu Asp Lys Arg Arg Arg Arg Arg
                325                 330                 335

Arg Arg Glu Lys Arg Lys Arg Ala Leu Leu Asn Leu Pro Gly Thr Gln
            340                 345                 350

Thr Ser Gly Glu Ala Lys Asp Gly Pro Pro Lys Lys Gln Val Cys Gly
        355                 360                 365

Asp Ser Ile Lys Pro Glu Glu Thr Glu Gln Glu Val Ala Ala Asp Glu
    370                 375                 380

Thr Arg Asn Leu Pro His Ser Lys Gln Gly Asn Lys Asn Asp Leu Glu
385                 390                 395                 400

Met Gly Ile Lys Ala Ala Arg Pro Glu Ile Ala Asp Arg Ala Thr Ser
                405                 410                 415

Glu Val Pro Gly Ser Gln Ala Ser Pro Asn Pro Val Pro Gly Asp Gly
            420                 425                 430

Leu His Arg Ala Gly Phe Asp Ala Phe Met Thr Gly Tyr Val Met Ala
        435                 440                 445

Tyr Val Glu Val Ser Gln Gly Pro Gln Pro Cys Ser Ser Gly Pro Trp
    450                 455                 460

Leu Pro Glu Cys His Asn Lys Val Tyr Leu Ser Gly Lys Ala Val Pro
465                 470                 475                 480
```

```
Leu Thr Val Ala Lys Ser Gln Phe Ser Arg Ser Ser Lys Ala His Asn
                485                 490                 495

Gln Lys Met Lys Leu Thr Trp Gly Ser Ser
        500                 505

<210> SEQ ID NO 128
<211> LENGTH: 402
<212> TYPE: PRT
<213> ORGANISM: Artificial Sequence
<220> FEATURE:
<223> OTHER INFORMATION: M1/D402 deletion mutant of TOE1

<400> SEQUENCE: 128

Met Ala Ala Asp Ser Asp Asp Gly Ala Val Ser Thr Pro Ala Ala Ser
1               5                   10                  15

Asp Gly Gly Val Ser Lys Ser Thr Thr Ser Gly Glu Glu Leu Val Val
            20                  25                  30

Gln Val Pro Val Val Asp Val Gln Ser Asn Asn Phe Lys Glu Met Trp
        35                  40                  45

Pro Ser Leu Leu Leu Ala Ile Lys Thr Ala Asn Phe Val Ala Val Asp
    50                  55                  60

Thr Glu Leu Ser Gly Leu Gly Asp Arg Lys Ser Leu Leu Asn Gln Cys
65                  70                  75                  80

Ile Glu Glu Arg Tyr Lys Ala Val Cys His Ala Ala Arg Thr Arg Ser
                85                  90                  95

Ile Leu Ser Leu Gly Leu Ala Cys Phe Lys Arg Gln Pro Asp Lys Gly
            100                 105                 110

Glu His Ser Tyr Leu Ala Gln Val Phe Asn Leu Thr Leu Leu Cys Met
        115                 120                 125

Glu Glu Tyr Val Ile Glu Pro Lys Ser Val Gln Phe Leu Ile Gln His
130                 135                 140

Gly Phe Asn Phe Asn Gln Gln Tyr Ala Gln Gly Ile Pro Tyr His Lys
145                 150                 155                 160

Gly Asn Asp Lys Gly Asp Glu Ser Gln Ser Gln Ser Val Arg Thr Leu
                165                 170                 175

Phe Leu Glu Leu Ile Arg Ala Arg Arg Pro Leu Val Leu His Asn Gly
            180                 185                 190

Leu Ile Asp Leu Val Phe Leu Tyr Gln Asn Phe Tyr Ala His Leu Pro
        195                 200                 205

Glu Ser Leu Gly Thr Phe Thr Ala Asp Leu Cys Glu Met Phe Pro Ala
210                 215                 220

Gly Ile Tyr Asp Thr Lys Tyr Ala Ala Glu Phe His Ala Arg Phe Val
225                 230                 235                 240

Ala Ser Tyr Leu Glu Tyr Ala Phe Arg Lys Cys Glu Arg Glu Asn Gly
                245                 250                 255

Lys Gln Arg Ala Ala Gly Ser Pro His Leu Thr Leu Glu Phe Cys Asn
            260                 265                 270

Tyr Pro Ser Ser Met Arg Asp His Ile Asp Tyr Arg Cys Cys Leu Pro
        275                 280                 285

Pro Ala Thr His Arg Pro His Pro Thr Ser Ile Cys Asp Asn Phe Ser
    290                 295                 300

Ala Tyr Gly Trp Cys Pro Leu Gly Pro Gln Cys Pro Gln Ser His Asp
305                 310                 315                 320

Ile Asp Leu Ile Ile Asp Thr Asp Glu Ala Ala Glu Asp Lys Arg
                325                 330                 335
```

```
Arg Arg Arg Arg Arg Arg Glu Lys Arg Lys Arg Ala Leu Leu Asn Leu
                340                 345                 350

Pro Gly Thr Gln Thr Ser Gly Glu Ala Lys Asp Gly Pro Pro Lys Lys
        355                 360                 365

Gln Val Cys Gly Asp Ser Ile Lys Pro Glu Glu Thr Glu Gln Glu Val
370                 375                 380

Ala Ala Asp Glu Thr Arg Asn Leu Pro His Ser Lys Gln Gly Asn Lys
385                 390                 395                 400

Asn Asp

<210> SEQ ID NO 129
<211> LENGTH: 373
<212> TYPE: PRT
<213> ORGANISM: Artificial Sequence
<220> FEATURE:
<223> OTHER INFORMATION: M1/D373 deletion mutant of TOE1

<400> SEQUENCE: 129

Met Ala Ala Asp Ser Asp Asp Gly Ala Val Ser Thr Pro Ala Ala Ser
1               5                   10                  15

Asp Gly Gly Val Ser Lys Ser Thr Thr Ser Gly Glu Glu Leu Val Val
                20                  25                  30

Gln Val Pro Val Val Asp Val Gln Ser Asn Asn Phe Lys Glu Met Trp
            35                  40                  45

Pro Ser Leu Leu Leu Ala Ile Lys Thr Ala Asn Phe Val Ala Val Asp
        50                  55                  60

Thr Glu Leu Ser Gly Leu Gly Asp Arg Lys Ser Leu Leu Asn Gln Cys
65                  70                  75                  80

Ile Glu Glu Arg Tyr Lys Ala Val Cys His Ala Ala Arg Thr Arg Ser
                85                  90                  95

Ile Leu Ser Leu Gly Leu Ala Cys Phe Lys Arg Gln Pro Asp Lys Gly
            100                 105                 110

Glu His Ser Tyr Leu Ala Gln Val Phe Asn Leu Thr Leu Leu Cys Met
        115                 120                 125

Glu Glu Tyr Val Ile Glu Pro Lys Ser Val Gln Phe Leu Ile Gln His
130                 135                 140

Gly Phe Asn Phe Asn Gln Gln Tyr Ala Gln Gly Ile Pro Tyr His Lys
145                 150                 155                 160

Gly Asn Asp Lys Gly Asp Glu Ser Gln Ser Gln Ser Val Arg Thr Leu
                165                 170                 175

Phe Leu Glu Leu Ile Arg Ala Arg Arg Pro Leu Val Leu His Asn Gly
            180                 185                 190

Leu Ile Asp Leu Val Phe Leu Tyr Gln Asn Phe Tyr Ala His Leu Pro
        195                 200                 205

Glu Ser Leu Gly Thr Phe Thr Ala Asp Leu Cys Glu Met Phe Pro Ala
210                 215                 220

Gly Ile Tyr Asp Thr Lys Tyr Ala Ala Glu Phe His Ala Arg Phe Val
225                 230                 235                 240

Ala Ser Tyr Leu Glu Tyr Ala Phe Arg Lys Cys Glu Arg Glu Asn Gly
                245                 250                 255

Lys Gln Arg Ala Ala Gly Ser Pro His Leu Thr Leu Glu Phe Cys Asn
            260                 265                 270

Tyr Pro Ser Ser Met Arg Asp His Ile Asp Tyr Arg Cys Cys Leu Pro
        275                 280                 285
```

-continued

```
Pro Ala Thr His Arg Pro His Pro Thr Ser Ile Cys Asp Asn Phe Ser
    290                 295             300

Ala Tyr Gly Trp Cys Pro Leu Gly Pro Gln Cys Pro Gln Ser His Asp
305                 310                 315                 320

Ile Asp Leu Ile Ile Asp Thr Asp Glu Ala Ala Ala Glu Asp Lys Arg
                325                 330                 335

Arg Arg Arg Arg Arg Arg Glu Lys Arg Lys Arg Ala Leu Leu Asn Leu
                340                 345                 350

Pro Gly Thr Gln Thr Ser Gly Glu Ala Lys Asp Gly Pro Pro Lys Lys
        355                 360                 365

Gln Val Cys Gly Asp
    370
```